US007534939B2

(12) United States Patent
Baum et al.

(10) Patent No.: US 7,534,939 B2
(45) Date of Patent: May 19, 2009

(54) **PLANT TRANSFORMED WITH POLYNUCLEOTIDE ENCODING LEPIDOPTERAN-ACTIVE *BACILLUS THURINGIENSIS* δ-ENDOTOXIN**

(75) Inventors: James A. Baum, Webster Groves, MO (US); Chih-Rei Chu, Exton, PA (US); William P. Donovan, Levittown, PA (US); Amy J. Gilmer, Langhorne, PA (US); Mark J. Rupar, Wilmington, DE (US)

(73) Assignee: Monsanto Technology LLC, St. Louis, MO (US)

( * ) Notice: Subject to any disclaimer, the term of this patent is extended or adjusted under 35 U.S.C. 154(b) by 138 days.

(21) Appl. No.: 11/487,813

(22) Filed: Jul. 17, 2006

(65) Prior Publication Data

US 2009/0098099 A1    Apr. 16, 2009

Related U.S. Application Data

(62) Division of application No. 10/428,961, filed on May 2, 2003, now Pat. No. 7,078,509, which is a division of application No. 09/661,322, filed on Sep. 13, 2000, now Pat. No. 6,593,293.

(60) Provisional application No. 60/153,995, filed on Sep. 15, 1999.

(51) Int. Cl.
*A01H 5/00*   (2006.01)
*A01H 5/10*   (2006.01)
*C12N 15/82*  (2006.01)

(52) U.S. Cl. .................. 800/302; 800/279; 800/320
(58) Field of Classification Search .................. None
See application file for complete search history.

(56) References Cited

U.S. PATENT DOCUMENTS 5,338,544 A    8/1994   Donovan ................ 424/93.2
5,723,758 A    3/1998   Payne et al. ............ 800/205
5,985,267 A    11/1999  Payne et al. .......... 424/93.461
6,107,278 A    8/2000   Schnepf et al. ............ 514/12
7,244,880 B2   7/2007   Arnaut et al. ............. 800/302

FOREIGN PATENT DOCUMENTS

| EP | 206 613 | 12/1986 |
| EP | 367 474 | 5/1990 |
| WO | WO 95/06128 | 3/1995 |
| WO | WO 98/00546 | 1/1998 |
| WO | WO 98/23641 | 6/1998 |
| WO | WO 98/40490 | 9/1998 |
| WO | WO 99/33991 | 7/1999 |
| WO | WO 02/057664 | 7/2002 |

OTHER PUBLICATIONS

Donovan et al (1988, J. Biol. Chem. 263:561-567).*
Schnepf et al., 1998, "*Bacillus thuringiensis* and Its Pesticidal Crystal Proteins." *Microbiol. Mol. Biol. Rev.* 62(3): 775-806.
Kuo et al. "*Bacillus thuringiensis* wuhanenis Insecticidal Crystal Protein CryE1 (cryLa1) gene, complete CDS." EMBL sequence database, Jan. 6, 1999. XP002160714. Ac U70726.
Hofte, H. et al. 1989. "Insecticidal Crystal Proteins of *Bacillus thuringiensis*." *Microbiol. Rev.* 53:242-255.
Wu et al. 1992. "Localized mutagenesis defines regions of the *Bacillus thuringiensis* delta-endotoxin involved in toxicity and specificity." *J. Biol. Chem.* 267:2311-2317.
Dame et al. 1996. "Current status of the *Plasmodium falciparum* genome project." *Mol. Biochem. Parasitol.* 79: 1-12.
Benter et al. 2001. "DNA microarrays with PAMAM dendritic linker systems." *Nucleic Acids Res.* 30: 1-7 of E10.
Dedhia et al., 1997. "Design of expression system for metabolic engineering: coordinated synthesis and degradation of glycogen." *Biotech. Bioengineer* 55: 419-426.

* cited by examiner

*Primary Examiner*—Anne R Kubelik
(74) *Attorney, Agent, or Firm*—Timothy K. Ball, Esq.; Howrey LLP

(57) ABSTRACT

Disclosed are *Bacillus thuringiensis* strains comprising novel crystal proteins which exhibit insecticidal activity against lepidopteran insects. Also disclosed are novel *B. thuringiensis* genes and their encoded crystal proteins, as well as methods of making and using transgenic cells comprising the novel nucleic acid sequences of the invention.

19 Claims, No Drawings

PLANT TRANSFORMED WITH POLYNUCLEOTIDE ENCODING LEPIDOPTERAN-ACTIVE *BACILLUS THURINGIENSIS* δ-ENDOTOXIN

This application is a divisional of application Ser. No. 10/428,961, filed May 2, 2003, now U.S. Pat. No. 7,078,509, which is a divisional of application Ser. No. 09/661,322, filed Sep. 13, 2000, now U.S. Pat. No. 6,593,293, which claims the benefit of priority from U.S. Provisional Application No. 60/153,995, filed Sep. 15, 1999, the entire contents of each is hereby specifically incorporated by reference.

1.0 BACKGROUND OF THE INVENTION

1.1 Field of the Invention

The present invention relates generally to the fields of molecular biology. More particularly, certain embodiments concern methods and compositions comprising DNA segments, and proteins derived from bacterial species. More particularly, it concerns novel genes from *Bacillus thuringiensis* encoding lepidopteran-toxic crystal proteins. Various methods for making and using these DNA segments, DNA segments encoding synthetically-modified Cry proteins, and native and synthetic crystal proteins are disclosed, such as, for example, the use of DNA segments as diagnostic probes and templates for protein production, and the use of proteins, fusion protein carriers and peptides in various immunological and diagnostic applications. Also disclosed are methods of making and using nucleic acid segments in the development of transgenic plant cells containing the DNA segments disclosed herein.

1.2 Description of the Related Art

Almost all field crops, plants, and commercial farming areas are susceptible to attack by one or more insect pests. Particularly problematic are Coleopteran and Lepidoptern pests. For example, vegetable and cole crops such as artichokes, kohlrabi, arugula, leeks, asparagus, lentils, beans, lettuce (e.g., head, leaf, romaine), beets, bok choy, malanga, broccoli, melons (e.g., muskmelon, watermelon, crenshaw, honeydew, cantaloupe), brussels sprouts, cabbage, cardoni, carrots, napa, cauliflower, okra, onions, celery, parsley, chick peas, parsnips, chicory, peas, chinese cabbage, peppers, collards, potatoes, cucumber, pumpkins, cucurbits, radishes, dry bulb onions, rutabaga, eggplant, salsify, escarole, shallots, endive, soybean, garlic, spinach, green onions, squash, greens, sugar beets, sweet potatoes, turnip, swiss chard, horseradish, tomatoes, kale, turnips, and a variety of spices are sensitive to infestation by one or more of the following insect pests: alfalfa looper, armyworm, beet armyworm, artichoke plume moth, cabbage budworm, cabbage looper, cabbage webworm, corn earworm, celery leafeater, cross-striped cabbageworm, european corn borer, diamondback moth, green cloverworm, imported cabbageworm, melonworm, omnivorous leafroller, pickleworm, rindworm complex, saltmarsh caterpillar, soybean looper, tobacco budworm, tomato fruitworm, tomato hornworm, tomato pinworm, velvetbean caterpillar, and yellowstriped armyworm. Likewise, pasture and hay crops such as alfalfa, pasture grasses and silage are often attacked by such pests as armyworm, beef armyworm, alfalfa caterpillar, European skipper, a variety of loopers and webworms, as well as yellowstriped armyworms.

Fruit and vine crops such as apples, apricots, cherries, nectarines, peaches, pears, plums, prunes, quince almonds, chestnuts, filberts, pecans, pistachios, walnuts, citrus, blackberries, blueberries, boysenberries, cranberries, currants, loganberries, raspberries, strawberries, grapes, avocados, bananas, kiwi, persimmons, pomegranate, pineapple, tropical fruits are often susceptible to attack and defoliation by achema sphinx moth, amorbia, armyworm, citrus cutworm, banana skipper, blackheaded fireworm, blueberry leafroller, cankerworm, cherry fruitworm, citrus cutworm, cranberry girdler, eastern tent caterpillar, fall webworm, fall webworm, filbert leafroller, filbert webworm, fruit tree leafroller, grape berry moth, grape leaffolder, grapeleaf skeletonizer, green fruitworm, gummosos-batrachedra commosae, gypsy moth, hickory shuckworm, hornworms, loopers, navel orangeworm, obliquebanded leafroller, omnivorous leafroller, omnivorous looper, orange tortrix, orangedog, oriental fruit moth, pandemis leafroller, peach twig borer, pecan nut casebearer, redbanded leafroller, redhumped caterpillar, roughskinned cutworm, saltmarsh caterpillar, spanworm, tent caterpillar, thecla-thecla basillides, tobacco budworm, tortrix moth, tufted apple budmoth, variegated leafroller, walnut caterpillar, western tent caterpillar, and yellowstriped armyworm.

Field crops such as canola/rape seed, evening primrose, meadow foam, corn (field, sweet, popcorn), cotton, hops, jojoba, peanuts, rice, safflower, small grains (barley, oats, rye, wheat, etc.), sorghum, soybeans, sunflowers, and tobacco are often targets for infestation by insects including armyworm, asian and other corn borers, banded sunflower moth, beet armyworm, bollworm, cabbage looper, corn rootworm (including southern and western varieties), cotton leaf perforator, diamondback moth, european corn borer, green cloverworm, headmoth, headworm, imported cabbageworm, loopers (including *Anacamptodes* spp.), obliquebanded leafroller, omnivorous leaftier, podworm, podworm, saltmarsh caterpillar, southwestern corn borer, soybean looper, spotted cutworm, sunflower moth, tobacco budworm, tobacco hornworm, velvetbean caterpillar.

Bedding plants, flowers, ornamentals, vegetables and container stock are frequently fed upon by a host of insect pests such as armyworm, azalea moth, beet armyworm, diamondback moth, ello moth (hornworm), Florida fern caterpillar, Io moth, loopers, oleander moth, omnivorous leafroller, omnivorous looper, and tobacco budworm.

Forests, fruit, ornamental, and nut-bearing trees, as well as shrubs and other nursery stock are often susceptible to attack from diverse insects such as bagworm, blackheaded budworm, browntail moth, california oakworm, douglas fir tussock moth, elm spanworm, fall webworm, fruittree leafroller, greenstriped mapleworm, gypsy moth, jack pine budworm, mimosa webworm, pine butterfly, redhumped caterpillar, saddleback caterpillar, saddle prominent caterpillar, spring and fall cankerworm, spruce budworm, tent caterpillar, tortrix, and western tussock moth. Likewise, turf grasses are often attacked by pests such as armyworm, sod webworm, and tropical sod webworm.

Because crops of commercial interest are often the target of insect attack, environmentally-sensitive methods for controlling or eradicating insect infestation are desirable in many instances. This is particularly true for farmers, nurserymen, growers, and commercial and residential areas which seek to control insect populations using eco-friendly compositions.

The most widely used environmentally-sensitive insecticidal formulations developed in recent years have been composed of microbial pesticides derived from the bacterium *Bacillus thuringiensis*. *B. thuringiensis* is a Gram-positive bacterium that produces crystal proteins or inclusion bodies which are specifically toxic to certain orders and species of insects. Many different strains of *B. thuringiensis* have been shown to produce insecticidal crystal proteins. Compositions including *B. thuringiensis* strains which produce insecticidal proteins have been commercially-available and used as environmentally-acceptable insecticides because they are quite toxic to the specific target insect, but are harmless to plants and other non-targeted organisms.

1.2.1 *B. Thuringiensis* Crystal Proteins 1.2.1 δ-Endotoxins

δ-endotoxins are used to control a wide range of leaf-eating caterpillars and beetles, as well as mosquitoes. These proteinaceous parasporal crystals, also referred to as insecticidal crystal proteins, crystal proteins, Bt inclusions, crystalline inclusions, inclusion bodies, and Bt toxins, are a large collection of insecticidal proteins produced by *B. thuringiensis* that are toxic upon ingestion by a susceptible insect host. Over the past decade research on the structure and function of *B. thuringiensis* toxins has covered all of the major toxin categories, and while these toxins differ in specific structure and function, general similarities in the structure and function are assumed. Based on the accumulated knowledge of *B. thuringiensis* toxins, a generalized mode of action for *B. thuringiensis* toxins has been created and includes: ingestion by the insect, solubilization in the insect midgut (a combination stomach and small intestine), resistance to digestive enzymes sometimes with partial digestion actually "activating" the toxin, binding to the midgut cells, formation of a pore in the insect cells and the disruption of cellular homeostasis (English and Slatin, 1992).

One of the unique features of *B. thuringiensis* is its production of crystal proteins during sporulation which are specifically toxic to certain orders and species of insects. Many different strains of *B. thuringiensis* have been shown to produce insecticidal crystal proteins. Compositions including *B. thuringiensis* strains which produce proteins having insecticidal activity against lepidopteran and dipteran insects have been commercially available and used as environmentally-acceptable insecticides because they are quite toxic to the specific target insect, but are harmless to plants and other non-targeted organisms.

The mechanism of insecticidal activity of the *B. thuringiensis* crystal proteins has been studied extensively in the past decade. It has been shown that the crystal proteins are toxic to the insect only after ingestion of the protein by the insect. The alkaline pH and proteolytic enzymes in the insect mid-gut solubilize the proteins, thereby allowing the release of components which are toxic to the insect. These toxic components disrupt the mid-gut cells, cause the insect to cease feeding, and, eventually, bring about insect death. For this reason, *B. thuringiensis* has proven to be an effective and environmentally safe insecticide in dealing with various insect pests.

As noted by Höfte and Whiteley (1989), the majority of insecticidal *B. thuringiensis* strains are active against insects of the order Lepidoptera, i.e., caterpillar insects. Other *B. thuringiensis* strains are insecticidally active against insects of the order Diptera, i.e., flies and mosquitoes, or against both lepidopteran and dipteran insects. In recent years, a few *B. thuringiensis* strains have been reported as producing crystal proteins that are toxic to insects of the order Coleoptera, i.e., beetles (Krieg et al., 1983; Sick et al., 1990; Donovan et al., 1992; Lambert et al., 1992a; 1992b).

1.2.2 Genes Encoding Crystal Proteins

Many of the δ-endotoxins are related to various degrees by similarities in their amino acid sequences. Historically, the proteins and the genes which encode them were classified based largely upon their spectrum of insecticidal activity. The review by Höfte and Whiteley (1989) discusses the genes and proteins that were identified in *B. thuringiensis* prior to 1990, and sets forth the nomenclature and classification scheme which has traditionally been applied to *B. thuringiensis* genes and proteins. cryI genes encode lepidopteran-toxic CryI proteins. cryII genes encode CryII proteins that are toxic to both lepidopterans and dipterans. cryIII genes encode coleopteran-toxic CryIII proteins, while cryIV genes encode dipteran-toxic CryIV proteins. Based on the degree of sequence similarity, the proteins were further classified into subfamilies; more highly related proteins within each family were assigned divisional letters such as CryIA, CryIB, CryIC, etc. Even more closely related proteins within each division were given names such as CryIC1, CryIC2, etc.

Recently, a new nomenclature was developed which systematically classified the Cry proteins based upon amino acid sequence homology rather than upon insect target specificities (Crickmore et al., 1998). The classification scheme for many known toxins, including allelic variations in individual proteins, is summarized and regularly updated at http://www.biols.susx.ac.uk/Home/Neil_Crickmore/Bt/. The informationw was most recently updated as of Apr. 27, 1999 and is herein incorporated by reference.

1.2.3 Crystal Proteins Toxic to Lepidopteran Insects 2.0 SUMMARY OF THE INVENTION The recent review by Schnepf et al. (1998) describes the enormous diversity of insecticidal crystal proteins derived from *B. thuringiensis*. Cry proteins of the Cry1, Cry2, and Cry9 classes are particularly known for their toxicity towards lepidopteran larvae, however, the degree of toxicity varies significantly depending on the target lepidopteran pest (Höfte and Whiteley, 1989). For instance, Cry1Ac shows poor toxicity towards the armyworm, *Spodoptera littoralis*, but strong toxicity towards the tobacco budworm, *Heliothis virescens*. In addition, slight variations in amino acid sequence within a Cry protein class can dramatically impact insecticidal activity (see Schnepf et al., 1998 and references therein). The Cry3Ba and Cry3Bb genes, for instance, share 94% amino acid sequence identity, but only Cry3Bb exhibits significant toxicity towards the Southern corn rootwom, *Diabrotica undecimpunctata howardi* (Donovan et al., 1992). Similarly, Cry2Aa and Cry2Ab share 87% amino acid sequence identity, yet only Cry2Aa displays toxicity towards mosquitos (Widner and Whiteley, 1990). Von Tersch et al. (1991) demonstrated that Cry1Ac proteins varying by only seven amino acids (>99% sequence identity) nevertheless show significant differences in insecticidal activity. Lee et al. (1996) reported that Cry1Ab alleles differing at only two amino acid positions exhibited a 10-fold difference in toxicity towards the gypsy moth, *Lymantria dispar*. Thus, even Cry proteins that are considered to be alleles of known Cry proteins or to belong to a Cry protein subclass (Crickmore et al., 1998) may have unique and useful insecticidal properties. International Patent Application Publication No. WO 98/00546 and WO 98/40490 describe a variety of Cry1-, Cry2-, and Cry9-related crystal proteins obtained from *B. thuringiensis*.

2.1 Cry DNA Segments

The present invention concerns nucleic acid segments, that can be isolated from virtually any source, that are free from total genomic DNA and that encode the novel peptides disclosed herein. Nucleic acid segments encoding these polypeptides may encode active proteins, peptides or peptide fragments, polypeptide subunits, functional domains, or the like of one or more crystal proteins. In addition the invention encompasses nucleic acid segments which may be synthesized entirely in vitro using methods that are well-known to those of skill in the art which encode the novel Cry polypeptides, peptides, peptide fragments, subunits, or functional domains disclosed herein.

As used herein, the term "nucleic acid segment" refers to a polynucleotide molecule that has been isolated free of total genomic DNA of a particular species. Therefore, a nucleic acid segment encoding an endotoxin polypeptide refers to a nucleic acid segment that comprises one or more crystal protein-encoding sequences yet is isolated away from, or purified free from, total genomic DNA of the species from which the nucleic acid segment is obtained, which in the instant case is the genome of the Gram-positive bacterial genus, Bacillus, and in particular, the species of Bacillus known as B. thuringiensis. Included within the term "nucleic acid segment", are polynucleotide segments and smaller fragments of such segments, and also recombinant vectors, including, for example, plasmids, cosmids, phagemids, phages, viruses, and the like.

Similarly, a DNA segment comprising an isolated or purified crystal protein-encoding gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes both genomic sequences, operon sequences and smaller engineered gene segments that express, or may be adapted to express, proteins, polypeptides or peptides. Also, the term includes an expression cassette comprising at least a promoter operably linked to one or more protein coding sequences, operably linked to at least a transcriptional termination sequence.

"Isolated substantially away from other coding sequences" means that the gene of interest, in this case, a nucleic acid segment or gene encoding all or part of a bacterial insecticidal crystal protein, forms the significant part of the coding region of the DNA segment, and that the DNA segment does not contain large portions of naturally-occurring coding DNA, such as large chromosomal fragments or other functional nucleic acid segments or genes or operon coding regions. Of course, this refers to the DNA segment as originally isolated, and does not exclude genes, recombinant genes, synthetic linkers, or coding regions later added to the segment by the hand of man.

In particular embodiments, the invention concerns isolated DNA segments and recombinant vectors incorporating DNA sequences that encode a Cry peptide species that includes within its amino acid sequence an amino acid sequence essentially as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50 and SEQ ID NO:63.

The term "a sequence essentially as set forth in SEQ ID NO:2, SEQ ID NO:4, or SEQ ID NO:6," for example, means that the sequence substantially corresponds to a portion of the sequence of SEQ ID NO:2, SEQ ID NO:4, or SEQ ID NO:6 and has relatively few amino acids that are not identical with, or a biologically functional equivalent of, the amino acids of any of these sequences. The term "biologically functional equivalent" is well understood in the art and is further defined in detail herein (e.g., see Illustrative Embodiments). Accordingly, sequences that have from about 70% to about 80%, or more preferably about 81, 82, 83, 84, 85, 86, 87, 88, 89, or about 90%, or even more preferably about 91, 92, 93, 94, 95, 96, 97, 98, or about 99% amino acid sequence identity or functional equivalence to the amino acids of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50 and SEQ ID NO:63 will be sequences that are "essentially as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50 and SEQ ID NO: 63."

In addition, sequences that have from about 70% to about 80%, or more preferably about 81, 82, 83, 84, 85, 86, 87, 88, 89, or about 90%, or even more preferably about 91, 92, 93, 94, 95, 96, 97, 98, or about 99% nucleic acid sequence identity or functional equivalence to the nucleic acids of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49 and SEQ ID NO:62 will be sequences that are "essentially as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49 and SEQ ID NO:62."

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch encoding any of the peptide sequences disclosed in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50 and SEQ ID NO: 63, or that are identical with or complementary to DNA sequences which encode any of the peptides disclosed in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50 and SEQ ID NO: 63, and particularly those DNA segments disclosed in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49 and SEQ ID NO:62. For example, DNA sequences such as about 18 nucleotides, and that are up to about 10,000, about 5,000, about 3,000, about 2,000, about 1,000, about 500, about 200, about 100, about 50, and about 14 base pairs in length (including all intermediate lengths) are also contemplated to be useful.

It will be readily understood that "intermediate lengths", in these contexts, means any length between the quoted ranges, such as 18, 19, 20, 21, 22, 23, etc.; 30, 31, 32, etc.; 50, 51, 52, 53, etc.; 100, 101, 102, 103, etc.; 150, 151, 152, 153, etc.; including all integers in the ranges of from about 200-500; 500-1,000; 1,000-2,000; 2,000-3,000; 3,000-5,000; and up to and including sequences of about 10,00 or so nucleotides and the like.

It will also be understood that this invention is not limited to the particular nucleic acid sequences which encode peptides of the present invention, or which encode the amino acid sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50 and SEQ ID NO: 63, including those DNA sequences which are particularly disclosed in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49 and SEQ ID NO:62. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional, equivalent peptides. Such sequences may arise as a consequence of codon degeneracy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

2.2 Cry DNA Segments as Hybridization Probes and Primers

In addition to their use in directing the expression of crystal proteins or peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49 and SEQ ID NO:62 will find particular utility. Longer contiguous identical or complementary sequences, e.g., those of about 20, 30, 40, 50, 100, 200, 500, 1000, 2000, 5000 bp, etc. (including all intermediate lengths and up to and including the full-length gene sequences encoding each polypeptide will also be of use in certain embodiments.

The ability of such nucleic acid probes to specifically hybridize to crystal protein-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of about 14 to about 17 or so, 18-25, 26-35, 36-50, or even up to and including sequences of about 100-200 nucleotides or so, identical or complementary to DNA sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49 and SEQ ID NO:62, are particularly contemplated as hybridization probes for use in, e.g., Southern and Northern blotting. Smaller fragments will generally find use in hybridization embodiments, wherein the length of the contiguous complementary region may be varied, such as between about 10-14 and about 100 to 200 or so nucleotides, but larger contiguous complementarity stretches may be used, according to the length complementary sequences one wishes to detect.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating crystal protein-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1990; Maloy 1994; Segal, 1976; Prokop, 1991; and Kuby, 1991, are particularly relevant.

Of course, for some applications, for example, where one desires to prepare mutants employing a mutant primer strand hybridized to an underlying template or where one seeks to isolate crystal protein-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

2.3 Vectors and Methods for Recombinant Expression of Cry Polypeptides

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a crystal protein or peptide in its natural environment. Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the *Pichia* expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of crystal peptides or epitopic core regions, such as may be used to generate anti-crystal protein antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequences from SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50 and SEQ ID NO: 63.

2.4 Cry Transgenes and Transgenic Plants Expressing Cry Polypeptides

In yet another aspect, the present invention provides methods for producing a transgenic plant which expresses a nucleic acid segment encoding the novel polypeptides and endotoxins of the present invention. The process of producing transgenic plants is well-known in the art. In general, the method comprises transforming a suitable host cell with a DNA segment which contains a promoter operatively linked to a coding region that encodes one or more CryET31, CryET40, CryET43, CryET44, CryET45, CryET46, CryET47, CryET49, CryET51, CryET52, CryET53, CryET54, CryET55, CryET56, CryET57, CryET59, CryET60, CryET61, CryET62, CryET63, CryET64, CryET66, CryET67, CryET68, CryET72, CryET73, and CryET83 polypeptides. Such a coding region is generally operatively linked to a transcription-terminating region, whereby the promoter is capable of driving the transcription of the coding region in the cell, and hence providing the cell the ability to produce the polypeptide in vivo. Alternatively, in instances where it is desirable to control, regulate, or decrease the amount of a particular recombinant crystal protein expressed in a particular transgenic cell, the invention also provides for the expression of crystal protein antisense mRNA. The use of antisense mRNA as a means of controlling or decreasing the amount of a given protein of interest in a cell is well-known in the art.

Another aspect of the invention comprises transgenic plants which express a gene or gene segment encoding one or more of the novel polypeptide compositions disclosed herein. As used herein, the term "transgenic plant" is intended to refer to a plant that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances either the nuclear or plastidic genome, or both, of a transgenic plant of the present invention will have been augmented through the stable introduction of one or more cryET31, cryET40, cryET43, cryET44, cryET45, cryET46, cryET47, cryET49, cryET51, cryET52, cryET53, cryET54, cryET55, cryET56, cryET57, cryET59, cryET60, cryET61, cryET62, cryET63, cryET64, cryET66, cryET67, cryET68, cryET72, cryET73, and cryET83 transgenes, either native, synthetically modified, or mutated. In some instances, more than one transgene will be incorporated into one or more genomes of the transformed host plant cell. Such is the case when more than one crystal protein-encoding DNA segment is incorporated into the genome of such a plant. In certain situations, it may be desirable to have one, two, three, four, or even more *B. thuringiensis* crystal proteins (either native or recombinantly-engineered) incorporated and stably expressed in the transformed transgenic plant.

A preferred gene which may be introduced includes, for example, a crystal protein-encoding DNA sequence from bacterial origin, and particularly one or more of those described herein which are obtained from *Bacillus* spp. Highly preferred nucleic acid sequences are those obtained from *B. thuringiensis*, or any of those sequences which have been genetically engineered to decrease or increase the insecticidal activity of the crystal protein in such a transformed host cell.

Means for transforming a plant cell and the preparation of a transgenic cell line are well-known in the art, and are discussed herein. Vectors, plasmids, cosmids, YACs (yeast artificial chromosomes) and DNA segments for use in transforming such cells will, of course, generally comprise either the operons, genes, or gene-derived sequences of the present invention, either native, or synthetically-derived, and particularly those encoding the disclosed crystal proteins. These DNA constructs can further include structures such as promoters, enhancers, polylinkers, or even gene sequences which have positively- or negatively-regulating activity upon the particular genes of interest as desired. The DNA segment or gene may encode either a native or modified crystal protein, which will be expressed in the resultant recombinant cells, and/or which will impart an improved phenotype to the regenerated plant.

Such transgenic plants may be desirable for increasing the insecticidal resistance of a monocotyledonous or dicotyledonous plant, by incorporating into such a plant, a transgenic DNA segment encoding one or more CryET31, CryET40, CryET43, CryET44, CryET45, CryET46, CryET47, CryET49, CryET51, CryET52, CryET53, CryET54, CryET55, CryET56, CryET57, CryET59, CryET60, CryET61, CryET62, CryET63, CryET64, CryET66, CryET67, CryET68, CryET72, CryET73, and CryET83 polypeptides which are toxic to a lepidopteran insect. Particularly preferred plants include turf grasses, kapok, sorghum, cotton, corn, soybeans, oats, rye, wheat, flax, tobacco, rice, sugarcanes, tomatoes, potatoes, barley, pasture grass, berry fruit, legume, or other vegetables, ornamental plants, shrub, cactus, succulent, trees, and the like.

In a related aspect, the present invention also encompasses a seed produced by the transformed plant, a progeny from such seed, and a seed produced by the progeny of the original transgenic plant, produced in accordance with the above process. Such progeny and seeds will have a crystal protein-encoding transgene stably incorporated into their genome, and such progeny plants will inherit the traits afforded by the introduction of a stable transgene in Mendelian fashion. All such transgenic plants having incorporated into their genome transgenic DNA segments encoding one or more CryET31, CryET40, CryET43, CryET44, CryET45, CryET46, CryET47, CryET49, CryET51, CryET52, CryET53, CryET54, CryET55, CryET56, CryET57, CryET59, CryET60, CryET61, CryET62, CryET63, CryET64, CryET66, CryET67, CryET68, CryET72, CryET73, and CryET83 crystal proteins or polypeptides are aspects of this invention. As well-known to those of skill in the art, a progeny of a plant is understood to mean any offspring or any descendant from such a plant, but in this case means any offspring or any descendant which also contains the transgene.

2.5 Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. The technique of site-specific mutagenesis is well known in the art, as exemplified by various publications.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the endotoxin-encoding nucleic acid segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

2.6 Antibody Compositions and Methods of Making

In particular embodiments, the inventors contemplate the use of antibodies, either monoclonal (mAbs) or polyclonal which bind to one or more of the polypeptides disclosed herein. Means for preparing and characterizing antibodies are well known in the art (See, e.g., Harlow and Lane, 1988; incorporated herein by reference). mAbs may be readily prepared through use of well-known techniques, such as those exemplified in U.S. Pat. No. 4,196,265, incorporated herein by reference.

2.7 ELISAS and Immunoprecipitation

ELISAs may be used in conjunction with the invention. Many different protocols exist for performing ELISAs. These are well known to those of ordinary skill in the art. Examples of basic ELISA protocols may be found in any standard molecular biology laboratory manual (e.g. Sambrook, Fritsch, and Maniatis, eds. Molecular cloning: a laboratory manual. Cold Spring Harbor, N.Y.: Cold Spring Harbor Laboratory, 1989).

2.8 Western Blots

The compositions of the present invention will find great use in immunoblot or western blot analysis. Methods of performing immunoblot and western blot analysis are well known to those of skill in the are (see Sambrook, et al., ibid). Immunologically-based detection methods for use in conjunction with Western blotting include enzymatically-, radiolabel-, or fluorescently-tagged secondary antibodies against the toxin moiety are considered to be of particular use in this regard.

2.9 Crystal Protein Screening and Detection Kits

The present invention contemplates methods and kits for screening samples suspected of containing crystal protein polypeptides or crystal protein-related polypeptides, or cells producing such polypeptides. A kit may contain one or more antibodies of the present invention, and may also contain reagent(s) for detecting an interaction between a sample and an antibody of the present invention. The provided reagent(s) can be radio-, fluorescently- or enzymatically-labeled or even epitope or ligand tagged. The kit can contain a known radio-labeled agent capable of binding or interacting with a nucleic acid or antibody of the present invention.

The reagent(s) of the kit can be provided as a liquid solution, attached to a solid support or as a dried powder. Preferably, when the reagent(s) are provided in a liquid solution, the liquid solution is an aqueous solution. Preferably, when the reagent(s) provided are attached to a solid support, the solid support can be chromatograph media, a test plate having a plurality of wells, or a microscope slide. When the reagent(s) provided are a dry powder, the powder can be reconstituted by the addition of a suitable solvent, that may be provided.

In still further embodiments, the present invention concerns immunodetection methods and associated kits. It is proposed that the crystal proteins or peptides of the present invention may be employed to detect antibodies having reactivity therewith, or, alternatively, antibodies prepared in accordance with the present invention, may be employed to detect crystal proteins or crystal protein-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. One may find additional advantages through the use of a secondary binding ligand such as a second antibody or a biotin/avidin ligand binding arrangement, as is known in the art.

For assaying purposes, it is proposed that virtually any sample suspected of comprising either a crystal protein or peptide or a crystal protein-related peptide or antibody sought to be detected, as the case may be, may be employed. It is contemplated that such embodiments may have application in the tittering of antigen or antibody samples, in the selection of hybridomas, and the like. In related embodiments, the present invention contemplates the preparation of kits that may be employed to detect the presence of crystal proteins or related peptides and/or antibodies in a sample. Samples may include cells, cell supernatants, cell suspensions, cell extracts, enzyme fractions, protein extracts, or other cell-free compositions suspected of containing crystal proteins or peptides.

Generally speaking, kits in accordance with the present invention will include a suitable crystal protein, peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquoted. The kits of the present invention will also typically include a means for containing the antibody, antigen, and reagent containers in close confinement for commercial sale. Such containers may include injection or blow-molded plastic containers into which the desired vials are retained.

2.10 Epitopic Core Sequences

The present invention is also directed to protein or peptide compositions, free from total cells and other peptides, which comprise a purified protein or peptide which incorporates an epitope that is immunologically cross-reactive with one or more anti-crystal protein antibodies. In particular, the invention concerns epitopic core sequences derived from Cry proteins or peptides.

As used herein, the term "incorporating an epitope(s) that is immunologically cross-reactive with one or more anti-crystal protein antibodies" is intended to refer to a peptide or protein antigen which includes a primary, secondary or tertiary structure similar to an epitope located within a crystal protein or polypeptide. The level of similarity will generally be to such a degree that monoclonal or polyclonal antibodies directed against the crystal protein or polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art. The identification of Cry immunodominant epitopes, and/or their functional equivalents, suitable for use in vaccines is a relatively straightforward matter (e.g. U.S. Pat. No. 4,554,101; Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 8 to about 20 amino acids in length, and more preferably about 8 to about 15 amino acids in length. It is proposed that particular advantages of the present invention may be realized through the preparation of synthetic peptides which include modified and/or extended epitopic/immunogenic core sequences which result in a "universal" epitopic peptide directed to crystal proteins, and in particular CryET31, CryET40, CryET43, CryET44, CryET45, CryET46, CryET47, CryET49, CryET51, CryET52, CryET53, CryET54, CryET55, CryET56, CryET57, CryET59, CryET60, CryET61, CryET62, CryET63, CryET64, CryET66, CryET67, CryET68, CryET72, CryET73, CryET83 and related sequences. These epitopic core sequences are identified herein in particular aspects as hydrophilic regions of the particular polypeptide antigen.

Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer).

2.11 Biological Functional Equivalents

Modification and changes may be made in the structure of the peptides of the present invention and DNA segments which encode them and still obtain a functional molecule that encodes a protein or peptide with desirable characteristics.

The following is a discussion based upon changing the amino acids of a protein to create an equivalent, or even an improved, second-generation molecule. In particular embodiments of the invention, mutated crystal proteins are contemplated to be useful for increasing the insecticidal activity of the protein, and consequently increasing the insecticidal activity and/or expression of the recombinant transgene in a plant cell. The amino acid changes may be achieved by changing the codons of the DNA sequence, according to the codons given in Table 1.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−1.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0 ±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

2.12 Insecticidal Compositions and Methods of Use

The inventors contemplate that the crystal protein compositions disclosed herein will find particular utility as insecticides for topical and/or systemic application to field crops, grasses, fruits and vegetables, and ornamental plants. In a preferred embodiment, the bioinsecticide composition comprises an oil flowable suspension of bacterial cells which expresses a novel crystal protein disclosed herein. Preferably the cells are *B. thuringiensis* NRRL B-21921, NRRL B-21922, NRRL B-21923, NRRL B-21924, NRRL B-21925, NRRL B-21926, NRRL B-21927, NRRL B-21928, NRRL B-21929, NRRL B-21930, NRRL B-21931, NRRL B-21932, NRRL B-21933, NRRL B-21934, NRRL B-21935, NRRL B-21936, NRRL B-21937, NRRL B-21938, NRRL B-21939, NRRL B-21940, NRRL B-21941, NRRL B-21942, NRRL B-21943, and NRRL B-21944, however, any such bacterial host cell expressing the novel nucleic acid segments disclosed herein and producing a crystal protein is contemplated to be useful, such as *B. thuringiensis, B. megaterium, B. subtilis, E. coli*, or *Pseudomonas* spp.

In another important embodiment, the bioinsecticide composition comprises a water dispersible granule. This granule comprises bacterial cells which expresses a novel crystal protein disclosed herein. Preferred bacterial cells are *B. thuringiensis* NRRL B-21921, NRRL B-21922, NRRL B-21923, NRRL B-21924, NRRL B-21925, NRRL B-21926, NRRL B-21927, NRRL B-21928, NRRL B-21929, NRRL B-21930, NRRL B-21931, NRRL B-21932, NRRL B-21933, NRRL B-21934, NRRL B-21935, NRRL B-21936, NRRL B-21937, NRRL B-21938, NRRL B-21939, NRRL B-21940, NRRL B-21941, NRRL B-21942, NRRL B-21943, and NRRL B-21944, however, bacteria such as *B. thuringiensis, B. megaterium, B. subtilis, E. coli*, or *Pseudomonas* spp. cells transformed with a DNA segment disclosed herein and expressing the crystal protein are also contemplated to be useful.

In a third important embodiment, the bioinsecticide composition comprises a wettable powder, dust, pellet, or collodial concentrate. This powder comprises bacterial cells which expresses a novel crystal protein disclosed herein. Preferred bacterial cells are *B. thuringiensis* NRRL B-21921, NRRL B-21922, NRRL B-21923, NRRL B-21924, NRRL B-21925, NRRL B-21926, NRRL B-21927, NRRL B-21928, NRRL B-21929, NRRL B-21930, NRRL B-21931, NRRL B-21932, NRRL B-21933, NRRL B-21934, NRRL B-21935, NRRL B-21936, NRRL B-21937, NRRL B-21938, NRRL B-21939, NRRL B-21940, NRRL B-21941, NRRL B-21942, NRRL B-21943, and NRRL B-21944 cells, however, bacteria such as *B. thuringiensis, B. megaterium, B. subtilis, E. coli*, or *Pseudomonas* spp. cells transformed with a DNA segment disclosed herein and expressing the crystal protein are also contemplated to be useful. Such dry forms of the insecticidal compositions may be formulated to dissolve immediately upon wetting, or alternatively, dissolve in a controlled-release, sustained-release, or other time-dependent manner.

In a fourth important embodiment, the bioinsecticide composition comprises an aqueous suspension of bacterial cells such as those described above which express the crystal protein. Such aqueous suspensions may be provided as a concentrated stock solution which is diluted prior to application, or alternatively, as a diluted solution ready-to-apply.

For these methods involving application of bacterial cells, the cellular host containing the crystal protein gene(s) may be grown in any convenient nutrient medium, where the DNA construct provides a selective advantage, providing for a selective medium so that substantially all or all of the cells retain the *B. thuringiensis* gene. These cells may then be harvested in accordance with conventional ways. Alternatively, the cells can be treated prior to harvesting.

When the insecticidal compositions comprise intact *B. thuringiensis* cells expressing the protein of interest, such bacteria may be formulated in a variety of ways. They may be employed as wettable powders, granules or dusts, by mixing with various diluents, inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersants, or polymers.

Alternatively, the novel insecticidal polypeptides may be prepared by native or recombinant bacterial expression systems in vitro and isolated for subsequent field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate crystals and/or spores from bacterial cultures expressing the crystal protein and apply solutions, suspensions, or colloidal preparations of such crystals and/or spores as the active bioinsecticidal composition.

Regardless of the method of application, the amount of the active component(s) is applied at an insecticidally-effective amount, which will vary depending on such factors as, for example, the specific coleopteran insects to be controlled, the specific plant or crop to be treated, the environmental conditions, and the method, rate, and quantity of application of the insecticidally-active composition.

The insecticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, dessicated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, E. coli, inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, E. coli, by homogeneously mixing, blending and/or grinding the insecticidal composition with suitable adjuvants using conventional formulation techniques.

The insecticidal compositions of this invention are applied to the environment of the target lepidopteran insect, typically onto the foliage of the plant or crop to be protected, by conventional methods, preferably by spraying. The strength and duration of insecticidal application will be set with regard to conditions specific to the particular pest(s), crop(s) to be treated and particular environmental conditions. The proportional ratio of active ingredient to carrier will naturally depend on the chemical nature, solubility, and stability of the insecticidal composition, as well as the particular formulation contemplated.

Other application techniques, including dusting, sprinkling, soaking, soil injection, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well-known to those of skill in the art.

The insecticidal composition of the invention may be employed in the method of the invention singly or in combination with other compounds, including and not limited to other pesticides. The method of the invention may also be used in conjunction with other treatments such as surfactants, detergents, polymers or time-release formulations. The insecticidal compositions of the present invention may be formulated for either systemic or topical use.

The concentration of insecticidal composition which is used for environmental, systemic, or foliar application will vary widely depending upon the nature of the particular formulation, means of application, environmental conditions, and degree of biocidal activity. Typically, the bioinsecticidal composition will be present in the applied formulation at a concentration of at least about 1% by weight and may be up to and including about 99% by weight. Dry formulations of the polypeptide compositions may be from about 1% to about 99% or more by weight of the protein composition, while liquid formulations may generally comprise from about 1% to about 99% or more of the active ingredient by weight. Formulations which comprise intact bacterial cells will generally contain from about $10^4$ to about $10^7$ cells/mg.

The insecticidal formulation may be administered to a particular plant or target area in one or more applications as needed, with a typical field application rate per hectare ranging on the order of from about 50 g to about 500 g of active ingredient, or of from about 500 g to about 1000 g, or of from about 1000 g to about 5000 g or more of active ingredient.

5.0 DESCRIPTION OF ILLUSTRATIVE EMBODIMENTS

5.1 Some Advantages of the Invention

The use of B. thuringiensis insecticidal crystal protein genes for in planta production of insecticidal proteins, thereby conferring insect resistance on important agronomic plants, is rapidly gaining commercial acceptance in the United States and abroad. The need for new insecticidal traits does not diminish, however, with the successful deployment of a handful of cry genes in plants. Concerns over the potential for insect resistance development, for instance, makes it imperative that an arsenal of insecticidal proteins (i.e. cry genes) be assembled to provide the genetic material necessary for tomorrow's insecticidal traits. In addition, transgenic plants producing a B. thuringiensis Cry protein may still be susceptible to damage from secondary insect pests, thus prompting the search for additional Cry proteins with improved efficacy towards these pests. The B. thuringiensis crystal proteins of the present invention represent a diverse collection of insecticidal proteins, including several that are toxic towards a lepidopteran colony exhibiting resistance to certain types of Cry1 proteins. Bioassays against a wide range of lepidopteran pests confirm that these proteins possess insecticidal activity and, furthermore, that these proteins vary in efficacy against this array of target insects. This variation in the spectrum of insects affected by the toxin proteins suggests differing modes of action that may be important for future insect resistance management strategies. In planta expression of the cry genes of the present invention can confer insect resistance to the host plant as has been demonstrated for other cry genes from B. thuringiensis.

5.2 Probes and Primers

In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected crystal protein gene sequence, e.g., a sequence such as that shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49 and SEQ ID NO:62. The ability of such DNAs and nucleic acid probes to specifically hybridize to a crystal protein-encoding gene sequence lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a crystal protein gene from *B. thuringiensis* using PCR™ technology. Segments of related crystal protein genes from other species may also be amplified by PCR™ using such primers.

To provide certain of the advantages in accordance with the present invention, a preferred nucleic acid sequence employed for hybridization studies or assays includes sequences that are complementary to at least a 14 to 30 or so long nucleotide stretch of a crystal protein-encoding sequence, such as that shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49 and SEQ ID NO:62. A size of at least about 14 or so nucleotides in length helps to ensure that the fragment will be of sufficient length to form a duplex molecule that is both stable and selective. Molecules having complementary sequences over stretches greater than about 14 or so bases in length are generally preferred, though, in order to increase stability and selectivity of the hybrid, and thereby improve the quality and degree of specific hybrid molecules obtained. One will generally prefer to design nucleic acid molecules having gene-complementary stretches of about 14 to about 20 or so nucleotides, or even longer where desired. Such fragments may be readily prepared by, for example, directly synthesizing the fragment by chemical means, by application of nucleic acid reproduction technology, such as the PCR™ technology of U.S. Pat. Nos. 4,683,195, and 4,683,202, herein incorporated by reference, or by excising selected DNA fragments from recombinant plasmids containing appropriate inserts and suitable restriction sites.

5.3 Expression Vectors

The present invention contemplates an expression vector comprising a polynucleotide of the present invention. Thus, in one embodiment an expression vector is an isolated and purified DNA molecule comprising a promoter operatively linked to an coding region that encodes a polypeptide of the present invention, which coding region is operatively linked to a transcription-terminating region, whereby the promoter drives the transcription of the coding region.

As used herein, the term "operatively linked" means that a promoter is connected to an coding region in such a way that the transcription of that coding region is controlled and regulated by that promoter. Means for operatively linking a promoter to a coding region are well known in the art.

In a preferred embodiment, the recombinant expression of DNAs encoding the crystal proteins of the present invention is preferable in a *Bacillus* host cell. Preferred host cells include *B. thuringiensis, B. megaterium, B. subtilis*, and related bacilli, with *B. thuringiensis* host cells being highly preferred. Promoters that function in bacteria are well-known in the art. An exemplary and preferred promoter for the *Bacillus* crystal proteins include any of the known crystal protein gene promoters, including the cryET31, cryET40, cryET43, cryET44, cryET45, cryET46, cryET47, cryET49, cryET51, cryET52, cryET53, cryET54, cryET55, cryET56, cryET57, cryET59, cryET60, cryET61, cryET62, cryET63, cryET64, cryET66, cryET67, cryET68, cryET72, cryET73, and cryET83 gene promoters. Alternatively, mutagenized or recombinant crystal protein-encoding gene promoters may be engineered by the hand of man and used to promote expression of the novel gene segments disclosed herein.

In an alternate embodiment, the recombinant expression of DNAs encoding the crystal proteins of the present invention is performed using a transformed Gram-negative bacterium such as an *E. coli* or *Pseudomonas* spp. host cell. Promoters which function in high-level expression of target polypeptides in *E. coli* and other Gram-negative host cells are also well-known in the art.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described (Poszkowski et al., 1989; Odell et al., 1985), and temporally regulated, spatially regulated, and spatio-temporally regulated (Chau et al., 1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue-specific or developmentally specific promoters affecting dicots or monocots.

Where the promoter is a near-constitutive promoter such as CaMV 35S, increases in polypeptide expression are found in a variety of transformed plant tissues (e.g., callus, leaf, seed and root). Alternatively, the effects of transformation can be directed to specific plant tissues by using plant integrating vectors containing a tissue-specific promoter.

An exemplary tissue-specific promoter is the lectin promoter, which is specific for seed tissue. The Lectin protein in soybean seeds is encoded by a single gene (Le1) that is only expressed during seed maturation and accounts for about 2 to about 5% of total seed mRNA. The lectin gene and seed-specific promoter have been fully characterized and used to direct seed specific expression in transgenic tobacco plants (Vodkin et al., 1983; Lindstrom et al., 1990.)

An expression vector containing a coding region that encodes a polypeptide of interest is engineered to be under control of the lectin promoter and that vector is introduced into plants using, for example, a protoplast transformation method (Dhir et al., 1991). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (Van Tunen et al., 1988), bean glycine rich protein 1 (Keller et al., 1989), CaMV 35s transcript (Odell et al., 1985) and Potato patatin (Wenzler et al., 1989). Preferred promoters include a cauliflower mosaic virus (CaMV 35S) promoter, a S-E9 small subunit RuBP carboxylase promoter, a rice actin promoter, a maize histone promoter, a fused CaMV 35S-*Arabidopsis* histone promoter, a CaMV 35S promoter, a CaMV 19S promoter, a nos promoter, an Adh promoter, an actin promoter, a histone promoter, a ribulose bisphosphate carboxylase promoter, an R-allele promoter, a root cell promoter, an α-tubulin promoter, an ABA-inducible promoter, a turgor-inducible promoter, a rbcS promoter, a corn sucrose synthetase 1 promoter, a corn alcohol dehydrogenase 1 promoter, a corn light harvesting complex promoter, a corn heat shock protein promoter, a pea small subunit RuBP carboxylase promoter, a Ti plasmid mannopine synthase promoter, a Ti plasmid nopaline synthase promoter, a petunia chalcone isomerase promoter, a bean glycine rich protein 1 promoter, a CaMV 35S transcript promoter, a potato patatin promoter, a cab promoter, a PEP-Carboxylase promoter and an S-E9 small subunit RuBP carboxylase promoter.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens* described (Rogers et al., 1987). However, several other plant integrating vector systems are known to function in plants including pCaMVCN transfer control vector described (Fromm et al., 1985). Plasmid pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II (nptII) and nopaline synthase 3' non-translated region described (Rogers et al., 1988).

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to confer insecticidal activity to a cell is preferably a CryET31, CryET40, CryET43, CryET44, CryET45, CryET46, CryET47, CryET49, CryET51, CryET52, CryET53, CryET54, CryET55, CryET56, CryET57, CryET59, CryET60, CryET61, CryET62, CryET63, CryET64, CryET66, CryET67, CryET68, CryET72, CryET73, and CryET83 polypeptide-encoding gene.

5.7 Nomenclature of the Novel Polypeptides

The inventors have arbitrarily assigned the designation CryET31, CryET40, CryET43, CryET44, CryET45, CryET46, CryET47, CryET49, CryET51, CryET52, CryET53, CryET54, CryET56, CryET57, CryET59, CryET60, CryET61, CryET62, CryET63, CryET64, CryET66, CryET67, CryET68, CryET72, CryET73, and CryET83 to the polypeptides of this invention. Likewise, the arbitrary designations of cryET31, cryET40, cryET43, cryET44, cryET45, cryET46, cryET47, cryET49, cryET5, cryET52, cryET53, cryET54, cryET56, cryET57, cryET59, cryET60, cryET61, cryET62, cryET63, cryET64, cryET66, cryET67, cryET68, cryET72, cryET73, and cryET83 have been assigned to the novel nucleic acid sequence which encodes these polypeptides, respectively. Formal assignment of gene and protein designations based on the revised nomenclature of crystal protein endotoxins will be assigned by a committee on the nomenclature of *B. thuringiensis*, formed to systematically classify *B. thuringiensis* crystal proteins. The inventors contemplate that the arbitrarily assigned designations of the present invention will be superceded by the official nomenclature assigned to these sequences.

5.8 Transformed Host Cells and Transgenic Plants

Methods and compositions for transforming a bacterium, a yeast cell, a plant cell, or an entire plant with one or more expression vectors comprising a crystal protein-encoding gene segment are further aspects of this disclosure. A transgenic bacterium, yeast cell, plant cell or plant derived from such a transformation process or the progeny and seeds from such a transgenic plant are also further embodiments of the invention.

Means for transforming bacteria and yeast cells are well known in the art. Typically, means of transformation are similar to those well known means used to transform other bacteria or yeast such as *E. coli* or *Saccharomyces cerevisiae*. Methods for DNA transformation of plant cells include *Agrobacterium*-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as by *Agrobacterium* infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973; Zatloukal et al., 1992); (2) physical methods such as microinjection (Capecchi, 1980), electroporation (Wong and Neumann, 1982; Fromm et al., 1985; U.S. Pat. No. 5,384,253) and the gene gun (Johnston and Tang, 1994; Fynan et al., 1993); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992).

5.8.3 Agrobacterium-Mediated Transfer

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described (Fraley et al., 1985; Rogers et al., 1987). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern Agrobacterium transformation vectors are capable of replication in E. coli as well as Agrobacterium, allowing for convenient manipulations as described (Klee et al., 1985). Moreover, recent technological advances in vectors forAgrobacterium-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

Agrobacterium-mediated transformation of leaf disks and other tissues such as cotyledons and hypocotyls appears to be limited to plants that Agrobacterium naturally infects. Agrobacterium-mediated transformation is most efficient in dicotyledonous plants. Few monocots appear to be natural hosts for Agrobacterium, although transgenic plants have been produced in asparagus using Agrobacterium vectors as described (Bytebier et al., 1987). Therefore, commercially important cereal grains such as rice, corn, and wheat must usually be transformed using alternative methods. However, as mentioned above, the transformation of asparagus using Agrobacterium can also be achieved (see, for example, Bytebier et al., 1987).

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced carboxylase activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Fromm et al., 1985; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts are described (Fujimura et al., 1985; Toriyama et al., 1986; Yamada et al., 1986; Abdullah et al., 1986).

5.8.4 Other Transformation Methods

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Fromm et al., 1985; Uchimiya et al., 1986; Callis et al., 1987; Marcotte et al., 1988).

Illustrative methods for the regeneration of cereals from protoplasts are described (Fujimura et al., 1985; Toriyama et al., 1986; Yamada et al., 1986; Abdullah et al., 1986).

5.8.5 Gene Expression in Plants

Although great progress has been made in recent years with respect to preparation of transgenic plants which express bacterial proteins such as B. thuringiensis crystal proteins, the results of expressing native bacterial genes in plants are often disappointing. In recent years, however, several potential factors have been implicated as responsible in varying degrees for the level of protein expression from a particular coding sequence. For example, scientists now know that maintaining a significant level of a particular mRNA in the cell is indeed a critical factor. Unfortunately, the causes for low steady state levels of mRNA encoding foreign proteins are many. First, full length RNA synthesis may not occur at a high frequency. This could, for example, be caused by the premature termination of RNA during transcription or due to unexpected mRNA processing during transcription. Second, full length RNA may be produced in the plant cell, but then processed (splicing, polyA addition) in the nucleus in a fashion that creates a nonfunctional mRNA. If the RNA is not properly synthesized, terminated and polyadenylated, it cannot move to the cytoplasm for translation. Similarly, in the cytoplasm, if mRNAs have reduced half lives (which are determined by their primary or secondary sequence) insufficient protein product will be produced. In addition, there is an effect, whose magnitude is uncertain, of translational efficiency on mRNA half-life. In addition, every RNA molecule folds into a particular structure, or perhaps family of structures, which is determined by its sequence. The particular structure of any RNA might lead to greater or lesser stability in the cytoplasm. Structure per se is probably also a determinant of mRNA processing in the nucleus. It is likely that dramatically changing the sequence of an RNA will have a large effect on its folded structure. It is likely that structure per se or particular structural features also have a role in determining RNA stability.

To overcome these limitations in foreign gene expression, researchers have identified particular sequences and signals in RNAs that have the potential for having a specific effect on RNA stability. In certain embodiments of the invention, therefore, there is a desire to optimize expression of the disclosed nucleic acid segments in planta. One particular method of doing so, is by alteration of the bacterial gene to remove sequences or motifs which decrease expression in a transformed plant cell. The process of engineering a coding sequence for optimal expression in planta is often referred to as "plantizing" a DNA sequence.

Particularly problematic sequences are those which are A+T rich. Unfortunately, since *B. thuringiensis* has an A+T rich genome, native crystal protein gene sequences must often be modified for optimal expression in a plant. The sequence motif ATTTA (or AUUUA as it appears in RNA) has been implicated as a destabilizing sequence in mammalian cell mRNA (Shaw and Kamen, 1986). Many short lived mRNAs have A+T rich 3' untranslated regions, and these regions often have the ATTTA sequence, sometimes present in multiple copies or as multimers (e.g., ATTTATTTA . . . ). Shaw and Kamen showed that the transfer of the 3' end of an unstable mRNA to a stable RNA (globin or VA1) decreased the stable RNA's half life dramatically. They further showed that a pentamer of ATTTA had a profound destabilizing effect on a stable message, and that this signal could exert its effect whether it was located at the 3' end or within the coding sequence. However, the number of ATTTA sequences and/or the sequence context in which they occur also appear to be important in determining whether they function as destabilizing sequences. Shaw and Kamen showed that a trimer of ATTTA had much less effect than a pentamer on mRNA stability and a dimer or a monomer had no effect on stability (Shaw and Kamen, 1987). Note that multimers of ATTTA such as a pentamer automatically create an A+T rich region. This was shown to be a cytoplasmic effect, not nuclear. In other unstable mRNAs, the ATTTA sequence may be present in only a single copy, but it is often contained in an A+T rich region. From the animal cell data collected to date, it appears that ATTTA at least in some contexts is important in stability, but it is not yet possible to predict which occurrences of ATTTA are destabilizing elements or whether any of these effects are likely to be seen in plants.

Some studies on mRNA degradation in animal cells also indicate that RNA degradation may begin in some cases with nucleolytic attack in A+T rich regions. It is not clear if these cleavages occur at ATTTA sequences. There are also examples of mRNAs that have differential stability depending on the cell type in which they are expressed or on the stage within the cell cycle at which they are expressed. For example, histone mRNAs are stable during DNA synthesis but unstable if DNA synthesis is disrupted. The 3' end of some histone mRNAs seems to be responsible for this effect (Pandey and Marzluff, 1987). It does not appear to be mediated by ATTTA, nor is it clear what controls the differential stability of this mRNA. Another example is the differential stability of IgG mRNA in B lymphocytes during B cell maturation (Genovese and Milcarek, 1988). A final example is the instability of a mutant β-thallesemic globin mRNA. In bone marrow cells, where this gene is normally expressed, the mutant mRNA is unstable, while the wild-type mRNA is stable. When the mutant gene is expressed in HeLa or L cells in vitro, the mutant mRNA shows no instability (Lim et al., 1988). These examples all provide evidence that mRNA stability can be mediated by cell type or cell cycle specific factors. Furthermore this type of instability is not yet associated with specific sequences. Given these uncertainties, it is not possible to predict which RNAs are likely to be unstable in a given cell. In addition, even the ATTTA motif may act differentially depending on the nature of the cell in which the RNA is present. Shaw and Kamen (1987) have reported that activation of protein kinase C can block degradation mediated by ATTTA.

The addition of a polyadenylate string to the 3' end is common to most eukaryotic mRNAs, both plant and animal. The currently accepted view of polyA addition is that the nascent transcript extends beyond the mature 3' terminus. Contained within this transcript are signals for polyadenylation and proper 3' end formation. This processing at the 3' end involves cleavage of the mRNA and addition of polyA to the mature 3' end. By searching for consensus sequences near the polyA tract in both plant and animal mRNAs, it has been possible to identify consensus sequences that apparently are involved in polyA addition and 3' end cleavage. The same consensus sequences seem to be important to both of these processes. These signals are typically a variation on the sequence AATAAA. In animal cells, some variants of this sequence that are functional have been identified; in plant cells there seems to be an extended range of functional sequences (Wickens and Stephenson, 1984; Dean et al., 1986). Because all of these consensus sequences are variations on AATAAA, they all are A+T rich sequences. This sequence is typically found 15 to 20 bp before the polyA tract in a mature mRNA. Studies in animal cells indicate that this sequence is involved in both polyA addition and 3' maturation. Site directed mutations in this sequence can disrupt these functions (Conway and Wickens, 1988; Wickens et al., 1987). However, it has also been observed that sequences up to 50 to 100 bp 3' to the putative polyA signal are also required; i.e., a gene that has a normal AATAAA but has been replaced or disrupted downstream does not get properly polyadenylated (Gil and Proudfoot, 1984; Sadofsky and Alwine, 1984; McDevitt et al., 1984). That is, the polyA signal itself is not sufficient for complete and proper processing. It is not yet known what specific downstream sequences are required in addition to the polyA signal, or if there is a specific sequence that has this function. Therefore, sequence analysis can only identify potential polyA signals.

In naturally occurring mRNAs that are normally polyadenylated, it has been observed that disruption of this process, either by altering the polyA signal or other sequences in the mRNA, profound effects can be obtained in the level of functional mRNA. This has been observed in several naturally occurring mRNAs, with results that are gene-specific so far.

It has been shown that in natural mRNAs proper polyadenylation is important in mRNA accumulation, and that disruption of this process can effect mRNA levels significantly. However, insufficient knowledge exists to predict the effect of changes in a normal gene. In a heterologous gene, it is even harder to predict the consequences. However, it is possible that the putative sites identified are dysfunctional. That is, these sites may not act as proper polyA sites, but instead function as aberrant sites that give rise to unstable mRNAs.

In animal cell systems, AATAAA is by far the most common signal identified in mRNAs upstream of the polyA, but at least four variants have also been found (Wickens and Stephenson, 1984). In plants, not nearly so much analysis has been done, but it is clear that multiple sequences similar to AATAAA can be used. The plant sites in Table 2 called major or minor refer only to the study of Dean et al. (1986) which analyzed only three types of plant gene. The designation of polyadenylation sites as major or minor refers only to the frequency of their occurrence as functional sites in naturally occurring genes that have been analyzed. In the case of plants this is a very limited database. It is hard to predict with any certainty that a site designated major or minor is more or less likely to function partially or completely when found in a heterologous gene such as those encoding the crystal proteins of the present invention.

TABLE 2

POLYADENYLATION SITES IN PLANT GENES

| | | |
|---|---|---|
| PA | AATAAA | Major consensus site |
| P1A | AATAAT | Major plant site |
| P2A | AACCAA | Minor plant site |
| P3A | ATATAA | " |
| P4A | AATCAA | " |
| P5A | ATACTA | " |
| P6A | ATAAAA | " |
| P7A | ATGAAA | " |
| P8A | AAGCAT | " |
| P9A | ATTAAT | " |
| P10A | ATACAT | " |
| P11A | AAAATA | " |
| P12A | ATTAAA | Minor animal site |
| P13A | AATTAA | " |
| P14A | AATACA | " |
| P15A | CATAAA | " |

The present invention provides a method for preparing synthetic plant genes which genes express their protein product at levels significantly higher than the wild-type genes which were commonly employed in plant transformation heretofore. In another aspect, the present invention also provides novel synthetic plant genes which encode non-plant proteins.

As described above, the expression of native *B. thuringiensis* genes in plants is often problematic. The nature of the coding sequences of *B. thuringiensis* genes distinguishes them from plant genes as well as many other heterologous genes expressed in plants. In particular, *B. thuringiensis* genes are very rich (~62%) in adenine (A) and thymine (T) while plant genes and most other bacterial genes which have been expressed in plants are on the order of 45-55% A+T.

Due to the degeneracy of the genetic code and the limited number of codon choices for any amino acid, most of the "excess" A+T of the structural coding sequences of some *Bacillus* species are found in the third position of the codons. That is, genes of some *Bacillus* species have A or T as the third nucleotide in many codons. Thus A+T content in part can determine codon usage bias. In addition, it is clear that genes evolve for maximum function in the organism in which they evolve. This means that particular nucleotide sequences found in a gene from one organism, where they may play no role except to code for a particular stretch of amino acids, have the potential to be recognized as gene control elements in another organism (such as transcriptional promoters or terminators, polyA addition sites, intron splice sites, or specific mRNA degradation signals). It is perhaps surprising that such misread signals are not a more common feature of heterologous gene expression, but this can be explained in part by the relatively homogeneous A+T content (~50%) of many organisms. This A+T content plus the nature of the genetic code put clear constraints on the likelihood of occurrence of any particular oligonucleotide sequence. Thus, a gene from *E. coli* with a 50% A+T content is much less likely to contain any particular A+T rich segment than a gene from *B. thuringiensis*.

Typically, to obtain high-level expression of the S-endotoxin genes in plants, existing structural coding sequence ("structural gene") which codes for the S-endotoxin are modified by removal of ATTTA sequences and putative polyadenylation signals by site directed mutagenesis of the DNA comprising the structural gene. It is most preferred that substantially all the polyadenylation signals and ATTTA sequences are removed although enhanced expression levels are observed with only partial removal of either of the above identified sequences. Alternately if a synthetic gene is prepared which codes for the expression of the subject protein, codons are selected to avoid the ATTTA sequence and putative polyadenylation signals. For purposes of the present invention putative polyadenylation signals include, but are not necessarily limited to, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA. In replacing the ATTTA sequences and polyadenylation signals, codons are preferably utilized which avoid the codons which are rarely found in plant genomes.

The selected DNA sequence is scanned to identify regions with greater than four consecutive adenine (A) or thymine (T) nucleotides. The A+T regions are scanned for potential plant polyadenylation signals. Although the absence of five or more consecutive A or T nucleotides eliminates most plant polyadenylation signals, if there are more than one of the minor polyadenylation signals identified within ten nucleotides of each other, then the nucleotide sequence of this region is preferably altered to remove these signals while maintaining the original encoded amino acid sequence.

The second step is to consider the about 15 to about 30 or so nucleotide residues surrounding the A+T rich region identified in step one. If the A+T content of the surrounding region is less than 80%, the region should be examined for polyadenylation signals. Alteration of the region based on polyadenylation signals is dependent upon (1) the number of polyadenylation signals present and (2) presence of a major plant polyadenylation signal.

The extended region is examined for the presence of plant polyadenylation signals. The polyadenylation signals are removed by site-directed mutagenesis of the DNA sequence. The extended region is also examined for multiple copies of the ATTTA sequence which are also removed by mutagenesis.

It is also preferred that regions comprising many consecutive A+T bases or G+C bases are disrupted since these regions are predicted to have a higher likelihood to form hairpin structure due to self-complementarity. Therefore, insertion of heterogeneous base pairs would reduce the likelihood of self-complementary secondary structure formation which are known to inhibit transcription and/or translation in some organisms. In most cases, the adverse effects may be minimized by using sequences which do not contain more than five consecutive A+T or G+C.

5.8.6 Synthetic Oligonucleotides for Mutagenesis

When oligonucleotides are used in the mutagenesis, it is desirable to maintain the proper amino acid sequence and reading frame, without introducing common restriction sites such as BglII, HindIII, SacI, KpnI, EcoRI, NcoI, PstI and SalI into the modified gene. These restriction sites are found in poly-linker insertion sites of many cloning vectors. Of course, the introduction of new polyadenylation signals, ATTTA sequences or consecutive stretches of more than five A+T or G+C, should also be avoided. The preferred size for the oligonucleotides is about 40 to about 50 bases, but fragments ranging from about 18 to about 100 bases have been utilized. In most cases, a minimum of about 5 to about 8 base pairs of homology to the template DNA on both ends of the synthesized fragment are maintained to insure proper hybridization of the primer to the template. The oligonucleotides should avoid sequences longer than five base pairs A+T or G+C. Codons used in the replacement of wild-type codons should preferably avoid the TA or CG doublet wherever possible. Codons are selected from a plant preferred codon table (such as Table 3 below) so as to avoid codons which are rarely found in plant genomes, and efforts should be made to select codons to preferably adjust the G+C content to about 50%.

Regions with many consecutive A+T bases or G+C bases are predicted to have a higher likelihood to form hairpin structures due to self-complementarity. Disruption of these regions by the insertion of heterogeneous base pairs is preferred and should reduce the likelihood of the formation of self-complementary secondary structures such as hairpins which are known in some organisms to inhibit transcription (transcriptional terminators) and translation (attenuators).

Alternatively, a completely synthetic gene for a given amino acid sequence can be prepared, with regions of five or more consecutive A+T or G+C nucleotides being avoided. Codons are selected avoiding the TA and CG doublets in codons whenever possible. Codon usage can be normalized against a plant preferred codon usage table (such as Table 3) and the G+C content preferably adjusted to about 50%. The resulting sequence should be examined to ensure that there are minimal putative plant polyadenylation signals and ATTTA sequences.

TABLE 3

PREFERRED CODON USAGE IN PLANTS

| Amino Acid | Codon | Percent Usage in Plants | Amino Acid | Codon | Percent Usage in Plants |
|---|---|---|---|---|---|
| ARG | CGA | 7 | LEU | CUA | 8 |
| | CGC | 11 | | CUC | 20 |
| | CGG | 5 | | CUG | 10 |
| | CGU | 25 | | CUU | 28 |
| | AGA | 29 | | UUA | 5 |
| | AGG | 23 | | UUG | 30 |
| SER | UCA | 14 | ALA | GCA | 23 |
| | UCC | 26 | | GCG | 32 |
| | UCG | 3 | | GCG | 3 |
| | UCU | 21 | | GCU | 41 |
| | AGC | 21 | GLY | GGA | 32 |
| | AGU | 15 | | GGC | 20 |
| THR | ACA | 21 | | GGG | 11 |
| | ACC | 41 | | GGU | 37 |
| | ACG | 7 | ILE | AUA | 12 |
| | ACU | 31 | | AUC | 45 |
| PRO | CCA | 45 | | AUU | 43 |
| | CCC | 19 | VAL | GUA | 9 |
| | CCG | 9 | | GUC | 20 |
| | CCU | 26 | | GUG | 28 |
| HIS | CAC | 65 | | GUU | 43 |
| | CAU | 35 | LYS | AAA | 36 |
| GLU | GAA | 48 | | AAG | 64 |
| | GAG | 52 | ASN | AAC | 72 |
| ASP | GAC | 48 | | AAU | 28 |
| | GAU | 52 | GLN | CAA | 64 |
| TYR | UAC | 68 | | CAG | 36 |
| | UAU | 32 | PHE | UUC | 56 |
| CYS | UGC | 78 | | UUU | 44 |
| | UGU | 22 | MET | AUG | 100 |
| | | | TRP | UGG | 100 |

Restriction sites found in commonly used cloning vectors are also preferably avoided. However, placement of several unique restriction sites throughout the gene is useful for analysis of gene expression or construction of gene variants.

5.8.7 "Plantized" Gene Constructs

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA. Transcription of DNA into mRNA is regulated by a region of DNA usually referred to as the "promoter." The promoter region contains a sequence of bases that signals RNA polymerase to associate with the DNA and to initiate the transcription of mRNA using one of the DNA strands as a template to make a corresponding strand of RNA.

A number of promoters which are active in plant cells have been described in the literature. These include the nopaline synthase (NOS) and octopine synthase (OCS) promoters (which are carried on tumor-inducing plasmids of *A. tumefaciens*), the Cauliflower Mosaic Virus (CaMV) 19S and 35S promoters, the light-inducible promoter from the small subunit of ribulose bis-phosphate carboxylase (ssRUBISCO, a very abundant plant polypeptide) and the mannopine synthase (MAS) promoter (Velten et al., 1984; Velten and Schell, 1985). All of these promoters have been used to create various types of DNA constructs which have been expressed in plants (see e.g., Intl. Pat. Appl. Publ. Ser. No. WO 84/02913).

Promoters which are known or are found to cause transcription of RNA in plant cells can be used in the present invention. Such promoters may be obtained from plants or plant viruses and include, but are not limited to, the CaMV35S promoter and promoters isolated from plant genes such as ssRUBISCO genes. As described below, it is preferred that the particular promoter selected should be capable of causing sufficient expression to result in the production of an effective amount of protein.

The promoters used in the DNA constructs (i.e. chimeric plant genes) of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis, etc. Furthermore, the promoters may be altered to contain multiple "enhancer sequences" to assist in elevating gene expression.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNA's, from suitable eukaryotic genes, or from a synthetic gene sequence. The present invention is not limited to constructs, as presented in the following examples. Rather, the non-translated leader sequence can be part of the 5' end of the non-translated region of the coding sequence for the virus coat protein, or part of the promoter sequence, or can be derived from an unrelated promoter or coding sequence. In any case, it is preferred that the sequence flanking the initiation site conform to the translational consensus sequence rules for enhanced translation initiation reported by Kozak (1984).

The cry DNA constructs of the present invention may also contain one or more modified or fully-synthetic structural coding sequences which have been changed to enhance the performance of the cry gene in plants. The structural genes of the present invention may optionally encode a fusion protein comprising an amino-terminal chloroplast transit peptide or secretory signal sequence.

The DNA construct also contains a 3' non-translated region. The 3' non-translated region contains a polyadenylation signal which functions in plants to cause the addition of polyadenylate nucleotides to the 3' end of the viral RNA. Examples of suitable 3' regions are (1) the 3' transcribed, non-translated regions containing the polyadenylation signal of *Agrobacterium* tumor-inducing (Ti) plasmid genes, such as the nopaline synthase (NOS) gene, and (2) plant genes like the soybean storage protein (7S) genes and the small subunit of the RuBP carboxylase (E9) gene.

5.9 Methods for Producing Insect-Resistant Transgenic Plants

By transforming a suitable host cell, such as a plant cell, with a recombinant cryET31, cryET40, cryET43, cryET44, cryET45, cryET46, cryET47, cryET49, cryET51, cryET52, cryET53, cryET54, cryET56, cryET57, cryET59, cryET60, cryET61, cryET62, cryET63, cryET64, cryET66, cryET67, cryET68, cryET72, cryET73, and cryET83 gene-containing segment, the expression of the encoded crystal protein (i.e., a bacterial crystal protein or polypeptide having insecticidal activity against coleopterans) can result in the formation of insect-resistant plants.

By way of example, one may utilize an expression vector containing a coding region for a *B. thuringiensis* crystal protein and an appropriate selectable marker to transform a suspension of embryonic plant cells, such as wheat or corn cells using a method such as particle bombardment (Maddock et al., 1991; Vasil et al., 1992) to deliver the DNA coated on microprojectiles into the recipient cells. Transgenic plants are then regenerated from transformed embryonic calli that express the insecticidal proteins.

The formation of transgenic plants may also be accomplished using other methods of cell transformation which are known in the art such as *Agrobacterium*-mediated DNA transfer (Fraley et al., 1983). Alternatively, DNA can be introduced into plants by direct DNA transfer into pollen (Zhou et al., 1983; Hess, 1987; Luo et al., 1988), by injection of the DNA into reproductive organs of a plant (Pena et al., 1987), or by direct injection of DNA into the cells of immature embryos followed by the rehydration of desiccated embryos (Neuhaus et al., 1987; Benbrook et al., 1986).

The regeneration, development, and cultivation of plants from single plant protoplast transformants or from various transformed explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A transgenic plant of this invention thus has an increased amount of a coding region (e.g., a cryET31, cryET40, cryET43, cryET44, cryET45, cryET46, cryET47, cryET49, cryET51, cryET52, cryET53, cryET54, cryET56, cryET57, cryET59, cryET60, cryET61, cryET62, cryET63, cryET64, cryET66, cryET67, cryET68, cryET72, cryET73, and cryET83 gene) that encodes one or more CryET31, CryET40, CryET43, CryET44, CryET45, CryET46, CryET47, CryET49, CryET51, CryET52, CryET53, CryET54, CryET56, CryET57, CryET59, CryET60, CryET61, CryET62, CryET63, CryET64, CryET66, CryET67, CryET68, CryET72, CryET73, and CryET83 polypeptides. A preferred transgenic plant is an independent segregant and can transmit that gene and its activity to its progeny. A more preferred transgenic plant is homozygous for that gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for, by way of example, increased insecticidal capacity against coleopteran insects, preferably in the field, under a range of environmental conditions. The inventors contemplate that the present invention will find particular utility in the creation of transgenic plants of commercial interest including various turf grasses, wheat, corn, rice, barley, oats, a variety of ornamental plants and vegetables, as well as a number of nut- and fruit-bearing trees and plants.

5.10 Definitions

The following words and phrases have the meanings set forth below.

Expression: The combination of intracellular processes, including transcription and translation undergone by a coding DNA molecule such as a structural gene to produce a polypeptide.

Identity or percent identity: refers to the degree of similarity between two nucleic acid or protein sequences. An alignment of the two sequences is performed by a suitable computer program. A widely used and accepted computer program for performing sequence alignments is CLUSTALW v1.6 (Thompson, et al. *Nucl. Acids Res.,* 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g., plant protoplast or explant).

Structural gene: A polynucleotide sequence that encodes a polypeptide, that is expressed to produce a polypeptide, or which is cryptic or incapable of expression in its natural host cell but which can be isolated and purified and operably linked to at least a promoter functional in one or more host cell types to express the encoded polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. A plasmid is an exemplary vector.

5.11 Isolating Homologous Gene and Gene Fragments

The genes and δ-endotoxins according to the subject invention include not only the full length sequences disclosed herein but also fragments of these sequences, or fusion proteins, which retain the characteristic insecticidal activity of the sequences specifically exemplified herein.

It should be apparent to a person skill in this art that insecticidal δ-endotoxins can be identified and obtained through several means. The specific genes, or portions thereof, may be obtained from a culture depository, or constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these δ-endotoxins.

Equivalent δ-endotoxins and/or genes encoding these equivalent δ-endotoxins can also be isolated from *Bacillus* strains and/or DNA libraries using the teachings provided herein. For example, antibodies to the δ-endotoxins disclosed and claimed herein can be used to identify and isolate other δ-endotoxins from a mixture of proteins. Specifically, antibodies may be raised to the portions of the δ-endotoxins which are most constant and most distinct from other *B. thuringiensis* δ-endotoxins. These antibodies can then be used to specifically identify equivalent δ-endotoxins with the characteristic insecticidal activity by immunoprecipitation, enzyme linked immunoassay (ELISA), or Western blotting.

A further method for identifying the δ-endotoxins and genes of the subject invention is through the use of oligonucleotide probes. These probes are nucleotide sequences having a detectable label. As is well known in the art, if the probe molecule and nucleic acid sample hybridize by forming a strong bond between the two molecules, it can be reasonably assumed that the probe and sample are essentially identical. The probe's detectable label provides a means for determining in a known manner whether hybridization has occurred. Such a probe analysis provides a rapid method for identifying formicidal δ-endotoxin genes of the subject invention.

The nucleotide segments which are used as probes according to the invention can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{125}I$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxine, as well as enzymes such as hydrolases or peroxidases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, by methods currently known to an ordinarily skilled artisan, and perhaps by other methods which may become known in the future.

The potential variations in the probes listed is due, in part, to the redundancy of the genetic code. Because of the redundancy of the genetic code, i.e., more than one coding nucleotide triplet (codon) can be used for most of the amino acids used to make proteins. Therefore different nucleotide sequences can code for a particular amino acid. Thus, the amino acid sequences of the B. thuringiensis δ-endotoxins and peptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser and Kezdy, 1984). Thus, the subject invention includes mutants of the amino acid sequence depicted herein which do not alter the protein secondary structure, or if the structure is altered, the biological activity is substantially retained. Further, the invention also includes mutants of organisms hosting all or part of a δ-endotoxin encoding a gene of the invention. Such mutants can be made by techniques well known to persons skilled in the art. For example, UV irradiation can be used to prepare mutants of host organisms. Likewise, such mutants may include asporogenous host cells which also can be prepared by procedures well known in the art.

6.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

6.1 Example 1

Identification of B. Thuringiensis Strains Containing NOVEL δ-Endotoxins

Wild-type B. thuringiensis strains containing novel insecticidal protein genes were identified by Southern blot hybridization studies employing specific DNA probes. Twenty-four unique cry genes were discovered that are related to B. thuringiensis genes in the cry1, cry2, or cry9 classes of toxin genes.

Various methods were employed to clone the novel genes and express them in a crystal protein-negative (Cry-) strain of B. thuringiensis. These methods include PCR™ amplification of the region of cry1-related genes that encodes the active portion of the toxin gene. The PCR™ product is then joined to a fragment from the cry1Ac gene encoding the C-terminal region of the protoxin. This gene fusion was then expressed in a B. thuringiensis recombinant strain to produce a hybrid protoxin. In this instance, it is recognized that the sequence of the amplified DNA can be used to design hybridization probes to isolate the entire coding sequence of the novel cry gene from the wild-type B. thuringiensis strain.

Wild-type B. thuringiensis strains were screened in a bioassay to identify strains that are toxic to larvae of lepidopteran insects (procedure described in Example 10). Active strains were then examined genetically to determine if they contain novel toxin genes. The method used to make this determination is described below and includes isolation of genomic DNA from the B. thuringiensis strain, restriction enzyme digestion, Southern blot hybridization, and analysis of the hybridizing restriction fragments to determine which genes are present in a strain.

Total genomic DNA was extracted by the following procedure. Vegetative cells were resuspended in a lysis buffer containing 50 mM glucose, 25 mM Tris-HCl (pH 8.0), 10 mM EDTA, and 4 mg/ml lysozyme. The suspension was incubated at 37° C. for 1 h. Following incubation, the suspension was extracted once with an equal volume of phenol, then once with an equal volume of phenol:chloroform:isoamyl alcohol (50:48:2), and once with an equal volume of chloroform: isoamyl alcohol (24:1). The DNA was precipitated from the aqueous phase by the addition of one-tenth volume 3 M sodium acetate and two volumes of 100% ethanol. The precipitated DNA was collected by centrifugation, washed with 70% ethanol and resuspended in distilled water.

The DNA samples were digested with the restriction enzymes ClaI and PstI. The combination of these two enzymes give a digestion pattern of fragments that, when hybridized with the probe wd207 (described below), allows the identification of many of the known cry1-related toxin genes. Hybridizing fragments that did not correspond to the fragment sizes expected for the known genes were classified as unknown and were candidates for cloning and characterization.

The digested DNA was size fractionated by electrophoresis through a 1.0% agarose gel in 1×TBE (0.089 M Tris-borate, 0.089 M boric acid, 0.002 M EDTA) overnight at 2 V/cm of gel length. The fractionated DNA fragments were then transferred to a Millipore Immobilon-NC® nitrocellulose filter (Millipore Corp., Bedford, Mass.) according to the method of Southern (1975). The DNA fragments were fixed to the nitocellulose by baking the filter at 80° C. in a vacuum oven.

To identify the DNA fragment(s) containing the sequences related to cry1 genes, the oligonucleotide wd207 was radioactively labeled at the 5' end and used as a hybridization probe. To radioactively label the probe, 1-5 pmoles of wd207 were added to a reaction (20 ul total volume) containing 3 ul [γ-$^{32}$P]ATP (3,000 Ci/mmole at 10 mCi/ml), 70 mM Tris-HCl, pH 7.8, 10 mM MgCl$_2$, 5 mM DTT, and 10 units T4 polynucleotide kinase (Promega Corp., Madison, Wis.). The reaction was incubated for 20 min at 37° C. to allow the transfer of the radioactive phosphate to the 5'-end of the oligonucleotide, thus making it useful as a hybridization probe.

The oligonucleotide probe used in this analysis, designated wd207, has the following sequence:
5'-TGGATACTTGATCAATATGATAATCCGT-CACATCTGTTTTrA-3'(SEQ ID NO: 51)

This oligonucleotide was designed to specifically hybridize to a conserved region of cry1 genes downstream from the proteolyic activation site in the protoxin. Table 4 lists some of the B. thuringiensis toxin genes and their identities with wd207. The orientation of the wd207 sequence is inverted and reversed relative to the coding sequences of the cry genes.

TABLE 4

| cry Gene | % Identity to wd207 | Nucleotide Position in CDS |
|---|---|---|
| cry1Aa | 100% | 1903-1944 |
| cry1Ba | 95.2% | 1991-2032 |

TABLE 4-continued

| cry Gene | % Identity to wd207 | Nucleotide Position in CDS |
|---|---|---|
| cry1Ca | 97.6% | 1930-1971 |
| cry1Da | 97.6% | 1858-1899 |
| cry1Ea | 97.6% | 1885-1926 |

The labeled probe was then incubated with the nitrocellulose filter overnight at 45° C. in 3×SSC (1×SSC=0.15 M NaCl, 0.015 M sodium citrate), 0.1% SDS, 10×Denhardt's reagent (0.2% BSA, 0.2% polyvinylpyrrolidone, 0.2% Ficoll), and 0.2 mg/ml heparin. Following this incubation period, the filter was washed in several changes of 3×SSC, 0.1% SDS at 45° C. The filter was blotted dry and exposed to Kodak X-OMAT AR X-ray film (Eastman Kodak Co., Rochester, N.Y.) overnight at −70° C. with an intensifying screen to obtain an autoradiogram.

The autoradiograms were analyzed to determine which wild-type *B. thuringiensis* strains contained cry1 genes that could be novel. Since the probe was only 42 nucleotides, it is unlikely that recognition sites for the restriction endonucleases ClaI and PstI would occur within the hybridizing region of the cry1-related genes. Therefore, it was assumed that each hybridizing restriction fragment represented one cry1-related gene. The sizes, in kilobases (kb), of the hybridizing restriction fragments were determined based on the migration of the fragment in the agarose gel relative to DNA fragments of known size. The size of a fragment could be used to determine if that fragment represented a known cry1 gene. For example, from the DNA sequence of the cry1Ac gene it was known that wd207 would hybridize to a 0.43 kb fragment after digestion of cry1Ac DNA with ClaI and PstI. If the Southern blot analysis of a strain showed a 0.43 kb hybridizing fragment, that strain was assigned a probable genotype of cry1Ac. Fragments that could not be easily assigned a probable genotype were selected as candidates for further analysis. Because many cry1-containing strains have more than one cry1-related gene, all fragments were given a putative designation.

TABLE 5

SUMMARY OF GENES AND PROTEINS

| Polypeptide Designation | Polypeptide Seq. ID No.: | Polynucleotide Seq ID No.: | WT-Strain | Recomb. Strain | Gene Family | Cloning Method[1] | DNA Probe[2] | Cloning Vector | Plasmid |
|---|---|---|---|---|---|---|---|---|---|
| Cry ET31 | 2 | 1 | EG6701 | EG11562 | cry2 | MboI | cry2a | pHT315 | pEG1331 |
| Cry ET40 | 4 | 3 | EG5476 | EG11901 | cry1 | PCR™ | — | pEG1064 | pEG1901 |
| Cry ET43 | 6 | 5 | EG2878 | EG7692 | cry1 | PCR™ | — | pEG1064 | pEG1806 |
| Cry ET44 | 8 | 7 | EG3114 | EG11629 | cry1 | PCR™ | — | pEG1064 | pEG1807 |
| Cry ET45 | 10 | 9 | EG3114 | EG7694 | cry1 | PCR™ | — | pEG1064 | pEG1808 |
| Cry ET46 | 12 | 11 | EG6451 | EG7695 | cry1 | PCR™ | — | pEG1064 | pEG1809 |
| Cry ET47 | 14 | 13 | EG6451 | EG7696 | cry1 | PCR™ | — | pEG1064 | pEG1810 |
| Cry ET49 | 16 | 15 | EG6451 | EG11630 | cry1 | PCR™ | — | pEG1064 | pEG1812 |
| Cry ET51 | 18 | 17 | EG5391 | EG11921 | cry1 | MboI | wd207 | pHT315 | pEG1912 |
| Cry ET52 | 20 | 19 | EG10475 | EG11584 | cry1 | BamHI | wd207 | pEG290 | pEG1340 |
| Cry ET53 | 22 | 21 | EG3874 | EG11906 | cry1 | MboI | cry1Aa | pHT315 | pEG1904 |
| Cry ET54 |  |  | EG3874 | EG11907 | cry1 | MboI | cry1Aa | pHT315 | pEG1905 |
| Cry ET56 | 24 | 23 | EG3874 | EG11909 | cry1 | MboI | cry1Aa | pHT315 | pEG1907 |
| Cry ET57 | 26 | 25 | EG3874 | EG11910 | cry1 | MboI | cry1Aa | pHT315 | pEG1908 |
| Cry ET59 | 28 | 27 | EG9290 | EG12102 | cry9 | MboI | pr56, cryET59 | pHT315 | pEG945 |
| Cry ET60 | 30 | 29 | EG9290 | EG12103 | cry9 | MboI | pr56, cryET59 | pHT315 | pEG946 |
| Cry ET61 | 32 | 31 | EG4612 | EG11634 | cry1 | MboI | wd207 | pHT315 | pEG1813 |
| Cry ET62 | 34 | 33 | EG6831 | EG11635 | cry1 | MboI | wd207 | pHT315 | pEG1814 |
| Cry ET63 | 36 | 35 | EG4623 | EG11636 | cry1 | MboI | wd207 | pHT315 | pEG1815 |
| Cry ET64 | 38 | 37 | EG4612 | EG11638 | cry1 | MboI | wd207 | pHT315 | pEG1816 |
| Cry ET66 | 40 | 39 | EG5020 | EG11640 | cry1 | MboI | wd207 | pHT315 | pEG1817 |
| Cry ET67 | 42 | 41 | EG4869 | EG11642 | cry1 | MboI | wd207 | pHT315 | pEG1818 |
| Cry ET68 | 44 | 43 | EG5020 | EG11644 | cry1 | MboI | wd207 | pHT315 | pEG1819 |
| Cry ET72 | 46 | 45 | EG4420 | EG11440 | cry2 | HindIII | cry2Aa | pEG597 | pEG1260 |
| Cry ET73 | 48 | 47 | EG3874 | EG11465 | cry2 | HindIII | cry2Aa | pEG597 | pEG1279 |
| Cry ET83 | 50 | 49 | EG6346 | EG11785 | cry9 | MboI | cryET59, cryET83 | pHT315 | pEG397 |

[1]Methods include the construction of genomic libraries containing partial MboI fragments (Example 4), the construction of genomic libraries containing size-selected BamHI or HindIII restriction fragments (Example 5), the amplification of novel cry sequences by PCR™ and the construction of novel cry gene fusions (Example 6).
[2]Hybridization probes included the 700 base pair EcoRI fragment obtained from digestion of the cry1Aa gene, gene fragments from the cry2Aa, cryET59, and cryET83 genes, and synthetic oligonucleotides (wd207, pr56).

6.2 Example 2

Identification of *B. Thuringiensis* Strains Containing Novel Cry2-Related Genes Proteins encoded by the cry2 class of *B. thuringiensis* class of toxin genes have activity on the larvae of lepidopteran and diopteran insects. Southern blot hybridization analysis of DNA extracted from lepidopteran-active strains was utilized to identify novel cry2-related genes. Total genomic DNA was isolated as described in Section 6.1. The DNA was digested with the restriction endonuclease Sau3A and run on a 1.2% agarose gel as described. The digested DNA was transferred to nitrocellulose filters to be probed with a DNA fragment containing the cry2Aa gene. Hybridizations were performed at 55° C. and the filters washed and exposed to X-ray film to obtain an autoradiogram.

Sau3A digestion followed by hybridization with the cry2Aa gene gave characteristic patterns of hybridizing fragments allowing the identification of the cry2Aa, cry2Ab, and cry2Ac genes. Hybridizing fragments that differed from these patterns indicated the presence of a novel cry2-related gene in that strain.

Once a strain was identified as containing one or more novel cry2-related genes, an additional Southern blot hybridization was performed. The procedures were the same as those already described above, except another restriction enzyme, usually HindIII, was used. Since an enzyme like HindIII (a "six base cutter") cuts DNA less frequently than does Sau3A or MboI, it was more likely to generate a restriction fragment containing the entire cry2-related gene which could then be readily cloned.

6.3 Example 3

Identification of B. Thuringiensis Strains Containing Novel Cry9-Type Genes

A cry9-specific oligonucleotide, designated pr56, was designed to facilitate the identification of strains harboring cry9-type genes. This oligonucleotide corresponds to nucleotides 4349-4416 of the gene (GenBank Accession No. Z37527). The sequence of pr56 was as follows:

5'-AGTAACGGTGTTACTATTAGCGAGGGCG-GTCCATTCTTTAA AGGTCGTGCACTTCAGTTAGC-3' (SEQ ID NO:52).

*B. thuringiensis* isolates were spotted or "patched" on SGNB plates, with no more than 50 isolates per plate, and grown overnight at 25° C. The *B. thuringiensis* colonies were transferred to nitrocellulose filters and the filters placed, colony side up, on fresh SGNB plates for overnight growth at 30° C. Subsequently, the filters were placed, colony side up, on Whatman paper soaked in denaturing solution (1.5 M NaCl, 0.5 N NaOH) for 20 min. After denaturation, the filters were placed on Whatman paper soaked in neutralizing solution (3 M NaCl, 1.5 M Tris-HCl, pH 7.0) for 20 min. Finally, the filters were washed in 3×SSC (1×SSC=0.15 M NaCl and 0.015 M sodium citrate) to remove cellular debris and baked in a vacuum oven at 80° C. for 90 min.

The cry9-specific oligonucleotide pr56 (~10 pmoles) was end-labeled with [$\gamma$-$^{32}$P]ATP using T4 polynucleotide kinase. The labeling reaction was carried out at 37° C. for 20 min and terminated by incubating the reaction at 100 C for 3 min. After ethanol precipitation, the labeled oligonucleotide was resuspended in 100 μl distilled $H_2O$.

The filters were incubated with the cry9-specific probe in 6×SSC, 10×Denhardt's solution, 0.5% glycine, 0.2% SDS at 47° C. overnight. The filters were washed twice in 3×SSC, 0.1% SDS for 15 min at 47° C. and twice in 1×SSC, 0.1% SDS for 15 min at 47° C. The dried filters were exposed to X-OMAT XAR-5 film (Eastman Kodak Co.) at −70° C. using an intensifying screen. The developed autoradiogram revealed 24 isolates of *B. thuringiensis* containing DNA that hybridized to the cry9 probe.

To identify cry9C-type genes among these strains, two opposing oligonucleotide primers specific for the cry9C gene (GenBank Accession No. Z37527) were designed for polymerase chain reaction (PCR™) analyses. The sequence of pr58 is:

5'-CGACTTCTCCTGCTAATGGAGG-3' (SEQ ID NO:53).

The sequence of pr59 is:

5'-CTCGCTAATAGTAACACCGTTACTTGCC-3' (SEQ ID NO:54).

Plasmid DNAs were isolated from the isolates of *B. thuringiensis* believed to contain cry9-type genes. *B. thuringiensis* isolates were grown overnight at 30° C. on Luria agar plates and 2 loopfuls of cells from each isolate were suspended in 50 mM glucose, 10 mM Tris-HCl, 1 mM EDTA (1×GTE) containing 4 mg/ml lysozyme. After a 10 min incubation at room temperature, plasmid DNAs were extracted using a standard alkaline lysis procedure (Maniatis et al., 1982). The plasmid DNAs were resuspended in 20 μl of 1×TE (10 mM Tris-HCl, 1 mM EDTA, pH 7.5). Two microliters of the plasmid DNA preparations were used in the PCR™ reactions. Amplifications were performed in 100 μl volumes with a Perkin-Elmer DNA Thermocycler (Perkin-Elmer Cetus, Foster City, Calif.) using materials and methods provided in the Perkin-Elmer GeneAmp™ kit. Conditions for the PCR™ were as follows: 95° C. for 30 sec, 46° C. for 30 sec, 70° C. for 1 min; 30 cycles. A PCR™ using these primers and the cry9C gene as a template should yield a DNA fragment of ~970 bp. Of twenty-four strains found to hybridize to the cry9 probe (SEQ ID NO:XX), only one strain, EG9290, yielded the predicted amplified DNA fragment.

6.4 Example 4

Cloning of *B. Thuringiensis* Toxin Genes by Constructing MboI Partial Digest Libraries The restriction endonuclease MboI was utilized in the construction of genomic DNA libraries because it has a recognition sequence of four base pairs which occurs frequently in long stretches of DNA. Total genomic DNA was isolated from *B. thuringiensis* strains as described in Section 6.1. The DNA was digested under conditions allowing limited cleavage of a DNA strand. The method of establishing these conditions has been described (Maniatis et al., 1982). Digestion of DNA in this manner created a set of essentially randomly cleaved, overlapping fragments which were used to create a library representative of the entire genome.

The digested DNA fragments were separated, according to size, by agarose gel electrophoresis through a 0.6% agarose, 1×TBE gel, overnight at 2 volts/cm of gel length. The gel was stained with ethidium bromide so that the digested DNA could be visualized when exposed to long-wave UV light. A razor blade was used to excise a gel slice containing DNA fragments of approximately 9-kb to 12-kb in size. The DNA fragments were removed from the agarose by placing the slice in a dialysis bag with enough TE (10 mM Tris-HCl, 1 mM EDTA) to cover the slice. The bag was then closed and placed in a horizontal electrophoresis apparatus filled with 1×TBE buffer. The DNA was electroeluted from the slice into the TE at 100 volts for 2 h. The TE was removed from the bag, extracted with phenol:chloroform (1:1), followed by extraction with chloroform. The DNA fragments are then collected by the standard technique of ethanol precipitation (see Maniatis et al., 1982).

To create a library in *E. coli* of the partially-digested DNA, the fragments were ligated into the shuttle vector, pHT315 (Arantes and Lereclus, 1991). This plasmid contains replication origins for *E. coli* and *B. thuringiensis*, genes for resistance to the antibiotics erythromycin and ampicillin, and a multiple cloning site. The MboI fragments were mixed with BamHI-digested pHT315 that had been treated with calf intestinal, or bacterial, alkaline phosphatase (GibcoBRL, Gaithersburg, Md.) to remove the 5'-phosphates from the digested plasmid, preventing re-ligation of the vector to itself. After purification, T4 ligase and a ligation buffer (Promega Corp., Madison, Wis.) were added to the reaction containing the digested vector and the MboI fragments. These were incubated overnight at 15° C., or at room temperature for 1 h, to allow the insertion and ligation of the MboI fragments into the pHT315 vector DNA.

The ligation mixture was then introduced into transformation-competent *E. coli* SURE® cells (Stratagene Cloning Systems, La Jolla, Calif.), following procedures described by the manufacturer. The transformed *E. coli* cells were then plated on LB agar plates containing 50-75 µg/ml ampicillin and incubated overnight at 37° C. The growth of several hundred ampicillin-resistant colonies on each plate indicated the presence of recombinant plasmid in the cells of each of those colonies.

To isolate the colonies harboring sequences encoding toxin genes, the colonies were first transferred to nitrocellulose filters. This was accomplished by simply placing a circular nitrocellulose filter (Millipore HATF 08525, Millipore Corp., Bedford, Mass.) directly on top of the LB-ampicillin agar plates containing the transformed colonies. When the filter was slowly peeled off of the plate the colonies stick to the filter giving an exact replica of the pattern of colonies from the original plate. Enough cells from each colony were left on the plate that 5 to 6 h of growth at 37° C. restored the colonies. The plates were then stored at 4° C. until needed. The nitrocellulose filters with the transferred colonies are then placed, colony-side up, on fresh LB-ampicillin agar plates and allowed to grow at 37° C. until they reached an approximate 1 mm diameter.

To release the DNA from the recombinant *E. coli* cells the nitrocellulose filters were placed, colony-side up, on 2-sheets of Whatman 3 MM chromatography paper (Whatman International Ltd., Maidstone, England) soaked with 0.5 N NaOH, 1.5 M NaCl for 15 min. This treatment lysed the cells and denatured the released DNA allowing it to stick to the nitrocellulose filter. The filters were then neutralized by placing the filters, colony-side up, on 2 sheets of Whatman paper soaked with 1 M $NH_4$-acetate, 0.02 M NaOH for 10 min. The filters were rinsed in 3×SSC, air dried, and baked for 1 h at 80° C. in a vacuum oven. The filters were then ready for use in hybridization studies using probes to identify different classes of *B. thuringiensis* genes, as described in the above examples.

In order to identify colonies containing cloned cry1-related genes, the cry1-specific oligonucleotide wd207 was labeled at the 5'-end with [γ-$^{32}$P]ATP and T4 polynucleotide kinase. The labeled probe was added to the filters in 3×SSC, 0.1% SDS, 10×Denhardt's reagent (0.2% BSA, 0.2% polyvinylpyrrolidone, 0.2% Ficoll), 0.2 mg/ml heparin and incubated overnight at 47° C. These conditions allowed hybridization of the labeled oligonucleotide to related sequences present on the nitrocellulose blots of the transformed *E. coli* colonies. Following incubation the filters were washed in several changes of 3×SSC, 0.1% SDS at 45° C. The filters were blotted dry and exposed to Kodak X-OMAT AR X-ray film (Eastman Kodak Co., Rochester, N.Y.) overnight at −70° C. with an intensifying screen.

Colonies that contain cloned cry1-related sequences were identified by aligning signals on the autoradiogram with the colonies on the original transformation plates. The isolated colonies were then grown in LB-ampicillin liquid medium from which the cells could be harvested and recombinant plasmid prepared by the standard alkaline-lysis miniprep procedure (Maniatis et al., 1982). The plasmid DNA was then used as a template for DNA sequencing reactions necessary to confirm that the cloned gene was novel. If the cloned gene was novel, the plasmid was then introduced into a crystal protein-negative strain of *B. thuringiensis* (Cry) so that the encoded protein could be expressed and characterized. These procedures are described in detail in the following sections.

6.5 Example 5

Cloning of Specific Endonuclease Restriction Fragments

The identification of a specific restriction fragment containing a novel *B. thuringiensis* gene has been described for cry2-related genes in Section 2. The procedure for cloning a restriction fragment of known size was essentially the same as described for cloning an MboI fragment. The DNA was digested with a restriction enzyme (e.g., HindIII), and run through an agarose gel to separate the fragments by size. Fragments of the proper size, identified by Southern blot analysis (Example 2), were excised with a razor blade and electroeluted from the gel slice into TE buffer from which they could be precipitated. The isolated restriction fragments were then ligated into an *E. coli/B. thuringiensis* shuttle vector and transformed into *E. coli* to construct a size-selected library. The library could then be hybridized with a specific gene probe, as described in Example 4, to isolate the colony containing the cloned novel gene.

6.6 Example 6

Cloning of PCR™-Amplified Fragments

A rapid method for cloning and expressing novel cry1 gene fragments from *B. thuringiensis* was developed using the polymerase chain reaction. Flanking primers were designed to anneal to conserved regions 5' to and within cry1 genes. With the exception of certain cry3 genes, most *B. thuringiensis* cry genes are transcriptionally regulated, at least in part, by RNA polymerases containing the mother cell-specific $\sigma^E$ or sigE, sigma factor. These $\sigma^E$-regulated cry genes possess 5' promoter sequences that are recognized by $\sigma^E$. Alignment of these promoter sequences reveals considerable sequence variation, although a consensus sequence can be identified (Baum and Malvar, 1995). A primer, designated "sigE", containing a sequence identical to the cry1Ac $\sigma^E$ promoter sequence, was designed that would anneal to related $\sigma^E$ promoter sequences 5' to uncharacterized cry genes. The sigE primer also includes a BbuI site (isoschizimer: SphI) to facilitate cloning of amplified fragments. The sequence of the sigE primer is shown below:

5'-ATTTAGTAGCATGCGTTGCACTTTGTG-CATTTTTTCATAAGATGA GTCATATGTTTTAAAT-3' (SEQ ID NO:55).

The opposing primer, designated KpnR, anneals to a 3'-proximal region of the cry1 gene that is generally conserved. This primer incorporates an Asp718 site (isoschizimer: KpnI) conserved among the cry1A genes to facilitate cloning of the amplified fragment and to permit the construction of fusion proteins containing a carboxyl-terminal portion of the Cry1Ac protein. The sequence of the KpnR primer is shown below:

5'-GGATAGCACTCATCAAAGGTACC-3' (SEQ ID NO:56)

PCR™s were carried out using a Perkin Elmer DNA thermocycler and the following parameters: 94° C., 2 min.; 40 cycles consisting of 94° C., 30 sec; 40° C., 2 min; 72° C., 3 min; and a 10 second extension added to the 72° C. incubation after 20 cycles. The standard PCR™ buffer (100 µl volume) was modified to include 1×Taq Extender buffer, 25 µM each of the sigE and KpnR primers, and 0.5-1.0 µl of Taq Extender (Stratagene Inc.) in addition to 0.5-1.0 µl of Taq polymerase. Typically, 1-2 µl of the DNA preparations from novel *B. thuringiensis* isolates were included in the PCR™s. PCR™s with cry genes incorporating these primers resulted in the amplification of a ~2.3-kb DNA fragment flanked by restriction sites for BbuI and Asp718.

For the cloning and expression of these gene fragments, the cry1Ac shuttle vector pEG1064 was used. This plasmid is derived from the cry1Ac shuttle vector pEG857 (Baum et al., 1990), with the following modifications. A frameshift mutation was generated at a unique NcoI site within the cry1Ac coding region by cleaving pEG857 with the restriction endonuclease NcoI, blunt-ending the NcoI-generated ends with Klenow polymerase and ligating the blunt ends with T4 ligase. In similar fashion, an Asp718 site located in the multiple cloning site 3' to the cry1Ac gene was removed, leaving only the single Asp718 site contained within the cry1Ac coding sequence. The resulting plasmid, pEG1064, cannot direct the production of crystal protein when introduced into an acrystalliferous (Cry-) strain of *B. thuringiensis* because of the frameshift mutation. For cloning and expression of unknown cry genes, pEG1064 was cleaved with BbuI and Asp718 and the vector fragment purified following gel electrophoresis. Amplified fragments of unknown cry genes, obtained by PCR™ amplification of total *B. thuringiensis* DNA, were digested with the restriction endonucleases BbuI and Asp718 and ligated into the BbuI and Asp718 sites of the pEG1064 vector fragment. The ligation mixture was used to transform the Cry *B. thuringiensis* strains, EG10368 or EG10650, to chloramphenicol resistance using an electroporation protocol previously described (Mettus and Macaluso, 1990) Chloramphenicol-resistant ($Cm^R$) isolates were evaluated for crystal protein production by phase-contrast microscopy. Crystal forming (Cry+) isolates were subsequently grown in C2 liquid broth medium (Donovan et al., 1988) to obtain crystal protein for SDS-PAGE analysis and insect bioassay.

Because of the frameshift mutation within the cry1Ac gene, the crystal proteins obtained from the transformants could not be derived from the vector pEG1064. The $Cry^+$ transformants thus contained unknown cry gene fragments fused, at the Asp718 site, to a 3'-portion of the cry1Ac gene. Transcription of these gene fusions in *B. thuringiensis* was presumably directed from the $\sigma^E$ promoter incorporated into the amplified cry gene fragment. The fusion proteins, containing the entire active toxin region of the unknown Cry protein, were capable of producing crystals in *B. thuringiensis*.

6.7 Example 7

Cloning of Cry9-Related Genes

Total DNA was isolated from *B. thuringiensis* strain EG9290 for cloning studies. EG9290 was grown overnight at 30° C. in X brain heart infusion, 0.5% glycerol (BHIG). In the morning, 500 μl of the overnight growth was suspended in 50 ml BHIG and the culture incubated at 30° C. with agitation until the culture reached a Klett reading of 150 (red filter). The cells were harvested by centrifugation, suspended in 5 ml 1×GTE buffer containing 4 mg/ml lysozyme and 100 μg/ml Rnase A, and incubated at 37° C. for 20 min. The cells were lysed by the addition of 0.5 ml of 20% SDS. The released DNA was precipitated by the addition of 2.5 ml 7.5 M ammonium acetate and 7 ml of isopropanol. The precipitated DNA was spooled out of the mixture using a glass micropipette and washed in 80% ethanol. The DNA was resuspended in 10 ml 1×TE, extracted with one volume each of buffered phenol and chloroform:isoamyl alcohol (24:1), and precipitated as before. The spooled DNA was washed in 80% ethanol, allowed to air dry for several min, and suspended in 600 μl 1×TE. The DNA concentration was estimated at 500 μg/ml.

A library of EG9290 total DNA was constructed using partially digested MboI fragments of EG9290 DNA and the general methods described herein. The partial Mbol fragments were inserted into the unique BamHI site of cloning vector pHT315. The ligation mixture was used to transform *E. coli* Sure™ cells to ampicillin resistance by electroporation employing electrocompetent cells and protocols provided by Stratagene (La Jolla, Calif.) and the BioRad Gene Pulser™ apparatus (Bio-Rad Laboratories, Hercules, Calif.). Recombinant clones harboring cry9-type genes were identified by colony blot hybridization using a $^{32}P$-labeled probe consisting of the putative cry9C fragment generated by amplification of EG9290 DNA with primers pr58 and pr59. Plasmid DNAs were extracted from the *E. coli* clones using a standard alkaline lysis procedure.

Plasmid DNAs from the *E. coli* recombinant clones were used to transform *B. thuringiensis* strain EG10368 to erythromycin resistance using the electroporation procedure described by Mettus and Macaluso (1990). Cells were plated onto starch agar plates containing 20 μg/ml erythromycin and incubated at 30° C. After six days, colonies with a more opaque appearance were recovered from the plates and streaked out onto fresh starch agar plates containing 20 μg/ml erythromycin to isolate single colonies. Colonies exhibiting a more opaque appearance were observed to produce large parasporal inclusions/crystals by phase-contrast microscopy.

Recombinant EG10368 clones producing parasporal inclusion/crystals were evaluated for crystal protein production in broth culture. Single colonies were inoculated into C2 medium containing 10 μg/ml erythromycin and grown at 30° C. for 3 days at 28-30° C., at which time the cultures were fully sporulated and lysed. Spores and crystals were pelleted by centrifugation and resuspended in 20 mM Tris-HCl, 1 mM EDTA, pH 7.0. Aliquots of this material were analyzed by SDS-polyacrylamide gel electrophoresis (SDS-PAGE). Two EG10368 recombinant clones, initially identified as 9290-2 and 9290-3, were observed to produce distinct proteins of ~130 kDa. 9290-2 was designated EG12102 and 9290-3 was designated EG12103. The EG12102 protein was designated CryET59 while the EG12103 protein was designated CryET60.

Plasmid DNAs were prepared from EG12102 and EG12103 using a standard alkaline lysis procedure. Digestion of the plasmids with the restriction endonuclease XbaI confirmed that the two strains harbored distinct cry genes. The cry plasmids of EG12102 and EG12103, designated pEG945 and pEG946, respectively, were used to transform *E. coli* Sure™ cells to ampicillin resistance by electroporation, employing electrocompetent cells and protocols provided by Stratagene Inc. The *E. coli* recombinant strain containing pEG945 was designated EG12132, and the *E. coli* recombinant strain containing pEG946 was designated EG12133. pEG945 and pEG946 were purified from the *E. coli* recombinant strains using the QIAGEN midi-column plasmid purification kit and protocols (QIAGEN Inc., Valencia, Calif.).

The cryET83 gene was cloned from *B. thuringiensis* strain EG6346 subspecies *aizawai* using similar methods. Southern blot analysis of genomic DNA from EG6346 revealed a unique restriction fragment that hybridized to the cryET59 probe. A series of degenerate oligonucleotide primers, pr95, pr97, and pr98, were designed to amplify cry9-related sequences from genomic DNA. The sequences of these primers are as shown:

pr95: 5'-GTWTGGACSCRTCGHGATGTGG-3' (SEQ ID NO:57)

pr97: 5'-TAATTTCTGCTAGCCCWATTTCTGGATTTAATTGTTGATC-3' (SEQ ID NO:58)

pr98: 5'-ATWACNCAAMTWCCDTTRG-3' (SEQ ID NO:59)

where D=A, G; H=A, C, T; M=A, C; N=A, C, G, T; R=A, G; S=C, G; and W=A, T.

A PCR™ using Taq polymerase, Taq Extender™ (Stratagene, La Jolla, Calif.), the opposing primers pr95 and pr97, and total EG6346 DNA yielded a DNA fragment that was faintly visible on an ethidium bromide-stained agarose gel. This DNA served as the template for a second round of PCR™ using the opposing primers pr97 and pr98. The resulting amplified DNA fragment was suitable for cloning and served as a hybridization probe for subsequent cloning experiments. A library of EG6346 total DNA was constructed using partially digested 9-12 kb MboI fragments of EG6346 DNA ligated into the unique BamHI site of cloning vector pHT315. *E. coli* recombinant clones harboring the cryET83 gene were identified by colony blot hybridization using the EG6346-specific DNA fragment as a chemiluminescent hybridization probe and the CDP-Star™ nucleic acid chemiluminescent reagent kit from NEN™ Life Science Products (Boston, Mass.) to prepare the hybridization probe. The recombinant plasmid harboring the cryET83 gene was designated pEG397. The *E. coli* recombinant stain containing pEG397 was designated EG11786. The *B. thuringiensis* recombinant strain containing pEG397 was designated EG11785.

6.8 Example 8

Sequencing of Cloned *B. Thuringiensis* Toxin Genes

Partial sequences for the cloned toxin genes were determined following established dideoxy chain-termination DNA sequencing procedures (Sanger et al., 1977). Preparation of the Double Stranded Plasmid Template DNA was Accomplished Using a standard alkaline lysis procedure or using a QIAGEN plasmid purification kit (QIAGEN Inc., Valencia, Calif.). The sequencing reactions were performed using the Sequenase™ Version 2.0 DNA Sequencing Kit (United States Biochemical/Amersham Life Science Inc., Cleveland, Ohio) following the manufacturer's procedures and using $^{35}$S-dATP as the labeling isotope (obtained from DuPont NENO Research Products, Boston, Mass.). Denaturing gel electrophoresis of the reactions is done on a 6% (wt./vol.) acrylamide, 42% (wt./vol.) urea sequencing gel. The dried gels are exposed to Kodak X-OMAT AR X-ray film (Eastman Kodak Company, Rochester, N.Y.) overnight at room temperature. Alternatively, some cry genes were sequenced using automated sequencing methods. DNA samples were sequenced using the ABI PRISM™ DyeDeoxy sequencing chemistry kit (Applied Biosystems, Foster City, Calif.) according to the manufacturer's suggested protocol. The completed reactions were run on as ABI 377 automated DNA sequencer. DNA sequence data were analyzed using Sequencher™ v3.0 DNA analysis software (Gene Codes Corp., Ann Arbor, Mich.). Successive oligonucleotides to be used for priming sequencing reactions were designed from the sequencing data of the previous set of reactions.

The sequence determination for the cry1-related genes involved the use of the oligonucleotide probe wd207, described in Example 2, as the initial sequencing primer. This oligonucleotide anneals to a conserved region of cry1 genes, but because of the inverted and reversed orientation of wd207, it generates sequence towards the 5'-end of the coding region allowing sequence of the variable region of the gene to be read. A typical sequencing run of 250-300 nucleotides was usually sufficient to determine the identity of the gene. If additional data were necessary, one or more additional oligonucleotides could be synthesized to continue the sequence until it could be determined if the sequence was unique. In cases where wd207 did not function well as a primer, other oligonucleotides, designed to anneal to conserved regions of cry1 genes, were used. One such oligonucleotide was the KpnR primer described herein above.

The sequencing of the cloned cry2-related genes followed the same general procedures as those described for the cry1 genes, except that oligonucleotides specific for conserved regions in cry2 genes were used as sequencing primers. The two primers used in these examples were wd268 and wd269, shown below.

Primer wd268 corresponds to cry2Aa nucleotides 579-597
5'-AATGCAGATGAATGGGG-3' (SEQ ID NO:60).

Primer wd269 corresponds to cry2Aa 1740-1757
5'-TGATAATGGAGCTCGTT-3' (SEQ ID NO:61)

The sequencing of cryET59 and cryET60 commenced with the use of primer pr56. The sequencing of cryET83 commenced with the use of primer pr98. Successive oligonucleotides to be used for priming sequencing reactions were designed from the sequencing data of the previous set of reactions.

The derived sequences were compared to sequences of known cry genes using the FSTNSCAN program in the PC/GENE sequence analysis package (Intelligenetics, Mountain View, Calif.). This analysis permitted a preliminary classification of the cloned cry genes with respect to previously-known cry genes (Table 11).

TABLE 6

HOMOLOGY COMPARISON OF DNA SEQUENCES[1]

| Cloned Gene | DNA Sequence Identity |
|---|---|
| cryET31 | 90% identity with SEQ ID NO:4 of WO 98/40490 |
| cryET40 | 99% identity with cry1Aa |
| cryET43 | 88% identity with cry1Bd1 |
| cryET44 | 90% identity with cry1Da/1Db |
| cryET45 | 91% identity with cry1Da/1Db |
| cryET46 | 98% identity with cry1Ga |
| cryET47 | 99% identity with cry1Ab |
| cryET49 | 95% identity with cry1Ja |
| cryET51 | 85% identity with cry1Ac |
| cryET52 | 84% identity with cry1Da/1Db |
| cryET53 | 99% identity with SEQ ID NO:8 of US 5,723,758 |
| cryET54 | 99.8% identity with cry1Be |

TABLE 6-continued

HOMOLOGY COMPARISON OF DNA SEQUENCES[1]

| Cloned Gene | DNA Sequence Identity |
|---|---|
| cryET56 | 80% identity with cry1Ac |
| cryET57 | 98% identity with cry1Da |
| cryET59 | 95% identity with cry9Ca |
| cryET60 | 99.6% identity with cry9Aa |
| cryET61 | 97% identity with cry1Ha |
| cryET62 | 99% identity with cry1Ad |
| cryET63 | 93% identity with cry1Ac |
| cryET64 | 91% identity with SEQ ID NO:9 of US 5,723,758 |
| cryET66 | 76% identity with cry1Ga |
| cryET67 | 99% identity with SEQ ID NO:10 of US 5,723,758 |
| cryET72 | 98% identity with SEQ ID NO:4 of WO 98/40490 |
| cryET73 | 99% identity with SEQ ID NO:6 of WO 98/40490 |
| cryET83 | |

[1] Ktup value set at 2 for FSTNSCAN. The cryET59 and cryET60 sequences were compared using the FASTA program (Ktup = 6) in the PC/GENE sequence analysis package.

6.9 Example 9

Expression of Cloned Toxin Genes in a *B. Thuringiensis* Host

Plasmid DNA was isolated from *E. coli* colonies identified by hybridization to a gene-specific probe. The isolated plasmid was then introduced into a crystal protein-negative (Cry-) strain of *B. thuringiensis* using the electroporation protocol of Mettus and Macaluso (1990). Each of the cloning vectors used (see Table 5) has a gene to confer antibiotic resistance on the cells harboring that plasmid. *B. thuringiensis* transformants were selected by growth on agar plates containing 25 mg/ml erythromycin (pHT315) or 5 mg/ml chlorarnphenicol (pEG597 and pEG1064). Antibiotic-resistant colonies were then evaluated for crystal protein production by phase-contrast. microscropy. Crystal producing colonies were then grown in C2 medium (Donovan et al., 1988) to obtain cultures which were analyzed by SDS-PAGE and insect bioassay.

C2 cultures were inoculated with cells from Cry+ colonies and grown for three days at 25-30° C. in the presence of the appropriate antibiotic. During this time the culture grew to stationary phase, sporulated and lysed, releasing the protein inclusions into the medium. The cultures are harvested by centrifugation, which pellets the spores and crystals. The pellets were washed in a solution of 0.005% Triton X-100®, 2 mM EDTA and centrifuged again. The washed pellets were resuspended at one-tenth the original volume in 0.005% Triton X-100®, 2 mM EDTA.

Crystal protein were solubilized from the spores-crystal suspension by incubating the suspension in a solubilization buffer [0.14 M Tris-HCl pH 8.0, 2% (wt./vol.) sodium dodecyl sulfate (SDS), 5% (vol./vol.) 2-mercaptoethanol, 10% (vol./vol.) glycerol, and 0.1% bromphenol blue] at 100° C. for 5 min. The solubilized crystal proteins were size-fractionated by SDS-PAGE using a gel with an acrylamide concentration of 10%. After size fractionation the proteins were visualized by staining with Coomassie Brilliant Blue R-250.

The expected size for Cry1- and Cry9-related crystal proteins was approximately 130 kDa. The expected size for Cry2-related proteins was approximately 65 kDa.

6.10 Example 10

Insecticidal Activity of the Cloned *B. Thuringiensis* Toxin Genes

*B. thuringiensis* recombinant strains producing individual cloned cry genes were grown in C2 medium until the cultures were fully sporulated and lysed. These C2 cultures were used to evaluate the insecticidal activity of the crystal proteins produced. Each culture was diluted with 0.005% Triton® X-100 to achieve the appropriate dilution for two-dose bioassay screens. Fifty microliters of each dilution were topically applied to 32 wells containing 1.0 ml artificial diet per well (surface area of 175 mm²). A single lepidopteran larvae was placed in each of the treated wells and the tray was covered by a clear perforated mylar sheet. With the exception of the *P. xylostella* bioassays, that employed 3rd instar larvae, all the bioassays were performed with neonate larvae. Larval mortality was scored after 7 days of feeding at 28-30° C. and percent mortality was expressed as ratio of the number of dead larvae to the total number of larvae treated (Table 12). In some instances, severe stunting of larval growth was observed after 7 days, and the ratio of stunted/unstunted larva was also recorded. The bioassay results shown in Table 7 demonstrate that the crystal proteins produced by the recombinant *B. thuringiensis* strains do exhibit insecticidal activity and, furthermore,

TABLE 7A

Bioassay evaluations with ET crystal proteins

| | Spodoptera exigua | | | Spodoptera frugiperda | | |
|---|---|---|---|---|---|---|
| | 250 nl/well % mortality | 2500 nl/well % mortality | # stunted/# treated | 250 nl/well % | 2500 nl/well | # stunted/# treated |
| Cry1Ac | 0 | 5 | 4/32 | 16 | 53 | 1/32 |
| ET31 | 5 | 12 | 17/32 | 9 | 6 | 4/32 |
| ET40 | 0 | 5 | 0 | 3 | 3 | 0 |
| ET43 | 0 | 8 | 0 | 3 | 3 | 2/32 |
| ET44 | 0 | 2 | 0 | 6 | 0 | 1/32 |
| ET45 | 0 | 0 | 0 | 0 | 0 | 1/32 |
| ET46 | 0 | 12 | 0 | 0 | 6 | 0 |
| ET47 | 19 | 49 | 11/43 | 31 | 81 | 6/32 |
| ET49 | 0 | 8 | 0 | 0 | 3 | 0 |
| ET51 | 0 | 0 | 0 | 0 | 0 | 0 |
| ET52 | 0 | 0 | 0 | 3 | 3 | 0 |
| ET53 | 0 | 0 | 0 | 3 | 0 | 0 |
| ET54 | 0 | 66 | 3/32 | 6 | 34 | 9/32 |
| ET56 | 0 | 0 | 0 | 0 | 6 | 0 |

TABLE 7A-continued

Bioassay evaluations with ET crystal proteins

| | Spodoptera exigua | | | Spodoptera frugiperda | | |
|---|---|---|---|---|---|---|
| | 250 nl/well % mortality | 2500 nl/well % mortality | # stunted/ # treated | 250 nl/well % | 2500 nl/well | # stunted/# treated |
| ET57 | 2 | 15 | 18/32 | 3 | 94 | 0 |
| ET59 | 0 | 0 | 0 | 0 | 3 | 0 |
| ET60 | 0 | 0 | 0 | 0 | 3 | 0 |
| ET61 | 2 | 5 | 2/32 | 0 | 3 | 0 |
| ET62 | 2 | 59 | 12/32 | 0 | 13 | 0 |
| ET63 | 0 | 12 | 5/32 | 3 | 0 | 0 |
| ET64 | 0 | 0 | 0 | 3 | 6 | 0 |
| ET66 | 0 | 12 | 1/43 | 3 | 0 | 1/31 |
| ET67 | 29 | 90 | 0 | 13 | 61 | 0 |
| ET72 | 0 | 0 | 0 | 3 | 94 | 5/31 |
| ET73 | 0 | 2 | 0 | 0 | 0 | 0 |
| Control | 8 | 8 | 0 | 0 | 0 | 0 |

TABLE 7B

Bioassay evaluations with ET crystal proteins

| | Plutella xylostella | | | Ostrinia nubilalis | | |
|---|---|---|---|---|---|---|
| | 250 nl/well % | 2500 nl/well % mortality | # stunted/ # treated | 250 nl/well % mortality | 2500 nl/well % mortality | # stunted/# treated |
| Cry1Ac | 100 | 100 | 0 | 100 | 100 | 0 |
| ET31 | 0 | 2 | 0 | 100 | 100 | 0 |
| ET40 | 0 | 68 | 0 | 0 | 0 | 2/32 |
| ET43 | 5 | 100 | 0 | 46 | 100 | 0 |
| ET44 | 0 | 0 | 0 | 0 | 0 | 3/32 |
| ET45 | 0 | 0 | 0 | 0 | 0 | 4/32 |
| ET46 | 0 | 8 | 0 | 0 | 0 | 0 |
| ET47 | 100 | 100 | 0 | 100 | 100 | 0 |
| ET49 | 0 | 5 | 0 | 0 | 0 | 0 |
| ET51 | 0 | 0 | 0 | 0 | 0 | 0 |
| ET52 | 2 | 43 | 0 | 0 | 14 | 16/32 |
| ET53 | 8 | 97 | 0 | 4 | 46 | 5/32 |
| ET54 | 14 | 100 | 0 | 25 | 89 | 1/32 |
| ET56 | 0 | 0 | 0 | 0 | 0 | 0 |
| ET57 | 0 | 97 | 0 | 0 | 7 | 0 |
| ET59 | 100 | 100 | 0 | 96 | 100 | 0 |
| ET60 | 100 | 100 | 0 | 100 | 96 | 0 |
| ET61 | 0 | 11 | 0 | 0 | 0 | 2/32 |
| ET62 | 97 | 100 | 0 | 100 | 100 | 0 |
| ET63 | 100 | 100 | 0 | 100 | 100 | 0 |
| ET64 | 40 | 100 | 0 | 68 | 100 | 0 |
| ET66 | 100 | 100 | 0 | 86 | 100 | 0 |
| ET67 | 87 | 100 | 0 | 0 | 79 | 1/32 |
| ET72 | 0 | 0 | 0 | 0 | 0 | 0 |
| ET73 | 2 | 2 | 0 | 93 | 100 | 0 |
| Control | 2 | 2 | 0 | 0 | 0 | 0 |

TABLE 7c

Bioassay evaluations with ET crystal proteins

| | Heliothis virescens | | | Helicoverpa zea | |
|---|---|---|---|---|---|
| | 250 nl/well % | 2500 nl/well % mortality | # stunted/ # treated | 250 nl/well % mortality | 2500 nl/well % mortality |
| Cry1Ac | 100 | 100 | 0 | 100 | 100 |
| ET31 | 97 | 97 | 1/32 | 8 | 81 |
| ET40 | 2 | 5 | 2/32 | 2 | 5 |
| ET43 | 87 | 97 | 1/32 | 0 | 2 |
| ET44 | 8 | 5 | 1/32 | 5 | 8 |
| ET45 | 0 | 11 | 0 | 8 | 18 |
| ET46 | 12 | 25 | 0 | 0 | 8 |
| ET47 | 87 | 100 | 0 | 83 | 100 |
| ET49 | 8 | 2 | 0 | 11 | 15 |
| ET51 | 2 | 15 | 0 | 5 | 5 |
| ET52 | 0 | 31 | 1/32 | 93 | 11 |
| ET53 | 22 | 64 | 2/32 | 90 | 61 |

TABLE 7c-continued

| Bioassay evaluations with ET crystal proteins | | | | | |
|---|---|---|---|---|---|
| | *Heliothis virescens* | | | *Helicoverpa zea* | |
| | 250 nl/well % | 2500 nl/well % mortality | # stunted/# treated | 250 nl/well % mortality | 2500 nl/well % mortality |
| ET54 | 15 | 64 | 5/32 | 2 | 5 |
| ET56 | 0 | 11 | 0 | 8 | 0 |
| ET57 | 2 | 0 | 0 | 11 | 28 |
| ET59 | 28 | 84 | 4/32 | 2 | 2 |
| ET60 | 56 | 97 | 1/32 | 31 | 28 |
| ET61 | 5 | 5 | 0 | 8 | 5 |
| ET62 | 44 | 87 | 4/32 | 21 | 64 |
| ET63 | 100 | 100 | 0 | 100 | 100 |
| ET64 | 0 | 21 | 0 | 5 | 0 |
| ET66 | 0 | 8 | 1/32 | 0 | 5 |
| ET67 | 18 | 93 | 1/32 | 0 | 68 |
| ET72 | 34 | 64 | 11/32 | 8 | 2 |
| ET73 | 42 | 90 | 2/32 | 8 | 48 |
| Control | 5 | 5 | 0 | 5 | 5 |

TABLE 8

| Bioassay Evaluation of CryET59 and CryET60 Percent mortality[1] | | | | | | | | | |
|---|---|---|---|---|---|---|---|---|---|
| Toxin | Dose ng/well | *AI* | *HV* | *HZ* | *ON* | *PX* | r*PX* | *SE* | *TN* |
| Control[2] | — | 2 | 6 | 0 | 0 | 2 | 0 | 2 | 0 |
| CryET59 | 100 | 2 | 37 | 0 | 94 | 100 | 100 | 2 | 13 |
| CryET59 | 500 | 11 | 80 | 3 | 100 | 100 | 100 | 0 | 63 |
| CryET59 | 5000 | 62 | 100 | 6 | 100 | 100 | 100 | 71 | 100 |
| CryET60 | 500 | 0 | 93 | 22 | 100 | 100 | 100 | 0 | 100 |
| CryET60 | 5000 | 2 | 100 | 25 | 100 | 100 | 100 | 14 | 100 |

[1]*AI = Agrotis ipsilon, HV = Heliothis virescens, HZ = Helicoverpa zea, ON = Ostrinia nubilalis, PX = Plutella xylostella*, r*PX = Plutella xylostella* colony resistant to Cry1A and Cry IF toxins, *SE = Spodoptera exigua, TN = Trichoplusia ni*.

[2]Control = no toxin added.

TABLE 7D

| Bioassay evaluations with ET crystal proteins | | | | | | |
|---|---|---|---|---|---|---|
| | *Agrotis ipsilon* | | | *Trichoplusia ni* | | |
| | 250 nl/well % | 2500 nl/well % mortality | # stunted/# treated | 250 nl/well % mortality | 2500 nl/well % mortality | # stunted/# treated |
| Cry1Ac | 94 | 100 | | 100 | 100 | 0 |
| ET31 | 6 | 6 | | 90 | 100 | 0 |
| ET40 | 0 | 6 | | 13 | 32 | 0 |
| ET43 | 0 | 45 | | 100 | 100 | 0 |
| ET44 | 6 | 13 | | 16 | 26 | 0 |
| ET45 | 0 | 6 | | 13 | 39 | 0 |
| ET46 | 0 | 0 | | 29 | 74 | 0 |
| ET47 | 0 | 34 | | 97 | 100 | 0 |
| ET49 | 3 | 0 | | 13 | 81 | 0 |
| ET51 | 0 | 0 | | 3 | 19 | 0 |
| ET52 | 0 | 28 | | 81 | 100 | 0 |
| ET53 | 25 | 81 | | 74 | 100 | 0 |
| ET54 | 3 | 6 | | 100 | 100 | 0 |
| ET56 | 3 | 3 | | 16 | 26 | 0 |
| ET57 | 13 | 74 | | 19 | 100 | 0 |
| ET59 | 3 | 3 | | 10 | 84 | 0 |
| ET60 | 3 | 0 | | 97 | 100 | 0 |
| ET61 | 6 | 28 | | 29 | 52 | 0 |
| ET62 | 23 | 58 | | 100 | 100 | 0 |
| ET63 | 3 | 0 | | 100 | 100 | 0 |
| ET64 | 0 | 0 | | 87 | 100 | 0 |
| ET66 | 13 | 91 | | 26 | 81 | 0 |
| ET67 | 3 | 0 | | 6 | 100 | 0 |
| ET72 | 0 | 0 | | 23 | 74 | 8/32 |
| ET73 | 13 | 6 | | 94 | 100 | 0 |
| Control | 0 | 0 | | 3 | 3 | 0 | that the crystal proteins exhibit differential activity towards the lepidopteran species tested.

Additional bioassays were performed with the crystal proteins designated CryET59, CryET60, CryET66, and CryET83. Crystal proteins produced in C2 medium were quantified by SDS-PAGE and densitometry using the method described by Brussock, S. M. and Currier, T. C., 1990, "Use of Sodium Dodecyl Sulfate-Polyacrylamide Gel Electrophoresis to Quantify *Bacillus thuringiensis* δ-Endotoxins", in Analytical Chemistry of *Bacillus thuringiensis* (L. A. Hickle and W. L. Fitch, eds.), The American Chemical Society, pp. 78-87. The procedure was modified to eliminate the neutralization step with 3M HEPES. Crystal proteins resolved by SDS-PAGE were quantified by densitometry using a Molecular Dynamics model 300A computing densitometer and purified bovine serum albumin (Pierce, Rockford, Ill.) as a standard.

The bioassay results shown in Table 8 demonstrate that CryET59 and CryET60 are toxic to a number of lepidopteran species, including a colony of *P. xylostella* that is resistant to Cry1A and Cry1F crystal proteins. Eight-dose assays with CryET66 also demonstrated excellent toxicity towards both the susceptible and resistant colonies of *P. xylostella* (Table 14). In this instance, eight crystal protein concentrations were prepared by serial dilution of the crystal protein suspensions in 0.005% Triton® X-100 and 50 ul of each concentration was topically applied to wells containing 1.0 ml of artificial diet.

After the wells had dried, a single larvae was placed in each of the treated wells and the tray was covered by a clear perforated mylar sheet (32 larvae for each crystal protein concentration). Larval mortality was scored after 7 days of feeding at 28-30° C. Mortality data was expressed as $LC_{50}$ and $LC_{95}$ values, the concentration of crystal protein (ng/175 mm$^2$ diet well) causing 50% and 95% mortality, respectively (Daum, 1970).

TABLE 9

Toxicity of CryET66 towards *Plutella xylostella*

| Toxin | $LC_{50}^1$ | 95% C.I. | $LC_{95}^2$ | Slope |
|---|---|---|---|---|
| Cry1Ac | 8.05 | 5.0-15.2 | 52.94 | 2.01 |
| Cry1C | 25.06 | 15.7-40.6 | 117.07 | 2.46 |
| CryET66 | 0.42 | 0.4-0.5 | 1.4 | 3.13 |

Toxicity of CryET66 towards Cry1A-resistant *Plutella xylostella*

| Toxin | $LC_{50}^1$ | 95% C.I. | $LC_{95}^2$ | Slope |
|---|---|---|---|---|
| Cry1Ac | | *No significant mortality | | |
| Cry1C | 27.32 | 15.4-51.1 | 156.13 | 2.17 |
| CryET66 | 1.65 | 1.3-2.0 | 6.41 | 2.79 |

$^1$the concentration of crystal protein, in nanograms of crystal protein per well, required to achieve 50% mortality
$^2$the concentration of crystal protein, in nanograms of crystal protein per well, required to achieve 95% mortality.

Table 15 shows that the CryET83 protein exhibits toxicity towards a wide variety of lepidopteran pests and may exhibit improved toxicity towards *S. exigua* and *H. virescens* when compared to the other Cry9-type proteins CryET59 and CryET60.

TABLE 10

Toxicity of CryET83 towards lepidopteran larvae$^1$

| Dose 2 | AI$^3$ | HV | HZ | ON | PX | SE | SF | TN |
|---|---|---|---|---|---|---|---|---|
| 5 | | | | | 5 | | | |
| 10 | | 9 | | | | | | |
| 50 | | 53 | | | 75 | | | 69 |
| 100 | | | 91 | | | | | |
| 500 | 0 | 100 | | | | 67 | | 100 |
| 5000 | 32 | | | | | 100 | | |
| 10000 | | | 84 | | | | 100 | |

$^1$Toxicity calculated as percent mortality among treated *larvae*.
$^2$ng CryET83 crystal protein/175 mm$^2$ diet well
$^3$Abbreviations described in Table 8; SF = *Spodoptera frugiperda*

The recombinant *B. thuringiensis* strains listed in Table 5 were deposited with the ARS Patent Culture Collection and had been assigned the NRRL deposit numbers shown in Table 11.

TABLE 11

Biological Deposits

| Polypeptide Designation | Polypeptide Seq. ID No.: | Polynucleotide Seq ID No.: | Recomb. Strain | NRRL Deposit No.: |
|---|---|---|---|---|
| Cry ET31 | 2 | 1 | EG11562 | B-21921 |
| Cry ET40 | 4 | 3 | EG11901 | B-21922 |
| Cry ET43 | 6 | 5 | EG7692 | B-21923 |
| Cry ET44 | 8 | 7 | EG11629 | B-21924 |

TABLE 11-continued

Biological Deposits

| Polypeptide Designation | Polypeptide Seq. ID No.: | Polynucleotide Seq ID No.: | Recomb. Strain | NRRL Deposit No.: |
|---|---|---|---|---|
| Cry ET45 | 10 | 9 | EG7694 | B-21925 |
| Cry ET46 | 12 | 11 | EG7695 | B-21926 |
| Cry ET47 | 14 | 13 | EG7696 | B-21927 |
| Cry ET49 | 16 | 15 | EG11630 | B-21928 |
| Cry ET51 | 18 | 17 | EG11921 | B-21929 |
| Cry ET52 | 20 | 19 | EG11584 | B-21930 |
| Cry ET53 | 22 | 21 | EG11906 | B-21931 |
| Cry ET54 | 63 | 62 | EG11907 | B-21932 |
| Cry ET56 | 24 | 23 | EG11909 | B-21933 |
| Cry ET57 | 26 | 25 | EG11910 | B-21934 |
| Cry ET59 | 28 | 27 | EG12102 | B-21935 |
| Cry ET60 | 30 | 29 | EG12103 | B-21936 |
| Cry ET61 | 32 | 31 | EG11634 | B-21937 |
| Cry ET62 | 34 | 33 | EG11635 | B-21938 |
| Cry ET63 | 36 | 35 | EG11636 | B-21939 |
| Cry ET64 | 38 | 37 | EG11638 | B-21940 |
| Cry ET66 | 40 | 39 | EG11640 | B-21941 |
| Cry ET67 | 42 | 41 | EG11642 | B-21942 |
| Cry ET68 | 44 | 43 | EG11644 | B-30137 |
| Cry ET72 | 46 | 45 | EG11440 | B-21943 |
| Cry ET73 | 48 | 47 | EG11465 | B-21944 |
| Cry ET83 | 50 | 49 | EG11785 | B-30138 |

6.11 Example 11

Modification of Cry Genes for Expression in Plants

Wild-type cry genes are known to be expressed poorly in plants as a full length gene or as a truncated gene. Typically, the G+C content of a cry gene is low (37%) and often contains many A+T rich regions, potential polyadenylation sites and numerous ATTTA sequences. Table 12 shows a list of potential polyadenylation sequences which should be avoided when preparing the "plantized" gene construct.

TABLE 12

List of Sequences of Potential Polyadenylation Signals

| | |
|---|---|
| AATAAA* | AAGCAT |
| AATAAT* | ATTAAT |
| AACCAA | ATACAT |
| ATATAA | AAAATA |
| AATCAA | ATTAAA** |
| ATACTA | AATTAA** |
| ATAAAA | AATACA** |
| ATGAAA | CATAAA** |

*indicates a potential major plant polyadenylation site.
**indicates a potential minor animal polyadenylation site.
All others are potential minor plant polyadenylation sites.

The regions for mutagenesis may be selected in the following manner. All regions of the DNA sequence of the cry gene are identified which contained five or more consecutive base pairs which were A or T. These were ranked in terms of length and highest percentage of A+T in the surrounding sequence over a 20-30 base pair region. The DNA is analysed for regions which might contain polyadenylation sites or ATTTA sequences. Oligonucleotides are then designed which maximize the elimination of A+T consecutive regions which contained one or more polyadenylation sites or ATTTA sequences. Two potential plant polyadenylation sites have been shown to be more critical based on published reports. Codons are selected which increase G+C content, but do not generate restriction sites for enzymes useful for cloning and assembly of the modified gene (e.g., BamHI, BglII, SacI, NcoI, EcoRV, etc.). Likewise condons are avoided which contain the doublets TA or GC which have been reported to be infrequently-found codons in plants.

Although the CaMV35S promoter is generally a high level constitutive promoter in most plant tissues, the expression level of genes driven the CaMV35S promoter is low in floral tissue relative to the levels seen in leaf tissue. Because the economically important targets damaged by some insects are the floral parts or derived from floral parts (e.g., cotton squares and bolls, tobacco buds, tomato buds and fruit), it is often advantageous to increase the expression of crystal proteins in these tissues over that obtained with the CaMV35S promoter.

The 35S promoter of Figwort Mosaic Virus (FMV) is analogous to the CaMV35S promoter. This promoter has been isolated and engineered into a plant transformation vector. Relative to the CaMV promoter, the FMV 35S promoter is highly expressed in the floral tissue, while still providing similar high levels of gene expression in other tissues such as leaf. A plant transformation vector, may be constructed in which the full length synthetic cry gene is driven by the FMV 35S promoter. Tobacco plants may be transformed with the vector and compared for expression of the crystal protein by Western blot or ELISA immunoassay in leaf and floral tissue. The FMV promoter has been used to produce relatively high levels of crystal protein in floral tissue compared to the CaMV promoter.

6.12 Example 12

Expression of Synthetic Cry Genes with ssRUBISCO Promoters and Chloroplast Transit Peptides The genes in plants encoding the small subunit of RUBISCO(SSU) are often highly expressed, light regulated and sometimes show tissue specificity. These expression properties are largely due to the promoter sequences of these genes. It has been possible to use SSU promoters to express heterologous genes in transformed plants. Typically a plant will contain multiple SSU genes, and the expression levels and tissue specificity of different SSU genes will be different. The SSU proteins are encoded in the nucleus and synthesized in the cytoplasm as precursors that contain an N-terminal extension known as the chloroplast transit peptide (CTP). The CTP directs the precursor to the chloroplast and promotes the uptake of the SSU protein into the chloroplast. In this process, the CTP is cleaved from the SSU protein. These CTP sequences have been used to direct heterologous proteins into chloroplasts of transformed plants.

The SSU promoters might have several advantages for expression of heterologous genes in plants. Some SSU promoters are very highly expressed and could give rise to expression levels as high or higher than those observed with the CaMV35S promoter. The tissue distribution of expression from SSU promoters is different from that of the CaMV35S promoter, so for control of some insect pests, it may be advantageous to direct the expression of crystal proteins to those cells in which SSU is most highly expressed. For example, although relatively constitutive, in the leaf the CaMV35S promoter is more highly expressed in vascular tissue than in some other parts of the leaf, while most SSU promoters are most highly expressed in the mesophyll cells of the leaf. Some SSU promoters also are more highly tissue specific, so it could be possible to utilize a specific SSU promoter to express the protein of the present invention in only a subset of plant tissues, if for example expression of such a protein in certain cells was found to be deleterious to those cells. For example, for control of Colorado potato beetle in potato, it may be advantageous to use SSU promoters to direct crystal protein expression to the leaves but not to the edible tubers.

Utilizing SSU CTP sequences to localize crystal proteins to the chloroplast might also be advantageous. Localization of the B. thuringiensis crystal proteins to the chloroplast could protect these from proteases found in the cytoplasm. This could stabilize the proteins and lead to higher levels of accumulation of active toxin. cry genes containing the CTP may be used in combination with the SSU promoter or with other promoters such as CaMV35S.

6.13 Example 13

Targeting of Cry Proteins to the Extracellular Space or Vacuole Through the Use of Signal Peptides The B. thuringiensis proteins produced from the synthetic genes described here are localized to the cytoplasm of the plant cell, and this cytoplasmic localization results in plants that are insecticidally effective. It may be advantageous for some purposes to direct the B. thuringiensis proteins to other compartments of the plant cell. Localizing B. thuringiensis proteins in compartments other than the cytoplasm may result in less exposure of the B. thuringiensis proteins to cytoplasmic proteases leading to greater accumulation of the protein yielding enhanced insecticidal activity. Extracellular localization could lead to more efficient exposure of certain insects to the B. thuringiensis proteins leading to greater efficacy. If a B. thuringiensis protein were found to be deleterious to plant cell function, then localization to a noncytoplasmic compartment could protect these cells from the protein.

In plants as well as other eukaryotes, proteins that are destined to be localized either extracellularly or in several specific compartments are typically synthesized with an N-terminal amino acid extension known as the signal peptide. This signal peptide directs the protein to enter the compartmentalization pathway, and it is typically cleaved from the mature protein as an early step in compartmentalization. For an extracellular protein, the secretory pathway typically involves cotranslational insertion into the endoplasmic reticulum with cleavage of the signal peptide occurring at this stage. The mature protein then passes through the Golgi body into vesicles that fuse with the plasma membrane thus releasing the protein into the extracellular space. Proteins destined for other compartments follow a similar pathway. For example, proteins that are destined for the endoplasmic reticulum or the Golgi body follow this scheme, but they are specifically retained in the appropriate compartment. In plants, some proteins are also targeted to the vacuole, another membrane bound compartment in the cytoplasm of many plant cells. Vacuole targeted proteins diverge from the above pathway at the Golgi body where they enter vesicles that fuse with the vacuole.

A common feature of this protein targeting is the signal peptide that initiates the compartmentalization process. Fusing a signal peptide to a protein will in many cases lead to the targeting of that protein to the endoplasmic reticulum. The efficiency of this step may depend on the sequence of the mature protein itself as well. The signals that direct a protein to a specific compartment rather than to the extracellular space are not as clearly defined. It appears that many of the signals that direct the protein to specific compartments are contained within the amino acid sequence of the mature protein. This has been shown for some vacuole targeted proteins, but it is not yet possible to define these sequences precisely. It appears that secretion into the extracellular space is the "default" pathway for a protein that contains a signal sequence but no other compartmentalization signals. Thus, a strategy to direct *B. thuringiensis* proteins out of the cytoplasm is to fuse the genes for synthetic *B. thuringiensis* genes to DNA sequences encoding known plant signal peptides. These fusion genes will give rise to *B. thuringiensis* proteins that enter the secretory pathway, and lead to extracellular secretion or targeting to the vacuole or other compartments.

Signal sequences for several plant genes have been described. One such sequence is for the tobacco pathogenesis related protein PR1b has been previously described (Cornelissen et al., 1986). The PR1b protein is normally localized to the extracellular space. Another type of signal peptide is contained on seed storage proteins of legumes. These proteins are localized to the protein body of seeds, which is a vacuole like compartment found in seeds. A signal peptide DNA sequence for the β-subunit of the 7S storage protein of common bean (*Phaseolus vulgaris*), PvuB has been described (Doyle et al., 1986). Based on the published these published sequences, genes may be synthesized chemically using oligonucleotides that encode the signal peptides for PR1b and PvuB. In some cases to achieve secretion or compartmentalization of heterologous proteins, it may be necessary to include some amino acid sequence beyond the normal cleavage site of the signal peptide. This may be necessary to insure proper cleavage of the signal peptide.

6.14 Example 14

Isolation of Transgenic Plants Resistant to Insects Using Cry Transgenes

6.64.1 Plant Gene Construction

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA. Transcription of DNA into mRNA is regulated by a region of DNA usually referred to as the "promoter". The promoter region contains a sequence of bases that signals RNA polymerase to associate with the DNA and to initiate the transcription of mRNA using one of the DNA strands as a template to make a corresponding strand of RNA.

A number of promoters which are active in plant cells have been described in the literature. Such promoters may be obtained from plants or plant viruses and include, but are not limited to, the nopaline synthase (NOS) and octopine synthase (OCS) promoters (which are carried on tumor-inducing plasmids of *Agrobacterium tumefaciens*), the cauliflower mosaic virus (CaMV) 19S and 35S promoters, the light-inducible promoter from the small subunit of ribulose 1,5-bisphosphate carboxylase (ssRUBISCO, a very abundant plant polypeptide), and the Figwort Mosaic Virus (FMV) 35S promoter. All of these promoters have been used to create various types of DNA constructs which have been expressed in plants (see e.g., U.S. Pat. No. 5,463,175, specifically incorporated herein by reference).

The particular promoter selected should be capable of causing sufficient expression of the enzyme coding sequence to result in the production of an effective amount of protein. One set of preferred promoters are constitutive promoters such as the CaMV35S or FMV35S promoters that yield high levels of expression in most plant organs (U.S. Pat. No. 5,378,619, specifically incorporated herein by reference). Another set of preferred promoters are root enhanced or specific promoters such as the CaMV derived 4 as-1 promoter or the wheat POX1 promoter (U.S. Pat. No. 5,023,179, specifically incorporated herein by reference; Hertig et al., 1991). The root enhanced or specific promoters would be particularly preferred for the control of corn rootworm (*Diabroticus* spp.) in transgenic corn plants.

The promoters used in the DNA constructs (i.e. chimeric plant genes) of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis, etc. Furthermore, the promoters may be altered to contain multiple "enhancer sequences" to assist in elevating gene expression.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNA's, from suitable eucaryotic genes, or from a synthetic gene sequence. The present invention is not limited to constructs wherein the non-translated region is derived from the 5' non-translated sequence that accompanies the promoter sequence.

For optimized expression in monocotyledenous plants such as maize, an intron should also be included in the DNA expression construct. This intron would typically be placed near the 5' end of the mRNA in untranslated sequence. This intron could be obtained from, but not limited to, a set of introns consisting of the maize hsp70 intron (U.S. Pat. No. 5,424,412; specifically incorporated herein by reference) or the rice Act1 intron (McElroy et al., 1990). As shown below, the maize hsp70 intron is useful in the present invention.

As noted above, the 3' non-translated region of the chimeric plant genes of the present invention contains a polyadenylation signal which functions in plants to cause the addition of adenylate nucleotides to the 3' end of the RNA. Examples of preferred 3' regions are (1) the 3' transcribed, non-translated regions containing the polyadenylate signal of *Agrobacterium* tumor-inducing (Ti) plasmid genes, such as the nopaline synthase (NOS) gene and (2) plant genes such as the pea ssRUBISCO E9 gene (Fischhoff et al., 1987).

6.14.2 Plant Transformation and Expression

A plant gene containing a structural coding sequence of the present invention can be inserted into the genome of a plant by any suitable method. Suitable plant transformation vectors include those derived from a Ti plasmid of *Agrobacterium tumefaciens*, as well as those disclosed, e.g., by Herrera-Estrella (1983), Bevan (1983), Klee (1985) and Eur. Pat. Appl. Publ. No. EP0120516. In addition to plant transformation vectors derived from the Ti or root-inducing (Ri) plasmids of *Agrobacterium*, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen (Fromm et al., 1986; Armstrong et al., 1990; Fromm et al., 1990).

6.14.3 Construction of Monocot Plant Expression Vectors for Cry Genes

For efficient expression of cry genes in transgenic plants, the gene must have a suitable sequence composition (Diehn et al., 1996). To place the cry gene in a vector suitable for expression in monocotyledonous plants (i.e. under control of the enhanced Cauliflower Mosaic Virus 35S promoter and link to the hsp70 intron followed by a nopaline synthase polyadenylation site as in U.S. Pat. No. 5,424,412, specifically incorporated herein by reference), a vector such as pMON19469 may be used. Such a vector is conveniently digested with NcoI and EcoRI restriction enzymes. The larger vector band of approximately 4.6 kb is then electrophoresed, purified, and ligated with T4 DNA ligase to an NcoI-EcoRI fragment which contains the synthetic cry gene. The ligation mix is then transformed into E. coli, carbenicillin resistant colonies recovered and plasmid DNA recovered by DNA miniprep procedures. The DNA is then subjected to restriction endonuclease analysis with enzymes such as NcoI and EcoRI (together), NotI, and/or PstI individually or in combination, to identify clones containing the cry coding sequence fused to an intron such as the hsp70 intron, placed under the control of the enhanced CaMV35S promoter.

To place the gene in a vector suitable for recovery of stably transformed and insect resistant plants, the 3.75-kb NotI restriction fragment from pMON33708 containing the lysine oxidase coding sequence fused to the hsp70 intron under control of the enhanced CaMV35S promoter may be isolated by gel electrophoresis and purification. This fragment is then ligated with a vector such as pMON30460 which has been previously treated with NotI and calf intestinal alkaline phosphatase (pMON30460 contains the neomycin phosphotransferase coding sequence under control of the CaMV35S promoter). Kanamycin resistant colonies may then be obtained by transformation of this ligation mix into E. coli and colonies containing the desired plasmid may be identified by restriction endonuclease digestion of plasmid miniprep DNAs. Restriction enzymes such as NotI, EcoRV, HindIII, NcoI, EcoRI, and BglII may be used to identify the appropriate clones in which the orientation of both genes are in tandem (i.e. the 3' end of the cry expression cassette is linked to the 5' end of the nptII expression cassette). Expression of the Cry protein by the resulting plasmid in corn protoplasts may be confirmed by electroporation of the vector DNA into protoplasts followed by protein blot and ELISA analysis. This vector may be introduced into the genomic DNA of corn embryos by particle gun bombardment followed by paromomycin selection to obtain corn plants expressing the cry gene essentially as described in U.S. Pat. No. 5,424,412, specifically incorporated herein by reference.

As an example, the vector may be introduced via cobombardment with a hygromycin resistance conferring plasmid into immature embryo scutella (IES) of maize, followed by hygromycin selection, and regeneration. Transgenic corn lines expressing the cry protein may then be identified by ELISA analysis. Progeny seed from these events may then be subsequently tested for protection from insect feeding.

7.0 REFERENCES

The following references, to the extent that they provide exemplary procedural or other details supplementary to those set forth herein, are specifically incorporated herein by reference.

U.S. Pat. No. 4,196,265, issued Apr. 1, 1980.
U.S. Pat. No. 4,554,101, issued Nov. 19, 1985.
U.S. Pat. No. 4,683,195, issued Jul. 28, 1987.
U.S. Pat. No. 4,683,202, issued Jul. 28, 1987.
U.S. Pat. No. 4,757,011, issued Jul. 12, 1988.
U.S. Pat. No. 4,769,061, issued Sep. 6, 1988.
U.S. Pat. No. 4,940,835, issued Feb. 23, 1990.
U.S. Pat. No. 4,965,188, issued Oct. 23, 1990.
U.S. Pat. No. 4,971,908, issued Nov. 20, 1990.
U.S. Pat. No. 4,987,071, issued Jan. 22, 1991.
U.S. Pat. No. 5,023,179, issued Jun. 11, 1991.
U.S. Pat. No. 5,176,995, issued Oct. 15, 1991.
U.S. Pat. No. 5,334,711, issued Aug. 2, 1994.
U.S. Pat. No. 5,378,619, issued Jan. 3, 1995.
U.S. Pat. No. 5,384,253, issued Jan. 24, 1995.
U.S. Pat. No. 5,424,412, issued Jun. 13, 1995.
U.S. Pat. No. 5,463,175, issued Oct. 31, 1995.
U.S. Pat. No. 5,631,359, issued May 20, 1997.
Int. Pat. Appl. Publ. No. WO 84/02913.
Int. Pat. Appl. Publ. No. WO 91/03162.
Int. Pat. Appl. Publ. No. WO 92/07065.
Int. Pat. Appl. Publ. No. WO 93/15187.
Int. Pat. Appl. Publ. No. WO 93/23569.
Int. Pat. Appl. Publ. No. WO 94/02595.
Int. Pat. Appl. Publ. No. WO 94/13688.
Eur. Pat. Appl. Publ. No. EP0120516.
Eur. Pat. Appl. Publ. No. EP0360257.
Eur. Pat. Appl. Publ. No. 92110298.4
Arantes and Lereclus, *Gene,* 108:115-119, 1991.
Abdullah et al., *Biotechnology,* 4:1087, 1986.
Baum et al., *Appl. Environ. Microbiol.,* 56:3420-3428, 1990.
Benbrook et al., In: *Proceedings Bio Expo* 1986, Butterworth, Stoneham, Mass., pp. 27-54, 1986.
Bevan et al., *Nucleic Acids Res.,* 11 (2):369-85, 1983.
Bytebier et al., *Proc. Natl. Acad. Sci. USA,* 84:5345, 1987.
Callis et al., *Genes and Development,* 1:1183, 1987.
Campbell, "Monoclonal Antibody Technology, Laboratory Techniques in Biochemistry and Molecular Biology," Vol. 13, Burden and Von Knippenberg, Eds. pp. 75-83, Elsevier, Amsterdam, 1984.
Capecchi, "High efficiency transformation by direct microinjection of DNA into cultured mammalian cells," *Cell,* 22(2):479-488, 1980.
Cashmore et al., *Gen. Eng. of Plants,* Plenum Press, New York, 29-38, 1983.
Charles et al., *Annu. Rev. Entomol.,* 41:451-472, 1996.
Chau et al., *Science,* 244:174-181, 1989.
Chen et al., *Nucl. Acids Res.,* 20:4581-9, 1992.
Chowrira and Burke, *Nucl. Acids Res.,* 20:2835-2840, 1992.
Clapp, "Somatic gene therapy into hematopoietic cells. Current status and future implications," *Clin. Perinatol.,* 20(1): 155-168, 1993.
Collins and Olive, *Biochem.,* 32:2795-2799, 1993.
Conway and Wickens, In: *RNA Processing,* p. 40, Cold Spring Harbor Laboratory, Cold Spring Harbor, N.Y., 1988.
Cornelissen et al., *Nature,* 321(6069):531-2, 1986.
Crickmore et al., *Microbiol. Mol. Biol. Rev.* 62:807-813, 1998.
Cristou et al., *Plant Physiol.,* 87:671-674, 1988.
Curiel, Agarwal, Wagner, Cotten, "Adenovirus enhancement of transferrin-polylysine-mediated gene delivery," *Proc. Natl. Acad. Sci. USA,* 88(19):8850-8854, 1991.
Curiel, Wagner, Cotten, Birnstiel, Agarwal, Li, Loechel, Hu, "High-efficiency gene transfer mediated by adenovirus coupled to DNA-polylysine complexes," *Hum. Gen. Ther.,* 3(2):147-154, 1992.

Dean et al., *Nucl. Acids Res.*, 14(5):2229, 1986.
Dhir, S. K., Dhir, S., Hepburn, A., and Widholm, J. M., "Factors affecting transient gene expression in electroporated Glycine-max protoplasts," *Plant Cell Rep.*, 10(2):106-110, 1991.
Dhir, S. K., Dhir, S., Sturtevant, A. P., and Widholm, J. M., "Regeneration of transformed shoots for electroporated soybean *Glycine-max* L. Merr. Protoplasts, *Plant Cell Rep.*, 10(2):97-101, 1991.
Diehn et al., *Genet. Eng.* (N.Y.), 18:83-99, 1996.
Donovan et al., *J. Biol. Chem.* 263:561-567, 1988.
Donovan et al., *Appl. Environ. Microbiol.* 58:3921-3927, 1992.
Doyle et al., *J. Biol. Chem.*, 261(20):9228-38, 1986.
Dropulic et al., *J. Virol.*, 66:1432-41, 1992.
Eglitis and Anderson, "Retroviral vectors for introduction of genes into mammalian cells," *Biotechniques*, 6(7):608-614, 1988.
Eglitis, Kantoff, Kohn, Karson, Moen, Lothrop, Blaese, Anderson, "Retroviral-mediated gene transfer into hemopoietic cells," *Avd. Exp. Med. Biol.*, 241:19-27, 1988.
Elroy-Stein and Moss, *Proc. Natl. Acad. Sci. USA*, 87:6743-7, 1990.
English and Slatin, *Insect Biochem. Mol. Biol.*, 22:1-7, 1992.
Fraley et al., *Biotechnology*, 3:629, 1985.
Fraley et al., *Proc. Natl. Acad. Sci. USA*, 80:4803, 1983.
Fromm et al., *Biotechnology* (N.Y.), 8(9):833-9, 1990.
Fromm et al., *Nature*, 319:791-793, 1986.
Fromm, Taylor, Walbot, "Expression of genes transferred into monocot and dicot plant cells by electroporation," *Proc. Natl. Acad. Sci. USA*, 82(17):5824-5828, 1985.
Fujimura et al., *Plant Tiss. Cult. Lett.*, 2:74, 1985.
Fynan, Webster, Fuller, Haynes, Santoro, Robinson, "DNA vaccines: protective immunizations by parenteral, mucosal, and gene gun inoculations," *Proc. Natl. Acad. Sci. USA*, 90(24):11478-11482, 1993.
Gao and Huang, *Nucl. Acids Res.*, 21:2867-72, 1993.
Gefter et al., *Somat. Cell Genet.*, 3:231-236, 1977.
Genovese and Milcarek, In: *RNA Processing*, p. 62, Cold Spring Harbor Laboratory, Cold Spring Harbor, N.Y., 1988.
Gil and Proudfoot, *Nature*, 312:473, 1984.
Goding, "Monoclonal Antibodies: Principles and Practice," pp. 60-74. 2nd Edition, Academic Press, Orlando, Fla., 1986.
Graham and van der Eb, "Transformation of rat cells by DNA of human adenovirus 5," *Virology*, 54(2):536-539, 1973.
Guerrier-Takada et al., *Cell*, 35:849, 1983.
Hampel and Tritz, *Biochem.*, 28:4929, 1989.
Hampel et al., *Nucl. Acids Res.*, 18:299, 1990.
Harlow and Lane, "Antibodies: A Laboratory Manual," Cold Spring Harbor Laboratory, Cold Spring Harbor, N.Y., 1988.
Herrera-Estrella et al., *Embo. J*, 2(6):987-996, 1983.
Hertig et al., *Plant Mol. Biol.*, 16(1):171-4, 1991.
Hess, *Intern Rev. Cytol.*, 107:367, 1987.
Höfte et al., *Microbiol Rev.*, 53:242-255, 1989.
Horsch, R. B., Fry, J. E., Hoffmann, N. L., Eichholtz, D., Rogers, S. G., and Fraley, R. T., "A simple and general method for transferring genes into plants," *Science*, 227 (4691):1229-1231, 1985.
Jameson and Wolf, "The Antigenic Index: A Novel Algorithm for Predicting Antigenic Determinants," *Compu. Appl. Biosci.*, 4(1):181-6, 1988.
Johnston and Tang, "Gene gun transfection of animal cells and genetic immunization," *Methods Cell. Biol.*, 43(A): 353-365, 1994.
Jorgensen et al., *Mol. Gen. Genet.*, 207:471, 1987.
Kashani-Sabet et al., *Antisense Res. Dev.*, 2:3-15, 1992.
Keller et al., *EMBO J.*, 8:1309-14, 1989.
Klee, H. J., Yanofsky, M. F., and Nester, E. W., "Vectors for transformation of higher plants," *Bio-Technology*, 3(7):637-642, 1985.
Klein et al., *Nature*, 327:70, 1987.
Klein et al., *Proc. Natl. Acad. Sci. USA*, 85:8502-8505, 1988.
Kohler and Milstein, *Eur. J. Immunol.*, 6:511-519, 1976.
Kohler and Milstein, *Nature*, 256:495-497, 1975.
Kreig et al., In: *Zangew. Ent.*, 96:500-508, 1983. Kyte and Doolittle, A simple method for displaying the hydropathic character of a protein," *J. Mol. Biol.*, 157(1):105-132, 1982.
Lambert et al., *Appl. Environ. Microbiol.*, 58:2536-2642, 1992B.
Lambert et al., *Gene*, 110: 131-132, 1992A.
Langridge et al., *Proc. Natl. Acad. Sci. USA*, 86:3219-3223, 1989.
Lee et al., *Biochem. Biophys. Res. Comm.* 229:139-146.
L'Huillier et al., *EMBO J.*, 11:4411-8, 1992.
Lieber et al., *Methods Enzymol.*, 217:47-66, 1993.
Lindstrom et al., *Developmental Genetics*, 11:160, 1990.
Lisziewicz et al., *Proc. Natl. Acad. Sci. U.S.A.*, 90:8000-4, 1993.
Lorz et al., *Mol. Gen. Genet.*, 199:178, 1985.
Lu, Xiao, Clapp, Li, Broxmeyer, "High efficiency retroviral mediated gene transduction into single isolated immature and replatable CD34(3+) hematopoietic stem/progenitor cells from human umbilical cord blood," *J. Exp. Med.*, 178(6):2089-2096, 1993.
Luo et al., *Plant Mol. Biol. Reporter*, 6:165, 1988.
Maddock et al., *Third International Congress of Plant Molecular Biology*, Abstract 372, 1991.
Maloy et al., "Microbial Genetics" 2nd Edition. Jones and Barlett Publishers, Boston, Mass., 1994.
Maloy, S. R., "Experimental Techniques in Bacterial Genetics" Jones and Bartlett Publishers, Boston, Mass., 1990.
Maniatis et al., "Molecular Cloning: a Laboratory Manual," Cold Spring Harbor Laboratory, Cold Spring Harbor, N.Y., 1982.
Marcotte et al., *Nature*, 335:454, 1988.
McCabe et al., *Biotechnology*, 6:923, 1988.
McDevitt et al., *Cell*, 37:993-999, 1984.
McElroy, Zhang, Wu, "Isolation of an efficient promoter for use in rice transformation," *Plant Cell*, 2:163-171, 1990.
Mettus and Macaluso, *Appl. Environ. Microbiol.* 56:1128-1134, 1990
Neuhaus et al., *Theor. Appl. Genet.*, 75:30, 1987.
Odell et al., *Nature*, 313:810, 1985.
Ohkawa, Yuyama, Taira, "Activities of HIV-RNA targeted ribozymes transcribed from a 'shot-gun' type ribozyme-trimming plasmid," *Nucl. Acids Symp. Ser.*, 27:15-6, 1992.
Ojwang et al., *Proc. Natl. Acad. Sci. USA*, 89:10802-6, 1992.
Omirulleh et al., *Plant Mol. Biol.*, 21:415-428, 1993.
Pandey and Marzluff, In "RNA Processing," p. 133, Cold Spring Harbor Laboratory, Cold Spring Harbor, N.Y., 1987.
Pena et al., *Nature*, 325:274, 1987.
Perrault et al., *Nature*, 344:565, 1990.
Perrotta and Been, *Biochem.*, 31:16, 1992.
Pieken et al., *Science*, 253:314, 1991.
Poszkowski et al., *EMBO J.*, 3:2719, 1989.
Potrykus et al., *Mol. Gen. Genet.*, 199:183, 1985.
Poulsen et al., *Mol. Gen. Genet.*, 205:193-200, 1986.
Prokop and Bajpai, *Ann. N.Y. Acad. Sci.*, 646, 1991.

Rogers et al., *In: Methods For Plant Molecular Biology*, A. Weissbach and H.

Weissbach, eds., Academic Press Inc., San Diego, Calif. 1988.

Rogers et al., *Methods Enzymol.*, 153:253-277, 1987.

Rossi et al., *Aids Res. Hum. Retrovir.*, 8:183, 1992.

Sadofsky and Alwine, *Mol. Cell. Biol.*, 4(8):1460-1468, 1984.

Sambrook et al., "Antibodies: A Laboratory Manual," Cold Spring Harbor Laboratory, Cold spring Harbor, N.Y., 1989.

Sambrook et al., "Molecular Cloning: A Laboratory Manual," Cold Spring Harbor Laboratory, Cold Spring Harbor, N.Y., 1989.

Sanger et al., "DNA sequencing with chain-terminating inhibitors," *Proc. Natl. Acad. Sci. USA*, 74(12):5463-5467, 1977.

Sarver et al., *Science*, 247(4947):1222-5, 1990.

Saville and Collins, *Cell*, 61:685-696, 1990.

Saville and Collins, *Proc. Natl. Acad. Sci. USA*, 88:8826-8830, 1991.

Scanlon et al., *Proc. Natl. Acad. Sci. USA*, 88:10591-5, 1991.

Scaringe et al., *Nucl. Acids Res.*, 18:5433-5441, 1990.

Schnepf et al., *Microbiol. Mol. Biol. Rev.* 62:775-806, 1998.

Shaw and Kamen, *Cell*, 46:659-667, 1986. Shaw and Kamen, In: "RNA Processing", p. 220, Cold Spring Harbor Laboratory, Cold Spring Harbor, N.Y., 1987.

Sick et al., *Nucl. Acids Res.*, 18:1305, 1990.

Simpson, *Science*, 233:34, 1986.

Spielmann et al., *Mol. Gen. Genet.*, 205:34, 1986.

Taira et al., *Nucl. Acids Res.*, 19:5125-30, 1991.

Toriyama et al., *TheorAppl. Genet.*, 73:16, 1986.

Uchimiya et al., *Mol. Gen. Genet.*, 204:204, 1986.

Usman et al., *J. Am. Chem. Soc.*, 109:7845-7854, 1987.

Usman and Cedergren, *TIBS*, 17:34, 1992.

Van Tunen et al., *EMBO J*, 7:1257, 1988.

Vasil et al., "Herbicide-resistant fertile transgenic wheat plants obtained by microprojectile bombardment of regenerable embryogenic callus," *Biotechnology*, 10:667-674, 1992.

Vasil, *Biotechnology*, 6:397, 1988.

Ventura et al., *Nucl. Acids Res.*, 21:3249-55, 1993.

Vodkin et al., *Cell*, 34:1023, 1983.

Vogel, J. M., Dawe, R. K., and Freeling, M., "Regulation of the cell type-specific expression of maize Adhl and Shl electroporation-directed gene transfer into protoplasts of several maize tissues," *J. Cell. Biochem.*, (Suppl. 0) 13:Part D, 1989.

Von Tersch, M. A., Robbins, H. L., Jany, C. S., and Johnson, T., *Appl. Environ. Microbiol.* 57:349-358, 1991.

Wagner et al., "Coupling of adenovirus to transferrin-polylysine/DNA complexes greatly enhances receptor-mediated gene delivery and expression of transfected genes," *Proc. Natl. Acad. Sci. USA*, 89(13):6099-6103, 1992.

Weerasinghe et al., *J. Virol.*, 65:5531-4, 1991.

Weissbach and Weissbach, *Methods for Plant Molecular Biology*, (eds.), Academic Press, Inc., San Diego, Calif., 1988.

Wenzler et al., *Plant Mol. Biol.*, 12:41-50, 1989.

Wickens and Stephenson, *Science*, 226:1045, 1984.

Wickens et al., In: "RNA Processing," p. 9, Cold Spring Harbor Laboratory, Cold Spring Harbor, N.Y., 1987.

Widner, W. R., and Whiteley, H. R., *J. Bacteriol.*, 172:2826-2832, 1990.

Wong and Neumann, "Electric field mediated gene transfer," *Biochim. Biophys. Res. Commun.*, 107(2):584-587, 1982.

Woolf et al., *Proc. Natl. Acad. Sci. USA*, 89:7305-7309, 1992.

Yamada et al., *Plant Cell Rep.*, 4:85, 1986.

Yang et al., *Proc. Natl. Acad. Sci. USA*, 87:4144-48, 1990.

Yu et al., *Proc. Natl. Acad. Sci. USA*, 90:6340-4, 1993.

Zatloukal, Wagner, Cotten, Phillips, Plank, Steinlein, Curiel, Bimstiel, "Transferrinfection: a highly efficient way to express gene constructs in eukaryotic cells," *Ann. N. K Acad. Sci.*, 660:136-153, 1992.

Zhou et al., *Methods Enzymol.*, 101:433, 1983.

Zhou et al., *Mol. Cell. Biol.*, 10:4529-37, 1990.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. A transgenic plant having incorporated into its genome a polynucleotide encoding the polypeptide of SEQ ID NO:2 or an insecticidal fragment thereof operably linked to a plant-expressible promoter.

2. The transgenic plant of claim 1, further defined as a monocotyledonous plant.

3. The transgenic plant of claim 2, further defined as a corn, wheat, oat, rice, barley, turn grass, or pasture grass plant.

4. The transgenic plant of claim 1, further defined as a dicotyledonous plant.

5. The transgenic plant of claim 4, further defined as a legume, soybean, tobacco, tomato, potato, cotton, fruit, berry, vegetable or tree plant.

6. A progeny of any generation of the transgenic plant of claim 1, wherein said progeny comprises said polynucleotide.

7. A seed of any generation of the transgenic plant of claim 1, wherein said seed comprises said polynucleotide.

8. The transgenic plant of claim 1, wherein said polynucleotide is further operably linked to a polynucleotide encoding a signal peptide.

9. The transgenic plant of claim 8, wherein said signal peptide targets expression of said polypeptide or said insecticidal fragment to the chloroplast, endoplasmic reticulum, Golgi body or vacuole, or for secretion.

10. The transgenic plant of claim 9, wherein said signal peptide is a chloroplast transit peptide or a secretory signal peptide.

11. The transgenic plant of claim 1, wherein said plant-expressible promoter is selected from the group consisting of corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, Potato patatin, lectin, CaMV 35S, and the S-E9 small subunit RuBP carboxylase promoter.

12. A method of preparing an insect resistant plant, said method comprising:

(a) transforming recipient plant cells with a polynucleotide encoding the polypeptide of SEQ ID NO:2 or an insecticidal fragment thereof operably linked to a plant-expressible promoter;

(b) selecting a recipient plant cell comprising said polynucleotide; and (c) regenerating a plant from the selected recipient plant cell;

wherein said plant comprises said polynucleotide and is insect resistant.

13. The method of claim 12, wherein said polynucleotide is further operably linked to a polynucleotide encoding a signal peptide.

14. The method of claim 13, wherein said signal peptide is a chloroplast transit peptide or a secretory signal peptide.

15. The method of claim 12, wherein said plant-expressible promoter is selected from the group consisting of corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, Potato patatin, lectin, CaMV 35S, and the S-E9 small subunit RuBP carboxylase promoter.

16. A method for controlling Lepidopteran insect infestation in a field of crop plants, said method comprising growing plants comprising a polynucleotide encoding the polypeptide of SEQ ID NO:2, or a insecticidal fragment, thereof operably linked to a plant-expressible promoter.

17. The method of claim 16, wherein said polynucleotide is further operably linked to a polynucleotide encoding a signal peptide.

18. The method of claim 17, wherein said signal peptide is a chloroplast transit peptide or a secretory signal peptide.

19. The method of claim 16, wherein said plant-expressible promoter is selected from the group consisting of corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, Potato patatin, lectin, CaMV 35S, and the S-E9 small subunit RuBP carboxylase promoter.

* * * * *

UNITED STATES PATENT AND TRADEMARK OFFICE
CERTIFICATE OF CORRECTION

| | | |
|---|---|---|
| PATENT NO. | : 7,534,939 B2 | Page 1 of 1 |
| APPLICATION NO. | : 11/487813 | |
| DATED | : July 17, 2006 | |
| INVENTOR(S) | : James A. Baum et al. | |

It is certified that error appears in the above-identified patent and that said Letters Patent is hereby corrected as shown below:

In column 193, line 22, claim 3, delete the word "turn" and insert --turf--.

Signed and Sealed this

Fourteenth Day of July, 2009

JOHN DOLL
*Acting Director of the United States Patent and Trademark Office*

SEQUENCE LISTING

```
<160> NUMBER OF SEQ ID NOS: 63

<210> SEQ ID NO 1
<211> LENGTH: 1899
<212> TYPE: DNA
<213> ORGANISM: Bacillus thuringiensis
<220> FEATURE:
<221> NAME/KEY: CDS
<222> LOCATION: (1)..(1899)

<400> SEQUENCE: 1 atg a

| | | |
|---|---|---|
| aat gta gtg gcc cat gat cca ttt agt ttt gag cat aaa tca tta gat<br>Asn Val Val Ala His Asp Pro Phe Ser Phe Glu His Lys Ser Leu Asp<br>20 25 30 | 96 | |
| acc atc cga aaa gaa tgg atg gag tgg aaa aga aca gat cat agt tta<br>Thr Ile Arg Lys Glu Trp Met Glu Trp Lys Arg Thr Asp His Ser Leu<br>35 40 45 | 144 | |
| tat gta gct cct ata gtc gga act gtt tct agc ttt ctg cta aag aag<br>Tyr Val Ala Pro Ile Val Gly Thr Val Ser Ser Phe Leu Leu Lys Lys<br>50 55 60 | 192 | |
| gtg ggg agt ctt att gga aaa agg ata ttg agt gaa tta tgg ggg tta<br>Val Gly Ser Leu Ile Gly Lys Arg Ile Leu Ser Glu Leu Trp Gly Leu<br>65 70 75 80 | 240 | |
| ata ttt cct agt ggt agc aca aat cta atg caa gat att tta agg gag<br>Ile Phe Pro Ser Gly Ser Thr Asn Leu Met Gln Asp Ile Leu Arg Glu<br>85 90 95 | 288 | |
| aca gaa caa ttc cta aat caa aga ctt aat aca gac act ctt gcc cgt<br>Thr Glu Gln Phe Leu Asn Gln Arg Leu Asn Thr Asp Thr Leu Ala Arg<br>100 105 110 | 336 | |
| gta aat gcg gaa ttg gaa ggg ctg caa gcg aat ata agg gag ttt aat<br>Val Asn Ala Glu Leu Glu Gly Leu Gln Ala Asn Ile Arg Glu Phe Asn<br>115 120 125 | 384 | |
| caa caa gta gat aat ttt tta aat cct act caa aac cct gtt cct tta<br>Gln Gln Val Asp Asn Phe Leu Asn Pro Thr Gln Asn Pro Val Pro Leu<br>130 135 140 | 432 | |
| tca ata act tct tca gtt aat aca atg cag caa tta ttt cta aat aga<br>Ser Ile Thr Ser Ser Val Asn Thr Met Gln Gln Leu Phe Leu Asn Arg<br>145 150 155 160 | 480 | |
| tta ccc cag ttc cgt gtg caa gga tac caa ctg tta tta cct tta<br>Leu Pro Gln Phe Arg Val Gln Gly Tyr Gln Leu Leu Leu Pro Leu<br>165 170 175 | 528 | |
| ttt gca cag gca gcc aat atg cat ctt tct ttt att aga gat gtt gtt<br>Phe Ala Gln Ala Ala Asn Met His Leu Ser Phe Ile Arg Asp Val Val<br>180 185 190 | 576 | |
| ctc aat gca gat gaa tgg gga att tca gca gca aca tta cgt acg tat<br>Leu Asn Ala Asp Glu Trp Gly Ile Ser Ala Ala Thr Leu Arg Thr Tyr<br>195 200 205 | 624 | |
| caa aat tat ctg aaa aat tat aca aca gag tac tct aat tat tgt ata<br>Gln Asn Tyr Leu Lys Asn Tyr Thr Thr Glu Tyr Ser Asn Tyr Cys Ile<br>210 215 220 | 672 | |
| aat acg tat caa act gcg ttt aga ggt tta aac acc cgt tta cac gat<br>Asn Thr Tyr Gln Thr Ala Phe Arg Gly Leu Asn Thr Arg Leu His Asp<br>225 230 235 240 | 720 | |
| atg tta gaa ttt aga aca tat atg ttt tta aat gta ttt gaa tat gta<br>Met Leu Glu Phe Arg Thr Tyr Met Phe Leu Asn Val Phe Glu Tyr Val<br>245 250 255 | 768 | |
| tct atc tgg tcg ttg ttt aaa tat caa agc ctt cta gta tct tct ggc<br>Ser Ile Trp Ser Leu Phe Lys Tyr Gln Ser Leu Leu Val Ser Ser Gly<br>260 265 270 | 816 | |
| gct aat tta tat gca agc ggt agt gga cca cag cag act caa tca ttt<br>Ala Asn Leu Tyr Ala Ser Gly Ser Gly Pro Gln Gln Thr Gln Ser Phe<br>275 280 285 | 864 | |
| act tca caa gac tgg cca ttt tta tat tct ctt ttc caa gtt aat tca<br>Thr Ser Gln Asp Trp Pro Phe Leu Tyr Ser Leu Phe Gln Val Asn Ser<br>290 295 300 | 912 | |
| aat tat gtg tta aat ggc ttt agt ggc gct aga ctt acg cag act ttc<br>Asn Tyr Val Leu Asn Gly Phe Ser Gly Ala Arg Leu Thr Gln Thr Phe<br>305 310 315 320 | 960 | |
| cct aat att ggt ggt tta cct ggt act act aca act cac gca ttg ctt<br>Pro Asn Ile Gly Gly Leu Pro Gly Thr Thr Thr Thr His Ala Leu Leu<br>325 330 335 | 1008 | |

-continued

```
gcg gca agg gtc aat tac agt gga gga gtt tcg tct ggt gat ata ggc      1056
Ala Ala Arg Val Asn Tyr Ser Gly Gly Val Ser Ser Gly Asp Ile Gly
            340                 345                 350 gct gtg ttt aat caa aat ttt agt tgt agc aca ttt ctc cca cct ttg      1104
Ala Val Phe Asn Gln Asn Phe Ser Cys Ser Thr Phe Leu Pro Pro Leu
        355                 360                 365 tta aca cca ttt gtt agg agt tgg cta gat tca ggt tca gat cga ggg      1152
Leu Thr Pro Phe Val Arg Ser Trp Leu Asp Ser Gly Ser Asp Arg Gly
    370                 375                 380 ggt gtt aat acc gtt aca aat tgg caa aca gaa tcg ttt gag tca act      1200
Gly Val Asn Thr Val Thr Asn Trp Gln Thr Glu Ser Phe Glu Ser Thr
385                 390                 395                 400 tta ggt tta agg tgt ggt gct ttt aca gct cgt ggt aat tca aac tat      1248
Leu Gly Leu Arg Cys Gly Ala Phe Thr Ala Arg Gly Asn Ser Asn Tyr
                405                 410                 415 ttc cca gat tat ttt atc cgt aat att tca gga gtt cct tta gtt gtt      1296
Phe Pro Asp Tyr Phe Ile Arg Asn Ile Ser Gly Val Pro Leu Val Val
            420                 425                 430 aga aat gaa gat tta aga aga ccg tta cac tat aat gaa ata aga aat      1344
Arg Asn Glu Asp Leu Arg Arg Pro Leu His Tyr Asn Glu Ile Arg Asn
        435                 440                 445 ata gaa agt cct tca gga aca cct ggt gga tta cga gct tat atg gta      1392
Ile Glu Ser Pro Ser Gly Thr Pro Gly Gly Leu Arg Ala Tyr Met Val
    450                 455                 460 tct gtg cat aat aga aaa aat aat atc tat gcc gtg cat gaa aat ggt      1440
Ser Val His Asn Arg Lys Asn Asn Ile Tyr Ala Val His Glu Asn Gly
465                 470                 475                 480 act atg att cat tta gcg ccg gaa gat tat aca gga ttc acc ata tcg      1488
Thr Met Ile His Leu Ala Pro Glu Asp Tyr Thr Gly Phe Thr Ile Ser
                485                 490                 495 ccg ata cat gca act caa gtg aat aat caa acg cga aca ttt att tct      1536
Pro Ile His Ala Thr Gln Val Asn Asn Gln Thr Arg Thr Phe Ile Ser
            500                 505                 510 gaa aaa ttt gga aat caa ggt gat tcc tta aga ttt gaa caa agc aac      1584
Glu Lys Phe Gly Asn Gln Gly Asp Ser Leu Arg Phe Glu Gln Ser Asn
        515                 520                 525 acg aca gca cgt tat aca ctt aga gga aat gga aat agt tac aat ctt      1632
Thr Thr Ala Arg Tyr Thr Leu Arg Gly Asn Gly Asn Ser Tyr Asn Leu
    530                 535                 540 tat tta aga gta tct tca cta gga aat tcc act att cga gtt act ata      1680
Tyr Leu Arg Val Ser Ser Leu Gly Asn Ser Thr Ile Arg Val Thr Ile
545                 550                 555                 560 aac ggt agg gtt tat act gct tca aat gtt aat act act aca aat aac      1728
Asn Gly Arg Val Tyr Thr Ala Ser Asn Val Asn Thr Thr Thr Asn Asn
                565                 570                 575 gat gga gtt aat gat aat ggc gct cgt ttt tta gat att aat atg ggt      1776
Asp Gly Val Asn Asp Asn Gly Ala Arg Phe Leu Asp Ile Asn Met Gly
            580                 585                 590 aat gta gta gca agt gat aat act aat gta ccg tta gat ata aat gtg      1824
Asn Val Val Ala Ser Asp Asn Thr Asn Val Pro Leu Asp Ile Asn Val
        595                 600                 605 aca ttt aac tcc ggt act caa ttt gag ctt atg aat att atg ttt gtt      1872
Thr Phe Asn Ser Gly Thr Gln Phe Glu Leu Met Asn Ile Met Phe Val
    610                 615                 620 cca act aat ctt cca cca ata tat taa                                  1899
Pro Thr Asn Leu Pro Pro Ile Tyr
625                 630
```

<210> SEQ ID NO 2

-continued

```
<211> LENGTH: 632
<212> TYPE: PRT
<213> ORGANISM: Bacillus thuringiensis

<400> SEQUENCE: 2

Met Asn Asn Val Leu Asn Asn Gly Arg Thr Thr Ile Cys Asp Ala Tyr
1               5                   10                  15

Asn Val Val Ala His Asp Pro Phe Ser Phe Glu His Lys Ser Leu Asp
            20                  25                  30

Thr Ile Arg Lys Glu Trp Met Glu Trp Lys Arg Thr Asp His Ser Leu
        35                  40                  45

Tyr Val Ala Pro Ile Val Gly Thr Val Ser Ser Phe Leu Leu Lys Lys
    50                  55                  60

Val Gly Ser Leu Ile Gly Lys Arg Ile Leu Ser Glu Leu Trp Gly Leu
65                  70                  75                  80

Ile Phe Pro Ser Gly Ser Thr Asn Leu Met Gln Asp Ile Leu Arg Glu
                85                  90                  95

Thr Glu Gln Phe Leu Asn Gln Arg Leu Asn Thr Asp Thr Leu Ala Arg
            100                 105                 110

Val Asn Ala Glu Leu Glu Gly Leu Gln Ala Asn Ile Arg Glu Phe Asn
        115                 120                 125

Gln Gln Val Asp Asn Phe Leu Asn Pro Thr Gln Asn Pro Val Pro Leu
130                 135                 140

Ser Ile Thr Ser Ser Val Asn Thr Met Gln Gln Leu Phe Leu Asn Arg
145                 150                 155                 160

Leu Pro Gln Phe Arg Val Gln Gly Tyr Gln Leu Leu Leu Leu Pro Leu
                165                 170                 175

Phe Ala Gln Ala Ala Asn Met His Leu Ser Phe Ile Arg Asp Val Val
            180                 185                 190

Leu Asn Ala Asp Glu Trp Gly Ile Ser Ala Ala Thr Leu Arg Thr Tyr
        195                 200                 205

Gln Asn Tyr Leu Lys Asn Tyr Thr Thr Glu Tyr Ser Asn Tyr Cys Ile
    210                 215                 220

Asn Thr Tyr Gln Thr Ala Phe Arg Gly Leu Asn Thr Arg Leu His Asp
225                 230                 235                 240

Met Leu Glu Phe Arg Thr Tyr Met Phe Leu Asn Val Phe Glu Tyr Val
                245                 250                 255

Ser Ile Trp Ser Leu Phe Lys Tyr Gln Ser Leu Leu Val Ser Ser Gly
            260                 265                 270

Ala Asn Leu Tyr Ala Ser Gly Ser Gly Pro Gln Gln Thr Gln Ser Phe
        275                 280                 285

Thr Ser Gln Asp Trp Pro Phe Leu Tyr Ser Leu Phe Gln Val Asn Ser
    290                 295                 300

Asn Tyr Val Leu Asn Gly Phe Ser Gly Ala Arg Leu Thr Gln Thr Phe
305                 310                 315                 320

Pro Asn Ile Gly Gly Leu Pro Gly Thr Thr Thr His Ala Leu Leu
                325                 330                 335

Ala Ala Arg Val Asn Tyr Ser Gly Gly Val Ser Ser Gly Asp Ile Gly
            340                 345                 350

Ala Val Phe Asn Gln Asn Phe Ser Cys Ser Thr Phe Leu Pro Pro Leu
        355                 360                 365

Leu Thr Pro Phe Val Arg Ser Trp Leu Asp Ser Gly Ser Asp Arg Gly
    370                 375                 380

Gly Val Asn Thr Val Thr Asn Trp Gln Thr Glu Ser Phe Glu Ser Thr
```

```
                385                 390                 395                 400
Leu Gly Leu Arg Cys Gly Ala Phe Thr Ala Arg Gly Asn Ser Asn Tyr
                    405                 410                 415
Phe Pro Asp Tyr Phe Ile Arg Asn Ile Ser Gly Val Pro Leu Val Val
                420                 425                 430
Arg Asn Glu Asp Leu Arg Arg Pro Leu His Tyr Asn Glu Ile Arg Asn
            435                 440                 445
Ile Glu Ser Pro Ser Gly Thr Pro Gly Gly Leu Arg Ala Tyr Met Val
        450                 455                 460
Ser Val His Asn Arg Lys Asn Asn Ile Tyr Ala Val His Glu Asn Gly
465                 470                 475                 480
Thr Met Ile His Leu Ala Pro Glu Asp Tyr Thr Gly Phe Thr Ile Ser
                485                 490                 495
Pro Ile His Ala Thr Gln Val Asn Asn Gln Thr Arg Thr Phe Ile Ser
            500                 505                 510
Glu Lys Phe Gly Asn Gln Gly Asp Ser Leu Arg Phe Glu Gln Ser Asn
        515                 520                 525
Thr Thr Ala Arg Tyr Thr Leu Arg Gly Asn Gly Asn Ser Tyr Asn Leu
    530                 535                 540
Tyr Leu Arg Val Ser Ser Leu Gly Asn Ser Th

```
                                                 ccagaattc                                                          729
```

<210> SEQ ID NO 4
<211> LENGTH: 243
<212> TYPE: PRT
<213> ORGANISM: Bacillus thuringiensis

<400> SEQUENCE: 4

```
Phe Ala Arg Asn Gln Ala Ile Ser Arg Leu Glu Gly Leu Ser Asn Leu
1               5                   10                  15

Tyr Gln Ile Tyr Ala Glu Ser Phe Arg Glu Trp Glu Ala Asp Pro Thr
            20                  25                  30

Asn Pro Ala Leu Arg Glu Glu Met Arg Ile Gln Phe Asn Asp Met Asn
        35                  40                  45

Ser Ala Leu Thr Thr Ala Ile Pro Leu Leu Ala Val Gln Asn Tyr Gln
    50                  55                  60

Val Pro Leu Leu Ser Val Tyr Val Gln Ala Ala Asn Leu His Leu Ser
65                  70                  75                  80

Val Leu Arg Asp Val Ser Val Phe Gly Gln Arg Trp Gly Phe Asp Ala
                85                  90                  95

Ala Thr Ile Asn Ser Arg Tyr Asn Asp Leu Thr Arg Leu Ile Gly Asn
            100                 105                 110

Tyr Thr Asp Tyr Ala Val Arg Trp Tyr Asn Thr Gly Leu Glu Arg Val
        115                 120                 125

Trp Gly Pro Asp Ser Arg Asp Trp Val Arg Tyr Asn Gln Phe Arg Arg
    130                 135                 140

Glu Leu Thr Leu Thr Val Leu Asp Ile Val Ala Leu Phe Ser Asn Tyr
145                 150                 155                 160

Asp Ser Arg Arg Tyr Pro Ile Arg Thr Val Ser Gln Leu Thr Arg Glu
                165                 170                 175

Ile Tyr Thr Asn Pro Val Leu Glu Asn Phe Asp Gly Ser Phe Arg Gly
            180                 185                 190

Met Ala Gln Arg Ile Glu Gln Asn Ile Arg Gln Pro His Leu Met Asp
        195                 200                 205

Ile Leu Asn Ser Ile Thr Ile Tyr Thr Asp Val His Arg Gly Phe Asn
    210                 215                 220

Tyr Trp Ser Gly His Gln Ile Thr Ala Ser Pro Val Gly Phe Ser Gly
225                 230                 235                 240

Pro Glu Phe
```

<210> SEQ ID NO 5
<211> LENGTH: 1959
<212> TYPE: DNA
<213> ORGANISM: Bacillus thuringiensis

<400> SEQUENCE: 5

```
gaaaatgaga atgaaattat aaatgcctta tcgattccag ctgtatcgaa tcattccgca        60
caaatggatc tatcgctaga tgctcgtatt gaggattctt tgtgtatagc cgagggaat        120 aatatcaatc cacttgttag cgcatcaaca gtccaaacgg gtataaacat agctggtaga      180
atattgggcg tattaggtgt gccgtttgct ggacaactag ctagttttta tagttttctt      240
gttggggaat tatggcctag tggtagagat ccatgggaaa ttttcctgga atatgtgaaa      300
caacttataa gacaacaagt aacagaaaat actaggaata cggctattgc tcgattagaa      360
ggtctaggaa gaggctatag atcttaccag caggctcttg aaacttggtt agataaccga      420
```

```
aatgatgcaa gatcaagaag cattattctt gagcgctatg ttgctttaga acttgacatt    480
actactgcta taccgctttt cagaatacga atgaagaag ttccattatt aatggtatat    540
gctcaagctg caaatttaca cctattatta ttgagagacg catccctttt tggtagtgaa    600
tgggggatgg catcttccga tgttaaccaa tattaccagg aacaaatcag atatacagag    660
gaatattcta accattgcgt acaatggtat aatacagggc taaataactt aagagggaca    720
aatgctgaaa gttggttgcg gtataatcaa ttccgtagag acctaacgtt aggggtatta    780
gatttagtag ccctattccc aagctatgat actcgcactt atccaatcaa tacgagtgct    840
cagttaacaa gagaaattta tacagatcca attgggagaa caaatgcacc ttcaggattt    900
gcaagtacga attggtttaa taataatgca ccatcgtttt ctgccataga ggctgccatt    960
ttcaggcctc cgcatctact tgattttcca gaacaactta caatttacag tgcatcaagc   1020
cgttggagta gcactcaaca tatgaattat tgggtgggac ataggcttaa cttccgccca   1080
ataggaggga cattaaatac ctcaacacaa ggacttacta taatacttc aattaatcct   1140
gtaacattac attacgtttc gtctcgtgac gtttatagaa cagaatcaaa tgcagggaca   1200
aatatactat ttactactcc tgtgaatgga gtaccttggg ctagatttaa ttttataacc   1260
ctcagaatat ttatgaaaga ggcgccacta cctacagtca accgtatcag ggagttggga   1320
ttcaattatt tgattcagaa actgaattac caccagaaac aacagaacga ccaaattatg   1380
aatcatatag tcatagatat ctcatataga ctaatcatag gaaacacttt gagagcacca   1440
gtctattctt ggacgcatcg tagtgcagat cgtacgaata cgattggacc aaatagaatt   1500
actcaaattc ctgcagtgaa gggaagattt cttttttaatg gttctgtgat ttcaggacca   1560
ggatttactg gtggagacgt agttagattg aataggaata atggtaatat ccaaaataga   1620
gggtatattg aagttccaat tcaattcacg tcgacatcta ccagatatcg agttcgagta   1680
cgttatgctt ctgtaacctc gattgagctc aatgttaatt tgggcaattc atcaatttt    1740
acgaacacat taccagcaac agctgcatca ttagataatc tacaatcagg ggattttggt   1800
tatgttgaaa tcaacaatgc ttttacatcc gcaacaggta atatagtagg tgctagaaat   1860
tttagtgcaa atgcagaagt aataaatagac agatttgaat ttatcccagt tactgcaacc   1920
ttcgaggtag aatatgattt agaaagagca caaaaggcg                           1959
```

<210> SEQ ID NO 6
<211> LENGTH: 653
<212> TYPE: PRT
<213> ORGANISM: Bacillus thuringiensis

<400> SEQUENCE: 6

```
Glu Asn Glu Asn Glu Ile Ile Asn Ala Leu Ser Ile Pro Ala Val Ser
1               5                   10                  15

Asn His Ser Ala Gln Met Asp Leu Ser Leu Asp Ala Arg Ile Glu Asp
            20                  25                  30

Ser Leu Cys Ile Ala Glu Gly Asn Asn Ile Asn Pro Leu Val Ser Ala
        35                  40                  45

Ser Thr Val Gln Thr Gly Ile Asn Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Ser Gly Arg Asp Pro Trp Glu Ile Phe Leu
                85                  90                  95

Glu Tyr Val Glu Gln Leu Ile Arg Gln Gln Val Thr Glu Asn Thr Arg
```

-continued

```
                100                 105                 110
Asn Thr Ala Ile Ala Arg Leu Glu Gly Leu Gly Arg Gly Tyr Arg Ser
            115                 120                 125
Tyr Gln Gln Ala Leu Glu Thr Trp Leu Asp Asn Arg Asn Asp Ala Arg
        130                 135                 140
Ser Arg Ser Ile Ile Leu Glu Arg Tyr Val Ala Leu Glu Leu Asp Ile
145                 150                 155                 160
Thr Thr Ala Ile Pro Leu Phe Arg Ile Arg Asn Glu Glu Val Pro Leu
                165                 170                 175
Leu Met Val Tyr Ala Gln Ala Ala Asn Leu His Leu Leu Leu Leu Arg
            180                 185                 190
Asp Ala Ser Leu Phe Gly Ser Glu Trp Gly Met Ala Ser Ser Asp Val
        195                 200                 205
Asn Gln Tyr Tyr Gln Glu Gln Ile Arg Tyr Thr Glu Glu Tyr Ser Asn
    210                 215                 220
His Cys Val Gln Trp Tyr Asn Thr Gly Leu Asn Asn Leu Arg Gly Thr
225                 230                 235                 240
Asn Ala Glu Ser Trp Leu Arg Tyr Asn Gln Phe Arg Arg Asp Leu Thr
                245                 250                 255
Leu Gly Val Leu Asp Leu Val Ala Leu Phe Pro Ser Tyr Asp Thr Arg
            260                 265                 270
Thr Tyr Pro Ile Asn Thr Ser Ala Gln Leu Thr Arg Glu Ile Tyr Thr
        275                 280                 285
Asp Pro Ile Gly Arg Thr Asn Ala Pro Ser Gly Phe Ala Ser Thr Asn
    290                 295                 300
Trp Phe Asn Asn Asn Ala Pro Ser Phe Ser Ala Ile Glu Ala Ala Ile
305                 310                 315                 320
Phe Arg Pro Pro His Leu Leu Asp Phe Pro Glu Gln Leu Thr Ile Tyr
                325                 330                 335
Ser Ala Ser Ser Arg Trp Ser Ser Thr Gln His Met Asn Tyr Trp Val
            340                 345                 350
Gly His Arg Leu Asn Phe Arg Pro Ile Gly Gly Thr Leu Asn Thr Ser
        355                 360                 365
Thr Gln Gly Leu Thr Asn Asn Thr Ser Ile Asn Pro Val Thr Leu His
    370                 375                 380
Tyr Val Ser Ser Arg Asp Val Tyr Arg Thr Glu Ser Asn Ala Gly Thr
385                 390                 395                 400
Asn Ile Leu Phe Thr Thr Pro Val Asn Gly Val Pro Trp Ala Arg Phe
                405                 410                 415
Asn Phe Ile Thr Leu Arg Ile Phe Met Lys Glu Ala Pro Leu Pro Thr
            420                 425                 430
Val Asn Arg Ile Arg Glu Leu Gly Phe Asn Tyr Leu Ile Gln Lys Leu
        435                 440                 445
Asn Tyr His Gln Lys Gln Asn Asp Gln Ile Met Asn His Ile Val
    450                 455                 460
Ile Asp Ile Ser Tyr Arg Leu Ile Ile Gly Asn Thr Leu Arg Ala Pro
465                 470                 475                 480
Val Tyr Ser Trp Thr His Arg Ser Ala Asp Arg Thr Asn Thr Ile Gly
                485                 490                 495
Pro Asn Arg Ile Thr Gln Ile Pro Ala Val Lys Gly Arg Phe Leu Phe
            500                 505                 510
Asn Gly Ser Val Ile Ser Gly Pro Gly Phe Thr Gly Gly Asp Val Val
        515                 520                 525
```

-continued

Arg Leu Asn Arg Asn Asn Gly Asn Ile Gln Asn Arg Gly Tyr Ile Glu
            530                 535                 540

Val Pro Ile Gln Phe Thr Ser Thr Ser Thr Arg Tyr Arg Val Arg Val
545                 550                 555                 560

Arg Tyr Ala Ser Val Thr Ser Ile Glu Leu Asn Val Asn Leu Gly Asn
                565                 570                 575

Ser Ser Ile Phe Thr Asn Thr Leu Pro Ala Thr Ala Ala Ser Leu Asp
            580                 585                 590

Asn Leu Gln Ser Gly Asp Phe Gly Tyr Val Glu Ile Asn Asn Ala Phe
            595                 600                 605

Thr Ser Ala Thr Gly Asn Ile Val Gly Ala Arg Asn Phe Ser Ala Asn
            610                 615                 620

Ala Glu Val Ile Ile Asp Arg Phe Glu Phe Ile Pro Val Thr Ala Thr
625                 630                 635                 640

Phe Glu Val Glu Tyr Asp Leu Glu Arg Ala Gln Lys Ala
                645                 650

<210> SEQ ID NO 7
<211> LENGTH: 328
<212> TYPE: DNA
<213> ORGANISM: Bacillus thuringiensis

<400> SEQUENCE: 7
ctttacagga agattaccac aaagttatta tatcgtttcc gttatgcttc gggagcaaat      60
aggagtggtt cattaagtta ttcacagcaa acttcgtatg taatttcatt tccaaaaact     120
atggacgcag gtgaaccact aacatctcgt tcgttcgctt ttacaacaac cgtcactcca     180
atagccttta cacgagctca agaagaattt gatttataca tccaacagaa tgtttatata     240
gatagagttg aatttatccc agtagatgca acatttgagg caaaatctga tttagaaaga     300
gcgaaaaagg cggtgaatgc cttgttta                                       328

<210> SEQ ID NO 8
<211> LENGTH: 109
<212> TYPE: PRT
<213> ORGANISM: Bacillus thuringiensis

<400> SEQUENCE: 8

Leu Tyr Arg Lys Ile Thr Thr Lys Leu Leu Tyr Arg Phe Arg Tyr Ala
1               5                   10                  15

Ser Gly Ala Asn Arg Ser Gly Ser Leu Ser Tyr Ser Gln Gln Thr Ser
                20                  25                  30

Tyr Val Ile Ser Phe Pro Lys Thr Met Asp Ala Gly Glu Pro Leu Thr
            35                  40                  45

Ser Arg Ser Phe Ala Phe Thr Thr Thr Val Thr Pro Ile Ala Phe Thr
        50                  55                  60

Arg Ala Gln Glu Glu Phe Asp Leu Tyr Ile Gln Gln Asn Val Tyr Ile
65                  70                  75                  80

Asp Arg Val Glu Phe Ile Pro Val Asp Ala Thr Phe Glu Ala Lys Ser
                85                  90                  95

Asp Leu Glu Arg Ala Lys Lys Ala Val Asn Ala Leu Phe
            100                 105

<210> SEQ ID NO 9
<211> LENGTH: 340
<212> TYPE: DNA
<213> ORGANISM: Bacillus thuringiensis

<400> SEQUENCE: 9

```
ttacgagtaa cctttacagg aagattacca caaagttatt atatacgttt ccgttatgct      60
tcgggagcaa ataggagtgg ttcattaagt tattcacagc aaacttcgta tgtaatttca     120
tttccaaaaa ctatggacgc aggtgaacca ctaacatctc gttcgttcgc ttttacaaca     180
accgtcactc caataacctt tacacgagct caagaagaat tgatttata catccaacag      240
aatgtttata tagatagagt tgaatttatc ccagtagatg caacatttga ggcaaaatct     300
gatttagaaa gagcgaaaaa ggcggtgaat gccttgttta                           340
```

<210> SEQ ID NO 10
<211> LENGTH: 113
<212> TYPE: PRT
<213> ORGANISM: Bacillus thuringiensis

<400> SEQUENCE: 10

```
Leu Arg Val Thr Phe Thr Gly Arg Leu Pro Gln Ser Tyr Tyr Ile Arg
 1               5                  10                  15
Phe Arg Tyr Ala Ser Gly Ala Asn Arg Ser Gly Ser Leu Ser Tyr Ser
                20                  25                  30
Gln Gln Thr Ser Tyr Val Ile Ser Phe Pro Lys Thr Met Asp Ala Gly
            35                  40                  45
Glu Pro Leu Thr Ser Arg Ser Phe Ala Phe Thr Thr Val Thr Pro
        50                  55                  60
Ile Thr Phe Thr Arg Ala Gln Glu Glu Phe Asp Leu Tyr Ile Gln Gln
65                  70                  75                  80
Asn Val Tyr Ile Asp Arg Val Glu Phe Ile Pro Val Asp Ala Thr Phe
                85                  90                  95
Glu Ala Lys Ser Asp Leu Glu Arg Ala Lys Lys Ala Val Asn Ala Leu
            100                 105                 110
Phe
```

<210> SEQ ID NO 11
<211> LENGTH: 306
<212> TYPE: DNA
<213> ORGANISM: Bacillus thuringiensis

<400> SEQUENCE: 11

```
gtatcgcgtg agatcgtatg ctctacgaca gatttacaat tctatacgaa tattaatgga      60
actactatta atattggtaa tttctcgagc actatggaca gtggggatga tttacagtac     120
ggaagattca gggttgcagg ttttactact ccatttacct tttcagatgc aaacagcaca     180
ttcacaatag gtgctttttgg cttctctcca acaacgaag tttatataga tcgaattgaa      240
tttgtcccgg cagaagtaac atttgaggca gaatatgatt tagagaaagc tcagaaagcg     300
gtgaat                                                                306
```

<210> SEQ ID NO 12
<211> LENGTH: 102
<212> TYPE: PRT
<213> ORGANISM: Bacillus thuringiensis

<400> SEQUENCE: 12

```
Val Ser Arg Glu Ile Val Cys Ser Thr Thr Asp Leu Gln Phe Tyr Thr
 1               5                  10                  15
Asn Ile Asn Gly Thr Thr Ile Asn Ile Gly Asn Phe Ser Thr Met
                20                  25                  30
```

Asp Ser Gly Asp Asp Leu Gln Tyr Gly Arg Phe Arg Val Ala Gly Phe
            35                  40                  45

Thr Thr Pro Phe Thr Phe Ser Asp Ala Asn Ser Thr Phe Thr Ile Gly
    50                  55                  60

Ala Phe Gly Phe Ser Pro Asn Asn Glu Val Tyr Ile Asp Arg Ile Glu
65                  70                  75                  80

Phe Val Pro Ala Glu Val Thr Phe Glu Ala Glu Tyr Asp Leu Glu Lys
                85                  90                  95

Ala Gln Lys Ala Val Asn
            100

<210> SEQ ID NO 13
<211> LENGTH: 279
<212> TYPE: DNA
<213> ORGANISM: Bacillus thuringiensis

<400> SEQUENCE: 13
caattccata catcaattga cggaagacct attaatcagg ggaatttttc agcaactatg     60
agtagtggga gtaatttaca gtccggaagc tttaggactg taggttttac tactccgttt    120
aacttttcaa atggatcaag tgtatttacg ttaagtgctc atgtcttcaa ttcaggcaat    180
gaagtttata tagatcgaat tgaatttatt ccggcagaag taacctttga ggcagaatat    240
gatttagaaa gagcacaaaa ggcggtgaat gagctgttt                           279

<210> SEQ ID NO 14
<211> LENGTH: 93
<212> TYPE: PRT
<213> ORGANISM: Bacillus thuringiensis

<400> SEQUENCE: 14

Gln Phe His Thr Ser Ile Asp Gly Arg Pro Ile Asn Gln Gly Asn Phe
1               5                   10                  15

Ser Ala Thr Met Ser Ser Gly Ser Asn Leu Gln Ser Gly Ser Phe Arg
            20                  25                  30

Thr Val Gly Phe Thr Thr Pro Phe Asn Phe Ser Asn Gly Ser Ser Val
            35                  40                  45

Phe Thr Leu Ser Ala His Val Phe Asn Ser Gly Asn Glu Val Tyr Ile
    50                  55                  60

Asp Arg Ile Glu Phe Ile Pro Ala Glu Val Thr Phe Glu Ala Glu Tyr
65                  70                  75                  80

Asp Leu Glu Arg Ala Gln Lys Ala Val Asn Glu Leu Phe
                85                  90

<210> SEQ ID NO 15
<211> LENGTH: 397
<212> TYPE: DNA
<213> ORGANISM: Bacillus thuringiensis

<400> SEQUENCE: 15
aggaccaggt tttacaggtg ggatatcctt cgaagaacga atgttggtag ctttggagat     60
atgcgtgtaa acattactgc accactatca caaagatatc gcgtaagaat tcgctatgct    120
tctacgacag atttacaatt ttcacgagaa tcaatggaac ttctgtaaaa tcaaggtaat    180
ttccaaagaa ctatgaatag agggggtaat ttagaatctg gaaactttag gactgcagga    240
tttagtacgc ctttagtttt ttcaaatgcg caaagtaca ttcacattgg gtactcaggc    300
ttttcaaatc aggaagttta tatagatcga attgaatttg tcccggcaga agtaacattc    360

```
gaggcagaat ctgatttgga aagagcgcaa aaggcgg                                    397
```

<210> SEQ ID NO 16
<211> LENGTH: 132
<212> TYPE: PRT
<213> ORGANISM: Bacillus thuringiensis

<400> SEQUENCE: 16

```
Arg Thr Arg Phe Tyr Arg Trp Asp Ile Leu Arg Arg Thr Asn Val Gly
1               5                   10                  15

Ser Phe Gly Asp Met Arg Val Asn Ile Thr Ala Pro Leu Ser Gln Arg
            20                  25                  30

Tyr Arg Val Arg Ile Arg Tyr Ala Ser Thr Thr Asp Leu Gln Phe Phe
        35                  40                  45

Thr Arg Ile Asn Gly Thr Ser Val Asn Gln Gly Asn Phe Gln Arg Thr
    50                  55                  60

Met Asn Arg Gly Gly Asn Leu Glu Ser Gly Asn Phe Arg Thr Ala Gly
65                  70                  75                  80

Phe Ser Thr Pro Phe Ser Phe Phe Lys Cys Ala Lys Tyr Ile His Ile
                85                  90                  95

Gly Tyr Ser Gly Phe Ser Asn Gln Glu Val Tyr Ile Asp Arg Ile Glu
            100                 105                 110

Phe Val Pro Ala Glu Val Thr Phe Glu Ala Glu Ser Asp Leu Glu Arg
        115                 120                 125

Ala Gln Lys Ala
    130
```

<210> SEQ ID NO 17
<211> LENGTH: 123
<212> TYPE: DNA
<213> ORGANISM: Bacillus thuringiensis

<400> SEQUENCE: 17

```
ataatctaca atcagggga ttttggttat gttgaaatca acaatgcttt tacatccgca     60
acaggtaata tagtaggtgc tagaaatttt acgtgcaaat gcagaagtaa aatagacag   120 att                                                                 123
```

<210> SEQ ID NO 18
<211> LENGTH: 41
<212> TYPE: PRT
<213> ORGANISM: Bacillus thuringiensis

<400> SEQUENCE: 18

```
Ile Ile Tyr Asn Gln Gly Asp Phe Gly Tyr Val Glu Ile Asn Asn Ala
1               5                   10                  15

Phe Thr Ser Ala Thr Gly Asn Ile Val Gly Ala Arg Asn Phe Thr Cys
            20                  25                  30

Lys Cys Arg Ser Asn Asn Arg Gln Ile
        35                  40
```

<210> SEQ ID NO 19
<211> LENGTH: 192
<212> TYPE: DNA
<213> ORGANISM: Bacillus thuringiensis

<400> SEQUENCE: 19

```
agttattata tacgtttccg ttatgcttcc gtagctaata ggagtggtat atttagctat    60
```

-continued

```
tcacagccaa cttcatatgg aatttccttt ccaaaaacta tggatgcaga tgaatcatta      120
acatctcgtt catttgcact tgctacactt gctacaccgc taaccttag aaggcaagaa       180 gaattaaatc ta                                                          192
```

<210> SEQ ID NO 20
<211> LENGTH: 64
<212> TYPE: PRT
<213> ORGANISM: Bacillus thuringiensis

<400> SEQUENCE: 20

```
Ser Tyr Tyr Ile Arg Phe Arg Tyr Ala Ser Val Ala Asn Arg Ser Gly
1               5                   10                  15

Ile Phe Ser Tyr Ser Gln Pro Thr Ser Tyr Gly Ile Ser Phe Pro Lys
            20                  25                  30

Thr Met Asp Ala Asp Glu Ser Leu Thr Ser Arg Ser Phe Ala Leu Ala
        35                  40                  45

Thr Leu Ala Thr Pro Leu Thr Phe Arg Arg Gln Glu Glu Leu Asn Leu
    50                  55                  60
```

<210> SEQ ID NO 21
<211> LENGTH: 3507
<212> TYPE: DNA
<213> ORGANISM: Bacillus thuringiensis
<220> FEATURE:
<221> NAME/KEY: CDS
<222> LOCATION: (1)..(3507)

<400> SEQUENCE: 21

```
atg gag ata aat aat cag aac caa tgc ata cca tat aat tgc tta agt       48
Met Glu Ile Asn Asn Gln Asn Gln Cys Ile Pro Tyr Asn Cys Leu Ser
1               5                   10                  15 aat cct gag gaa gta ttt ttg gat ggg gag agg ata tta cct gat atc       96
Asn Pro Glu Glu Val Phe Leu Asp Gly Glu Arg Ile Leu Pro Asp Ile
            20                  25                  30 gat cca ctc gaa gtt tct ttg tcg ctt ttg caa ttt ctt ttg aat aac       144
Asp Pro Leu Glu Val Ser Leu Ser Leu Leu Gln Phe Leu Leu Asn Asn
        35                  40                  45 ttt gtt cca ggg ggg ggg ttt att tca gga tta ctt gat aaa ata tgg       192
Phe Val Pro Gly Gly Gly Phe Ile Ser Gly Leu Leu Asp Lys Ile Trp
    50                  55                  60 ggg gct ttg aga cca tct gat tgg gaa tta ttt ctt gca cag att gaa      240
Gly Ala Leu Arg Pro Ser Asp Trp Glu Leu Phe Leu Ala Gln Ile Glu
65                  70                  75                  80 cag ttg att gat cga aga ata gaa aga aca gta aga gca aaa gca atc      288
Gln Leu Ile Asp Arg Arg Ile Glu Arg Thr Val Arg Ala Lys Ala Ile
                85                  90                  95 gct gaa tta gaa ggt tta ggg aga agt tat caa cta tat gga gag gca      336
Ala Glu Leu Glu Gly Leu Gly Arg Ser Tyr Gln Leu Tyr Gly Glu Ala
            100                 105                 110 ttt aaa gag tgg gaa aaa act cca gat aac aca gcg gct cgg tct aga      384
Phe Lys Glu Trp Glu Lys Thr Pro Asp Asn Thr Ala Ala Arg Ser Arg
        115                 120                 125 gta act gag aga ttt cgt ata att gat gct caa att gaa gca aat atc      432
Val Thr Glu Arg Phe Arg Ile Ile Asp Ala Gln Ile Glu Ala Asn Ile
    130                 135                 140 cct tcg ttt cgg gtt tcc gga ttt gaa gtg cca ctt cta ttg gtt tat      480
Pro Ser Phe Arg Val Ser Gly Phe Glu Val Pro Leu Leu Leu Val Tyr
145                 150                 155                 160 acc caa gca gct aat ttg cat ctc gct cta tta aga gat tct gtt gtt      528
Thr Gln Ala Ala Asn Leu His Leu Ala Leu Leu Arg Asp Ser Val Val
```

-continued

```
                   165                     170                     175
ttt gga gag aga tgg gga ttg acg act aca aat gtc aat gat atc tat    576
Phe Gly Glu Arg Trp Gly Leu Thr Thr Thr Asn Val Asn Asp Ile Tyr
                180                     185                     190 aat aga caa gtt aat aga att ggt gaa tat agc aag cat tgt gta gat    624
Asn Arg Gln Val Asn Arg Ile Gly Glu Tyr Ser Lys His Cys Val Asp
        195                     200                     205 acg tat aaa aca gaa tta gaa cgt cta gga ttt aga tct ata gcg caa    672
Thr Tyr Lys Thr Glu Leu Glu Arg Leu Gly Phe Arg Ser Ile Ala Gln
    210                     215                     220 tgg aga ata tat aat cag ttt aga agg gaa ttg aca cta acg gta tta    720
Trp Arg Ile Tyr Asn Gln Phe Arg Arg Glu Leu Thr Leu Thr Val Leu
225                     230                     235                     240 gat att gtc gct gtt ttc ccg aac tat gat agt aga ctg tat ccg att    768
Asp Ile Val Ala Val Phe Pro Asn Tyr Asp Ser Arg Leu Tyr Pro Ile
                245                     250                     255 cga aca att tct caa ttg aca aga gaa att tat aca tcc cca gta agc    816
Arg Thr Ile Ser Gln Leu Thr Arg Glu Ile Tyr Thr Ser Pro Val Ser
        260                     265                     270 gaa ttt tat tat ggt gtc att aat agt aat aat ata att ggt acc ctt    864
Glu Phe Tyr Tyr Gly Val Ile Asn Ser Asn Asn Ile Ile Gly Thr Leu
    275                     280                     285 act gaa cag caa ata agg cga cca cat ctt atg gac ttc ttt aac tcc    912
Thr Glu Gln Gln Ile Arg Arg Pro His Leu Met Asp Phe Phe Asn Ser
290                     295                     300 atg atc atg tat acg tca gat aat aga cga gaa cat tat tgg tca gga    960
Met Ile Met Tyr Thr Ser Asp Asn Arg Arg Glu His Tyr Trp Ser Gly
305                     310                     315                     320 ctt gaa atg acg gct act aat act gag gga cat caa agg tca ttc cct   1008
Leu Glu Met Thr Ala Thr Asn Thr Glu Gly His Gln Arg Ser Phe Pro
                325                     330                     335 tta gct ggg act ata ggg aat tca gct cca cca gta act gtt aga aat   1056
Leu Ala Gly Thr Ile Gly Asn Ser Ala Pro Pro Val Thr Val Arg Asn
        340                     345                     350 aat ggt gag gga att tat aga ata tta tcg gaa cca ttt tat tca gca   1104
Asn Gly Glu Gly Ile Tyr Arg Ile Leu Ser Glu Pro Phe Tyr Ser Ala
    355                     360                     365 cct ttt cta ggc aca agt gtg cta gga agt cgt ggg gaa gaa ttt gct   1152
Pro Phe Leu Gly Thr Ser Val Leu Gly Ser Arg Gly Glu Glu Phe Ala
370                     375                     380 ttt gca tct aat act act aca agt ctg cca tct aca ata tat aga aat   1200
Phe Ala Ser Asn Thr Thr Thr Ser Leu Pro Ser Thr Ile Tyr Arg Asn
385                     390                     395                     400 cgt gga aca gta gat tca tta gtc agc ata ccg cca cag gat tat agc   1248
Arg Gly Thr Val Asp Ser Leu Val Ser Ile Pro Pro Gln Asp Tyr Ser
                405                     410                     415 gta cca ccg cac agg ggg tat agt cat tta tta agt cac gtt acg atg   1296
Val Pro Pro His Arg Gly Tyr Ser His Leu Leu Ser His Val Thr Met
        420                     425                     430 cgc aat agt tct cct ata ttc cac tgg aca cat cgt agt gca acc cct   1344
Arg Asn Ser Ser Pro Ile Phe His Trp Thr His Arg Ser Ala Thr Pro
    435                     440                     445 aga aat aca att gat cca gat agt atc act caa att cca gca gtt aag   1392
Arg Asn Thr Ile Asp Pro Asp Ser Ile Thr Gln Ile Pro Ala Val Lys
450                     455                     460 gga gcg tat att ttt aat agt cca gtc att act ggg cca gga cat aca   1440
Gly Ala Tyr Ile Phe Asn Ser Pro Val Ile Thr Gly Pro Gly His Thr
465                     470                     475                     480 ggt ggg gat ata ata agg ttt aac cct aat act cag aac aac ata aga   1488
```

-continued

```
Gly Gly Asp Ile Ile Arg Phe Asn Pro Asn Thr Gln Asn Asn Ile Arg
            485                 490                 495 att cca ttt caa tca aat gcg gta cag cgt tat cga att aga atg cgt    1536
Ile Pro Phe Gln Ser Asn Ala Val Gln Arg Tyr Arg Ile Arg Met Arg
        500                 505                 510 tat gcg gca gaa gct gat tgt att tta gaa agt gga gta aac att gtt    1584
Tyr Ala Ala Glu Ala Asp Cys Ile Leu Glu Ser Gly Val Asn Ile Val
            515                 520                 525 act ggg gca ggg gtc acc ttt agg cca att cct att aaa gct aca atg    1632
Thr Gly Ala Gly Val Thr Phe Arg Pro Ile Pro Ile Lys Ala Thr Met
        530                 535                 540 act cct gga agt cct tta aca tat tac agc ttc cag tat gca gat tta    1680
Thr Pro Gly Ser Pro Leu Thr Tyr Tyr Ser Phe Gln Tyr Ala Asp Leu
545                 550                 555                 560 aat ata aat ctt act gcg ccg ata aga cct aat aat ttt gta tct att    1728
Asn Ile Asn Leu Thr Ala Pro Ile Arg Pro Asn Asn Phe Val Ser Ile
            565                 570                 575 aga cgt tca aac caa cca gga aac ctt tat ata gat aga att gaa ttc    1776
Arg Arg Ser Asn Gln Pro Gly Asn Leu Tyr Ile Asp Arg Ile Glu Phe
        580                 585                 590 att cca att gac cca atc cgt gag gca gaa cat gat tta gaa aga gcg    1824
Ile Pro Ile Asp Pro Ile Arg Glu Ala Glu His Asp Leu Glu Arg Ala
            595                 600                 605 caa aag gcg gtg aat gcg ctg ttt act tct tcc aat caa cta gga tta    1872
Gln Lys Ala Val Asn Ala Leu Phe Thr Ser Ser Asn Gln Leu Gly Leu
        610                 615                 620 aaa aca gat gtg acg gat tat cat att gat caa gtg tcc aat tta gtt    1920
Lys Thr Asp Val Thr Asp Tyr His Ile Asp Gln Val Ser Asn Leu Val
625                 630                 635                 640 gcg tgt tta tcg gat gaa ttc tgc ctg gat gaa aag cga gaa ttg tcc    1968
Ala Cys Leu Ser Asp Glu Phe Cys Leu Asp Glu Lys Arg Glu Leu Ser
            645                 650                 655 gag aaa gtt aaa cat gcg aag cga ctc agt gat gag aga aat tta ctc    2016
Glu Lys Val Lys His Ala Lys Arg Leu Ser Asp Glu Arg Asn Leu Leu
        660                 665                 670 caa gat caa aac ttt aca ggc atc aat agg caa gta gac cgt ggg tgg    2064
Gln Asp Gln Asn Phe Thr Gly Ile Asn Arg Gln Val Asp Arg Gly Trp
            675                 680                 685 aga gga agt acg gat att acc atc caa gga ggg aat gat gta ttc aaa    2112
Arg Gly Ser Thr Asp Ile Thr Ile Gln Gly Gly Asn Asp Val Phe Lys
        690                 695                 700 gag aat tac gtc aca cta cca ggt acc ttt gat gag tgt tac cca acg    2160
Glu Asn Tyr Val Thr Leu Pro Gly Thr Phe Asp Glu Cys Tyr Pro Thr
705                 710                 715                 720 tat ttg tat caa aaa ata gat gag tca aaa tta aaa cct tat act cgc    2208
Tyr Leu Tyr Gln Lys Ile Asp Glu Ser Lys Leu Lys Pro Tyr Thr Arg
            725                 730                 735 tat gaa tta aga ggg tat att gaa gat agt caa gac tta gaa gtc tat    2256
Tyr Glu Leu Arg Gly Tyr Ile Glu Asp Ser Gln Asp Leu Glu Val Tyr
        740                 745                 750 ttg atc cgt tac aat gca aaa cac gaa acg tta aat gtg cca ggt acg    2304
Leu Ile Arg Tyr Asn Ala Lys His Glu Thr Leu Asn Val Pro Gly Thr
            755                 760                 765 ggt tcc tta tgg cca ctt gca gcc gaa agt tca atc ggg agg tgc ggc    2352
Gly Ser Leu Trp Pro Leu Ala Ala Glu Ser Ser Ile Gly Arg Cys Gly
        770                 775                 780 gaa ccg aat cga tgc gcg cca cat att gaa tgg aat cct gaa cta gat    2400
Glu Pro Asn Arg Cys Ala Pro His Ile Glu Trp Asn Pro Glu Leu Asp
785                 790                 795                 800
```

```
tgt tcg tgt agg gat gga gaa aaa tgt gca cat cat tct cat cat ttc    2448
Cys Ser Cys Arg Asp Gly Glu Lys Cys Ala His His Ser His His Phe
            805                 810                 815 tcc ttg gat att gat gtt gga tgt aca gac tta aat gag gat tta ggt    2496
Ser Leu Asp Ile Asp Val Gly Cys Thr Asp Leu Asn Glu Asp Leu Gly
            820                 825                 830 gta tgg gtg ata ttt aag att aag acg caa gat ggc tat gca aga cta    2544
Val Trp Val Ile Phe Lys Ile Lys Thr Gln Asp Gly Tyr Ala Arg Leu
            835                 840                 845 gga aat tta gag ttt ctc gaa gag aaa cca ttg tta gga gaa gcg cta    2592
Gly Asn Leu Glu Phe Leu Glu Glu Lys Pro Leu Leu Gly Glu Ala Leu
850                 855                 860 gct cgt gtg aag aga gcg gag aaa aaa tgg aga gac aaa cgc gac aaa    2640
Ala Arg Val Lys Arg Ala Glu Lys Lys Trp Arg Asp Lys Arg Asp Lys
865                 870                 875                 880 ttg gaa tgg gaa aca aat att gtt tat aaa gag gca aaa gaa tct gta    2688
Leu Glu Trp Glu Thr Asn Ile Val Tyr Lys Glu Ala Lys Glu Ser Val
                885                 890                 895 gat gct tta ttc gta gat tct caa tat aat aga tta caa acg gat acg    2736
Asp Ala Leu Phe Val Asp Ser Gln Tyr Asn Arg Leu Gln Thr Asp Thr
            900                 905                 910 aac att gcg atg att cat gtg gca gat aaa cgc gtt cat cga atc cga    2784
Asn Ile Ala Met Ile His Val Ala Asp Lys Arg Val His Arg Ile Arg
            915                 920                 925 gaa gcg tat ttg cca gag tta tct gtg att ccg ggt gtc aat gcg gct    2832
Glu Ala Tyr Leu Pro Glu Leu Ser Val Ile Pro Gly Val Asn Ala Ala
            930                 935                 940 att ttc gaa gaa tta gaa ggt ctt att ttc act gca ttc tcc cta tat    2880
Ile Phe Glu Glu Leu Glu Gly Leu Ile Phe Thr Ala Phe Ser Leu Tyr
945                 950                 955                 960 gat gcg aga aat gtc att aaa aac gga gat ttc aat cat ggt tta tca    2928
Asp Ala Arg Asn Val Ile Lys Asn Gly Asp Phe Asn His Gly Leu Ser
                965                 970                 975 tgc tgg aac gtg aaa ggg cat gta gat gta gaa gaa caa aat aac cac    2976
Cys Trp Asn Val Lys Gly His Val Asp Val Glu Glu Gln Asn Asn His
            980                 985                 990 cgt tcg gtc ctt gtt gtt ccg gaa tgg gaa gca gaa gtg tca caa gaa    3024
Arg Ser Val Leu Val Val Pro Glu Trp Glu Ala Glu Val Ser Gln Glu
            995                1000                1005 gtc cgc gta tgt cca gga cgt ggc tat atc ctg cgt gtt aca gcg       3069
Val Arg Val Cys Pro Gly Arg Gly Tyr Ile Leu Arg Val Thr Ala
1010                1015                1020 tac aaa gag ggc tac gga gaa gga tgc gta acg atc cat gaa att       3114
Tyr Lys Glu Gly Tyr Gly Glu Gly Cys Val Thr Ile His Glu Ile
1025                1030                1035 gaa gat cat aca gac gaa ctg aaa ttt aga aac tgt gaa gaa gag       3159
Glu Asp His Thr Asp Glu Leu Lys Phe Arg Asn Cys Glu Glu Glu
1040                1045                1050 gaa gtg tat ccg aat aac acg gta acg tgt aat gat tat cca gca       3204
Glu Val Tyr Pro Asn Asn Thr Val Thr Cys Asn Asp Tyr Pro Ala
1055                1060                1065 aat caa gaa gaa tac agg gct gcg gaa act tcc cgt aat cgt gga       3249
Asn Gln Glu Glu Tyr Arg Ala Ala Glu Thr Ser Arg Asn Arg Gly
1070                1075                1080 tat ggc gaa tct tat gaa agt aat tct tcc ata cca gct gag tat       3294
Tyr Gly Glu Ser Tyr Glu Ser Asn Ser Ser Ile Pro Ala Glu Tyr
1085                1090                1095 gcg cca att tat gag aaa gca tat aca gat gga aga aaa gag aat       3339
Ala Pro Ile Tyr Glu Lys Ala Tyr Thr Asp Gly Arg Lys Glu Asn
1100                1105                1110
```

```
tct tgt gaa tct aac aga gga tat gga aat tac aca ccg tta cca      3384
Ser Cys Glu Ser Asn Arg Gly Tyr Gly Asn Tyr Thr Pro Leu Pro
    1115                1120                1125 gca ggt tat gtg aca aaa gaa tta gag tac ttc cca gaa acc gat      3429
Ala Gly Tyr Val Thr Lys Glu Leu Glu Tyr Phe Pro Glu Thr Asp
1130                1135                1140 aag gta tgg ata gag att gga gaa acg gaa gga aca ttc atc gta      3474
Lys Val Trp Ile Glu Ile Gly Glu Thr Glu Gly Thr Phe Ile Val
        1145                1150                1155 gac agt gtg gaa tta ctc ctc atg gag gaa tag                      3507
Asp Ser Val Glu Leu Leu Leu Met Glu Glu
1160                1165
```

<210> SEQ ID NO 22
<211> LENGTH: 1168
<212> TYPE: PRT
<213> ORGANISM: Bacillus thuringiensis

<400> SEQUENCE: 22

```
Met Glu Ile Asn Asn Gln Asn Gln Cys Ile Pro Tyr Asn Cys Leu Ser
1               5                   10                  15

Asn Pro Glu Glu Val Phe Leu Asp Gly Glu Arg Ile Leu Pro Asp Ile
            20                  25                  30

Asp Pro Leu Glu Val Ser Leu Ser Leu Leu Gln Phe Leu Leu Asn Asn
        35                  40                  45

Phe Val Pro Gly Gly Gly Phe Ile Ser Gly Leu Leu Asp Lys Ile Trp
    50                  55                  60

Gly Ala Leu Arg Pro Ser Asp Trp Glu Leu Phe Leu Ala Gln Ile Glu
65                  70                  75                  80

Gln Leu Ile Asp Arg Arg Ile Glu Arg Thr Val Arg Ala Lys Ala Ile
                85                  90                  95

Ala Glu Leu Glu Gly Leu Gly Arg Ser Tyr Gln Leu Tyr Gly Glu Ala
            100                 105                 110

Phe Lys Glu Trp Glu Lys Thr Pro Asp Asn Thr Ala Ala Arg Ser Arg
        115                 120                 125

Val Thr Glu Arg Phe Arg Ile Ile Asp Ala Gln Ile Glu Ala Asn Ile
    130                 135                 140

Pro Ser Phe Arg Val Ser Gly Phe Glu Val Pro Leu Leu Leu Val Tyr
145                 150                 155                 160

Thr Gln Ala Ala Asn Leu His Leu Ala Leu Leu Arg Asp Ser Val Val
                165                 170                 175

Phe Gly Glu Arg Trp Gly Leu Thr Thr Thr Asn Val Asn Asp Ile Tyr
            180                 185                 190

Asn Arg Gln Val Asn Arg Ile Gly Glu Tyr Ser Lys His Cys Val Asp
        195                 200                 205

Thr Tyr Lys Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Val Phe Pro Asn Tyr Asp Ser Arg Leu Tyr Pro Ile
                245                 250                 255

Arg Thr Ile Ser Gln Leu Thr Arg Glu Ile Tyr Thr Ser Pro Val Ser
            260                 265                 270

Glu Phe Tyr Tyr Gly Val Ile Asn Ser Asn Asn Ile Ile Gly Thr Leu
        275                 280                 285
```

```
Thr Glu Gln Gln Ile Arg Arg Pro His Leu Met Asp Phe Asn Ser
    290                 295                 300
Met Ile Met Tyr Thr Ser Asp Asn Arg Arg Glu His Tyr Trp Ser Gly
305                 310                 315                 320
Leu Glu Met Thr Ala Thr Asn Thr Glu Gly His Gln Arg Ser Phe Pro
                325                 330                 335
Leu Ala Gly Thr Ile Gly Asn Ser Ala Pro Pro Val Thr Val Arg Asn
            340                 345                 350
Asn Gly Glu Gly Ile Tyr Arg Ile Leu Ser Glu Pro Phe Tyr Ser Ala
        355                 360                 365
Pro Phe Leu Gly Thr Ser Val Leu Gly Ser Arg Gly Glu Glu Phe Ala
    370                 375                 380
Phe Ala Ser Asn Thr Thr Thr Ser Leu Pro Ser Thr Ile Tyr Arg Asn
385                 390                 395                 400
Arg Gly Thr Val Asp Ser Leu Val Ser Ile Pro Pro Gln Asp Tyr Ser
                405                 410                 415
Val Pro Pro His Arg Gly Tyr Ser His Leu Leu Ser His Val Thr Met
            420                 425                 430
Arg Asn Ser Ser Pro Ile Phe His Trp Thr His Arg Ser Ala Thr Pro
        435                 440                 445
Arg Asn Thr Ile Asp Pro Asp Ser Ile Thr Gln Ile Pro Ala Val Lys
    450                 455                 460
Gly Ala Tyr Ile Phe Asn Ser Pro Val Ile Thr Gly Pro Gly His Thr
465                 470                 475                 480
Gly Gly Asp Ile Ile Arg Phe Asn Pro Asn Thr Gln Asn Asn Ile Arg
                485                 490                 495
Ile Pro Phe Gln Ser Asn Ala Val Gln Arg Tyr Arg Ile Arg Met Arg
            500                 505                 510
Tyr Ala Ala Glu Ala Asp Cys Ile Leu Glu Ser Gly Val Asn Ile Val
        515                 520                 525
Thr Gly Ala Gly Val Thr Phe Arg Pro Ile Pro Ile Lys Ala Thr Met
    530                 535                 540
Thr Pro Gly Ser Pro Leu Thr Tyr Tyr Ser Phe Gln Tyr Ala Asp Leu
545                 550                 555                 560
Asn Ile Asn Leu Thr Ala Pro Ile Arg Pro Asn Asn Phe Val Ser Ile
                565                 570                 575
Arg Arg Ser Asn Gln Pro Gly Asn Leu Tyr Ile Asp Arg Ile Glu Phe
            580                 585                 590
Ile Pro Ile Asp Pro Ile Arg Glu Ala Glu His Asp Leu Glu Arg Ala
        595                 600                 605
Gln Lys Ala Val Asn Ala Leu Phe Thr Ser Ser Asn Gln Leu Gly Leu
    610                 615                 620
Lys Thr Asp Val Thr Asp Tyr His Ile Asp Gln Val Ser Asn Leu Val
625                 630                 635                 640
Ala Cys Leu Ser Asp Glu Phe Cys Leu Asp Glu Lys Arg Glu Leu Ser
                645                 650                 655
Glu Lys Val Lys His Ala Lys Arg Leu Ser Asp Glu Arg Asn Leu Leu
            660                 665                 670
Gln Asp Gln Asn Phe Thr Gly Ile Asn Arg Gln Val Asp Arg Gly Trp
        675                 680                 685
Arg Gly Ser Thr Asp Ile Thr Ile Gln Gly Gly Asn Asp Val Phe Lys
    690                 695                 700
Glu Asn Tyr Val Thr Leu Pro Gly Thr Phe Asp Glu Cys Tyr Pro Thr
```

```
                705                 710                 715                 720
Tyr Leu Tyr Gln Lys Ile Asp Glu Ser Lys Leu Lys Pro Tyr Thr Arg
                725                 730                 735
Tyr Glu Leu Arg Gly Tyr Ile Glu Asp Ser Gln Asp Leu Glu Val Tyr
                740                 745                 750
Leu Ile Arg Tyr Asn Ala Lys His Glu Thr Leu Asn Val Pro Gly Thr
                755                 760                 765
Gly Ser Leu Trp Pro Leu Ala Ala Glu Ser Ser Ile Gly Arg Cys Gly
                770                 775                 780
Glu Pro Asn Arg Cys Ala Pro His Ile Glu Trp Asn Pro Glu Leu Asp
785                 790                 795                 800
Cys Ser Cys Arg Asp Gly Glu Lys Cys Ala His His Ser His His Phe
                805                 810                 815
Ser Leu Asp Ile Asp Val Gly Cys Thr Asp Leu Asn Glu Asp Leu Gly
                820                 825                 830
Val Trp Val Ile Phe Lys Ile Lys Thr Gln Asp Gly Tyr Ala Arg Leu
                835                 840                 845
Gly Asn Leu Glu Phe Leu Glu Glu Lys Pro Leu Leu Gly Glu Ala Leu
                850                 855                 860
Ala Arg Val Lys Arg Ala Glu Lys Lys Trp Arg Asp Lys Arg Asp Lys
865                 870                 875                 880
Leu Glu Trp Glu Thr Asn Ile Val Tyr Lys Glu Ala Lys Glu Ser Val
                885                 890                 895
Asp Ala Leu Phe Val Asp Ser Gln Tyr Asn Arg Leu Gln Thr Asp Thr
                900                 905                 910
Asn Ile Ala Met Ile His Val Ala Asp Lys Arg Val His Arg Ile Arg
                915                 920                 925
Glu Ala Tyr Leu Pro Glu Leu Ser Val Ile Pro Gly Val Asn Ala Ala
                930                 935                 940
Ile Phe Glu Glu Leu Glu Gly Leu Ile Phe Thr Ala Phe Ser Leu Tyr
945                 950                 955                 960
Asp Ala Arg Asn Val Ile Lys Asn Gly Asp Phe Asn His Gly Leu Ser
                965                 970                 975
Cys Trp Asn Val Lys Gly His Val Asp Val Glu Glu Gln Asn Asn His
                980                 985                 990
Arg Ser Val Leu Val Val Pro Glu Trp Glu Ala Glu Val Ser Gln Glu
                995                 1000                1005
Val Arg Val Cys Pro Gly Arg Gly Tyr Ile Leu Arg Val Thr Ala
                1010                1015                1020
Tyr Lys Glu Gly Tyr Gly Glu Gly Cys Val Thr Ile His Glu Ile
                1025                1030                1035
Glu Asp His Thr Asp Glu Leu Lys Phe Arg Asn Cys Glu Glu Glu
                1040                1045                1050
Glu Val Tyr Pro Asn Asn Thr Val Thr Cys Asn Asp Tyr Pro Ala
                1055                1060                1065
Asn Gln Glu Glu Tyr Arg Ala Ala Glu Thr Ser Arg Asn Arg Gly
                1070                1075                1080
Tyr Gly Glu Ser Tyr Glu Ser Asn Ser Ser Ile Pro Ala Glu Tyr
                1085                1090                1095
Ala Pro Ile Tyr Glu Lys Ala Tyr Thr Asp Gly Arg Lys Glu Asn
                1100                1105                1110
Ser Cys Glu Ser Asn Arg Gly Tyr Gly Asn Tyr Thr Pro Leu Pro
                1115                1120                1125
```

Ala Gly Tyr Val Thr Lys Glu Leu Glu Tyr Phe Pro Glu Thr Asp
    1130                1135                1140

Lys Val Trp Ile Glu Ile Gly Glu Thr Glu Gly Thr Phe Ile Val
    1145                1150                1155

Asp Ser Val Glu Leu Leu Leu Met Glu Glu
    1160                1165

<210> SEQ ID NO 23
<211> LENGTH: 348
<212> TYPE: DNA
<213> ORGANISM: Bacillus thuringiensis

<400> SEQUENCE: 23
aataatagag gtcatcttcc aattccaatc caattttctt cgcgttctac cagatatcga      60
gttcgtgtac gttatgcttc tgcaaccccc attcaagtca atgttcattg ggaaaatagc     120
tcgttttttt caggtacagt accagctacg gctcagtcat tagataatct acaatcaaac     180
aattttggtt actttgagac cgctaatact atttcatctt cattagatgg tatagtaggt     240
attagaaatt ttagtgcaaa tgcagatttg ataatagaca gatttgaatt tatcccagtg     300
gatgcaacct ccgaggcaga acatgattta gaaagagcgc aaaaggcg                  348

<210> SEQ ID NO 24
<211> LENGTH: 116
<212> TYPE: PRT
<213> ORGANISM: Bacillus thuringiensis

<400> SEQUENCE: 24

Asn Asn Arg Gly His Leu Pro Ile Pro Ile Gln Phe Ser Ser Arg Ser
1               5                   10                  15

Thr Arg Tyr Arg Val Arg Val Arg Tyr Ala Ser Ala Thr Pro Ile Gln
            20                  25                  30

Val Asn Val His Trp Glu Asn Ser Ser Phe Phe Ser Gly Thr Val Pro
        35                  40                  45

Ala Thr Ala Gln Ser Leu Asp Asn Leu Gln Ser Asn Asn Phe Gly Tyr
    50                  55                  60

Phe Glu Thr Ala Asn Thr Ile Ser Ser Ser Leu Asp Gly Ile Val Gly
65                  70                  75                  80

Ile Arg Asn Phe Ser Ala Asn Ala Asp Leu Ile Ile Asp Arg Phe Glu
                85                  90                  95

Phe Ile Pro Val Asp Ala Thr Ser Glu Ala Glu His Asp Leu Glu Arg
            100                 105                 110

Ala Gln Lys Ala
        115

<210> SEQ ID NO 25
<211> LENGTH: 186
<212> TYPE: DNA
<213> ORGANISM: Bacillus thuringiensis

<400> SEQUENCE: 25
ccactaacat ctcgttcgtt cgctcataca acactcttca ctccaataac cttttcacga      60
gctcaagaag aatttgatct atacatccaa tcgggtgttt atatagatcg aattgaattt     120
attccagtta ctgcaacatt tgaggcagaa tatgatttag aaagagcgca aagggcggtg     180
aatgcc                                                                186

```
<210> SEQ ID NO 26
<211> LENGTH: 62
<212> TYPE: PRT
<213> ORGANISM: Bacillus thuringiensis

<400> SEQUENCE: 26

Pro Leu Thr Ser Arg Ser Phe Ala His Thr Thr Leu Phe Thr Pro Ile
1               5                   10                  15

Thr Phe Ser Arg Ala Gln Glu Glu Phe Asp Leu Tyr Ile Gln Ser Gly
            20                  25                  30

Val Tyr Ile Asp Arg Ile Glu Phe Ile Pro Val Thr Ala Thr Phe Glu
        35                  40                  45

Ala Glu Tyr Asp Leu Glu Arg Ala Gln Arg Ala Val Asn Ala
    50                  55                  60

<210> SEQ ID NO 27
<211> LENGTH: 3471
<212> TYPE: DNA
<213> ORGANISM: Bacillus thuringiensis

<400> SEQUENCE: 27
atgaatcgaa ataatcaaaa tgaatatgaa attattgatg ccccccattg tgggtgtcca      60
tcagatgacg atgtgaggta tcctttggca agtgacccaa atgcagcgtt acaaaatatg     120
aactataaag attacttaca aatgacagat gaggactaca ctgattctta tataaatcct    180
agtttatcta ttagtggtag agatgcagtt cagactgcgc ttactgttgt tgggagaata    240
ctcggggctt taggtgttcc gttttctgga caaatagtga gttttttatca attccttttta  300 aatacactgt ggccagttaa tgatacagct atatgggaag ctttcatgcg acaggtggag    360
gaacttgtca atcaacaaat aacagaattt gcaagaaatc aggcacttgc aagattgcaa    420
ggattaggag actcttttaa tgtatatcaa cgttccccttc aaaattggtt ggctgatcga    480
aatgatacac gaaatttaag tgttgttcgt gctcaattta tagctttaga ccttgatttt    540
gttaatgcta ttccattgtt tgcagtaaat ggacagcagg ttccattact gtcagtatat    600
gcacaagctg taaatttaca tttgttatta ttaaaagatg catctctttt tggagaagga    660
tggggattca cacaggggga aatttccaca tattatgacc gtcaattgga actaaccgct    720
aagtacacta attactgtga aacttggtat aatacaggtt tagatcgttt aagaggaaca    780
aatactgaaa gttggttaag atatcatcaa ttccgtagag aaatgacttt agtggtatta    840
gatgttgtgg cgctatttcc atattatgat gtacgacttt atccaacggg atcaaaccca    900
cagcttacac gtgaggtata tacagatccg attgtattta atccaccagc taatgttgga    960
ctttgccgac gttggggtac taatccctat aatactttt ctgagctcga aaatgccttc   1020
attcgcccac cacatctttt tgataggctg aatagcttaa caatcagcag taatcgattt   1080
ccagtttcat ctaattttat ggattattgg tcaggacata cgttacgccg tagttatctg   1140
aacgattcag cagtacaaga agatagttat ggcctaatta caaccacaag agcaacaatt   1200
aatcctggag ttgatggaac aaaccgcata gagtcaacgg cagtagattt tcgttctgca   1260
ttgataggta tatatggcgt gaatagagct tcttttgtcc caggaggctt gtttaatggt   1320
acgacttctc ctgctaatgg aggatgtaga gatctctatg atacaaatga tgaattacca   1380
ccagatgaaa gtaccggaag ttctacccat agactatctc atgttacctt ttttagtttt   1440
caaactaatc aggctggatc tatagctaat gcaggaagtg tacctactta tgtttggacc   1500
cgtcgtgatg tggaccttaa taatacgatt accccaaata gaattacaca attaccattg   1560
```

```
gtaaaggcat ctgcacctgt tcgggtact acggtcttaa aaggtccagg atttacagga      1620 ggggtatac tccgaagaac aactaatggc acatttggaa cgttaagagt aacagttaat      1680
tcaccattaa cacaaagata tcgcgtaaga gttcgttttg cttcatcagg aaatttcagc    1740
ataaggatac tgcgtggaaa tacctctata gcttatcaaa gatttgggag tacaatgaac    1800
agaggacagg aactaactta cgaatcattt gtcacaagtg agttcactac taatcagagc    1860
gatctgccct ttacatttac acaagctcaa gaaaatttaa caatccttgc agaaggtgtt    1920
agcaccggta gtgaatattt tatagataga attgaaatca tccctgtgaa cccggcacga    1980
gaagcagaag aggatttaga agcagcgaag aaagcgtgg cgaacttgtt tacacgtaca    2040
agggacggat tacaggtaaa tgtgacagat tatcaagtgg accaagcggc aaatttagtg    2100
tcatgcttat ccgatgaaca atatgggcat gacaaaaaga tgttattgga agcggtaaga    2160
gcggcaaaac gcctcagccg cgaacgcaac ttacttcaag atccagattt taatacaatc    2220
aatagtacag aagagaatgg ctggaaggca agtaacggtg ttactattag cgagggcggt    2280
ccattcttta aaggtcgtgc acttcagtta gcaagcgcaa gagaaaatta tccaacatac    2340
atttatcaaa aagtagatgc atcggtgtta aagcccttata cacgctatag actagatgga    2400
tttgtgaaga gtagtcaaga tttagaaatt gatctcatcc accatcataa agtccatctt    2460
gtaaaaaatg taccagataa tttagtatct gatacttact cagatggttc ttgcagcgga    2520
atcaaccgtt gtgatgaaca gcatcaggta gatatgcagc tagatgcgga gcatcatcca    2580
atggattgct gtgaagcggc tcaaacacat gagtttcctt cctatattaa tacaggggat    2640
ctaaatgcaa gtgtagatca gggcatttgg gttgtattaa aagttcgaac aacagatggg    2700
tatgcgacgt taggaaatct tgaattggta gaggttgggc cattatcggg tgaatctcta    2760
gaacgggaac aaagagataa tgcgaaatgg aatgcagagc taggaagaaa acgtgcagaa    2820
atagatcgtg tgtatttagc tgcgaaacaa gcaattaatc atctgtttgt agactatcaa    2880
gatcaacaat taaatccaga aattgggcta gcagaaatta atgaagcttc aaatcttgta    2940
gagtcaattt cgggtgtata tagtgataca ctattacaga ttcctgggat taactacgaa    3000
atttacacag agttatccga tcgcttacaa caagcatcgt atctgtatac gtctagaaat    3060
gcggtgcaaa atggagactt taacagtggt ctagatagtt ggaatacaac tatggatgca    3120
tcggttcagc aagatggcaa tatgcatttc ttagttcttt cgcattggga tgcacaagtt    3180
tcccaacaat tgagagtaaa tccgaattgt aagtatgtct tacgtgtgac agcaagaaaa    3240
gtaggaggcg gagatggata cgtcacaatc cgagatggcg ctcatcacca agaaactctt    3300
acatttaatg catgtgacta cgatgtaaat ggtacgtatg tcaatgacaa ttcgtatata    3360
acagaagaag tggtattcta cccagagaca aaacatatgt gggtagaggt gagtgaatcc    3420
gaaggttcat tctatataga cagtattgag tttattgaaa cacaagagta g             3471
```

<210> SEQ ID NO 28
<211> LENGTH: 1156
<212> TYPE: PRT
<213> ORGANISM: Bacillus thuringiensis

<400> SEQUENCE: 28

Met Asn Arg Asn Asn Gln Asn Glu Tyr Glu Ile Ile Asp Ala Pro His
1               5                   10                  15

Cys Gly Cys Pro Ser Asp Asp Asp Val Arg Tyr Pro Leu Ala Ser Asp
                20                  25                  30

Pro Asn Ala Ala Leu Gln Asn Met Asn Tyr Lys Asp Tyr Leu Gln Met

-continued

```
                35                  40                  45
Thr Asp Glu Asp Tyr Thr Asp Ser Tyr Ile Asn Pro Ser Leu Ser Ile
 50                  55                  60

Ser Gly Arg Asp Ala Val Gln Thr Ala Leu Thr Val Val Gly Arg Ile
 65                  70                  75                  80

Leu Gly Ala Leu Gly Val Pro Phe Ser Gly Gln Ile Val Ser Phe Tyr
                 85                  90                  95

Gln Phe Leu Leu Asn Thr Leu Trp Pro Val Asn Asp Thr Ala Ile Trp
                100                 105                 110

Glu Ala Phe Met Arg Gln Val Glu Glu Leu Val Asn Gln Gln Ile Thr
                115                 120                 125

Glu Phe Ala Arg Asn Gln Ala Leu Ala Arg Leu Gln Gly Leu Gly Asp
                130                 135                 140

Ser Phe Asn Val Tyr Gln Arg Ser Leu Gln Asn Trp Leu Ala Asp Arg
145                 150                 155                 160

Asn Asp Thr Arg Asn Leu Ser Val Val Arg Ala Gln Phe Ile Ala Leu
                165                 170                 175

Asp Leu Asp Phe Val Asn Ala Ile Pro Leu Phe Ala Val Asn Gly Gln
                180                 185                 190

Gln Val Pro Leu Leu Ser Val Tyr Ala Gln Ala Val Asn Leu His Leu
                195                 200                 205

Leu Leu Leu Lys Asp Ala Ser Leu Phe Gly Glu Gly Trp Gly Phe Thr
                210                 215                 220

Gln Gly Glu Ile Ser Thr Tyr Tyr Asp Arg Gln Leu Glu Leu Thr Ala
225                 230                 235                 240

Lys Tyr Thr Asn Tyr Cys Glu Thr Trp Tyr Asn Thr Gly Leu Asp Arg
                245                 250                 255

Leu Arg Gly Thr Asn Thr Glu Ser Trp Leu Arg Tyr His Gln Phe Arg
                260                 265                 270

Arg Glu Met Thr Leu Val Val Leu Asp Val Val Ala Leu Phe Pro Tyr
                275                 280                 285

Tyr Asp Val Arg Leu Tyr Pro Thr Gly Ser Asn Pro Gln Leu Thr Arg
                290                 295                 300

Glu Val Tyr Thr Asp Pro Ile Val Phe Asn Pro Pro Ala Asn Val Gly
305                 310                 315                 320

Leu Cys Arg Arg Trp Gly Thr Asn Pro Tyr Asn Thr Phe Ser Glu Leu
                325                 330                 335

Glu Asn Ala Phe Ile Arg Pro Pro His Leu Phe Asp Arg Leu Asn Ser
                340                 345                 350

Leu Thr Ile Ser Ser Asn Arg Phe Pro Val Ser Ser Asn Phe Met Asp
                355                 360                 365

Tyr Trp Ser Gly His Thr Leu Arg Arg Ser Tyr Leu Asn Asp Ser Ala
                370                 375                 380

Val Gln Glu Asp Ser Tyr Gly Leu Ile Thr Thr Arg Ala Thr Ile
385                 390                 395                 400

Asn Pro Gly Val Asp Gly Thr Asn Arg Ile Glu Ser Thr Ala Val Asp
                405                 410                 415

Phe Arg Ser Ala Leu Ile Gly Ile Tyr Gly Val Asn Arg Ala Ser Phe
                420                 425                 430

Val Pro Gly Gly Leu Phe Asn Gly Thr Thr Ser Pro Ala Asn Gly Gly
                435                 440                 445

Cys Arg Asp Leu Tyr Asp Thr Asn Asp Glu Leu Pro Pro Asp Glu Ser
450                 455                 460
```

```
Thr Gly Ser Ser Thr His Arg Leu Ser His Val Thr Phe Phe Ser Phe
465                 470                 475                 480

Gln Thr Asn Gln Ala Gly Ser Ile Ala Asn Ala Gly Ser Val Pro Thr
                485                 490                 495

Tyr Val Trp Thr Arg Arg Asp Val Asp Leu Asn Asn Thr Ile Thr Pro
            500                 505                 510

Asn Arg Ile Thr Gln Leu Pro Leu Val Lys Ala Ser Ala Pro Val Ser
        515                 520                 525

Gly Thr Thr Val Leu Lys Gly Pro Gly Phe Thr Gly Gly Gly Ile Leu
    530                 535                 540

Arg Arg Thr Thr Asn Gly Thr Phe Gly Thr Leu Arg Val Thr Val Asn
545                 550                 555                 560

Ser Pro Leu Thr Gln Arg Tyr Arg Val Arg Val Arg Phe Ala Ser Ser
                565                 570                 575

Gly Asn Phe Ser Ile Arg Ile Leu Arg Gly Asn Thr Ser Ile Ala Tyr
            580                 585                 590

Gln Arg Phe Gly Ser Thr Met Asn Arg Gly Gln Glu Leu Thr Tyr Glu
        595                 600                 605

Ser Phe Val Thr Ser Glu Phe Thr Thr Asn Gln Ser Asp Leu Pro Phe
    610                 615                 620

Thr Phe Thr Gln Ala Gln Glu Asn Leu Thr Ile Leu Ala Glu Gly Val
625                 630                 635                 640

Ser Thr Gly Ser Glu Tyr Phe Ile Asp Arg Ile Glu Ile Ile Pro Val
                645                 650                 655

Asn Pro Ala Arg Glu Ala Glu Asp Leu Glu Ala Ala Lys Lys Ala
            660                 665                 670

Val Ala Asn Leu Phe Thr Arg Thr Arg Asp Gly Leu Gln Val Asn Val
        675                 680                 685

Thr Asp Tyr Gln Val Asp Gln Ala Ala Asn Leu Val Ser Cys Leu Ser
    690                 695                 700

Asp Glu Gln Tyr Gly His Asp Lys Lys Met Leu Leu Glu Ala Val Arg
705                 710                 715                 720

Ala Ala Lys Arg Leu Ser Arg Glu Arg Asn Leu Leu Gln Asp Pro Asp
                725                 730                 735

Phe Asn Thr Ile Asn Ser Thr Glu Glu Asn Gly Trp Lys Ala Ser Asn
            740                 745                 750

Gly Val Thr Ile Ser Glu Gly Gly Pro Phe Phe Lys Gly Arg Ala Leu
        755                 760                 765

Gln Leu Ala Ser Ala Arg Glu Asn Tyr Pro Thr Tyr Ile Tyr Gln Lys
    770                 775                 780

Val Asp Ala Ser Val Leu Lys Pro Tyr Thr Arg Tyr Arg Leu Asp Gly
785                 790                 795                 800

Phe Val Lys Ser Ser Gln Asp Leu Glu Ile Asp Leu Ile His His His
                805                 810                 815

Lys Val His Leu Val Lys Asn Val Pro Asp Asn Leu Val Ser Asp Thr
            820                 825                 830

Tyr Ser Asp Gly Ser Cys Ser Gly Ile Asn Arg Cys Asp Glu Gln His
        835                 840                 845

Gln Val Asp Met Gln Leu Asp Ala Glu His His Pro Met Asp Cys Cys
    850                 855                 860

Glu Ala Ala Gln Thr His Glu Phe Ser Ser Tyr Ile Asn Thr Gly Asp
865                 870                 875                 880
```

-continued

```
Leu Asn Ala Ser Val Asp Gln Gly Ile Trp Val Val Leu Lys Val Arg
                885                 890                 895

Thr Thr Asp Gly Tyr Ala Thr Leu Gly Asn Leu Glu Leu Val Glu Val
            900                 905                 910

Gly Pro Leu Ser Gly Glu Ser Leu Glu Arg Glu Gln Arg Asp Asn Ala
        915                 920                 925

Lys Trp Asn Ala Glu Leu Gly Arg Lys Arg Ala Glu Ile Asp Arg Val
    930                 935                 940

Tyr Leu Ala Ala Lys Gln Ala Ile Asn His Leu Phe Val Asp Tyr Gln
945                 950                 955                 960

Asp Gln Gln Leu Asn Pro Glu Ile Gly Leu Ala Glu Ile Asn Glu Ala
                965                 970                 975

Ser Asn Leu Val Glu Ser Ile Ser Gly Val Tyr Ser Asp Thr Leu Leu
            980                 985                 990

Gln Ile Pro Gly Ile Asn Tyr Glu  Ile Tyr Thr Glu Leu  Ser Asp Arg
        995                 1000                1005

Leu Gln  Gln Ala Ser Tyr Leu  Tyr Thr Ser Arg Asn  Ala Val Gln
    1010                 1015                 1020

Asn Gly  Asp Phe Asn Ser Gly  Leu Asp Ser Trp Asn  Thr Thr Met
    1025                 1030                 1035

Asp Ala  Ser Val Gln Gln Asp  Gly Asn Met His Phe  Leu Val Leu
    1040                 1045                 1050

Ser His  Trp Asp Ala Gln Val  Ser Gln Gln Leu Arg  Val Asn Pro
    1055                 1060                 1065

Asn Cys  Lys Tyr Val Leu Arg  Val Thr Ala Arg Lys  Val Gly Gly
    1070                 1075                 1080

Gly Asp  Gly Tyr Val Thr Ile  Arg Asp Gly Ala His  His Gln Glu
    1085                 1090                 1095

Thr Leu  Thr Phe Asn Ala Cys  Asp Tyr Asp Val Asn  Gly Thr Tyr
    1100                 1105                 1110

Val Asn  Asp Asn Ser Tyr Ile  Thr Glu Glu Val Val  Phe Tyr Pro
    1115                 1120                 1125

Glu Thr  Lys His Met Trp Val  Glu Val Ser Glu Ser  Glu Gly Ser
    1130                 1135                 1140

Phe Tyr  Ile Asp Ser Ile Glu  Phe Ile Glu Thr Gln  Glu
    1145                 1150                 1155

<210> SEQ ID NO 29
<211> LENGTH: 2407
<212> TYPE: DNA
<213> ORGANISM: Bacillus thuringiensis

<400> SEQUENCE: 29
atgaatcaaa ataaacacgg aattattggc gcttccaatt gtggttgtgc atctgatgat      60
gttgcgaaat atcctttagc caacaatcca tattcatctg ctttaaattt aaattcttgt     120
caaaatagta gtattctcaa ctggattaac ataataggcg atgcagcaaa agaagcagta     180
tctattggga caaccatagt ctctcttatc acagcacctt ctcttactgg attaatttca     240
atagtatatg accttatagg taaagtacta ggaggtagta gtggacaatc catatcagat     300
ttgtctatat gtgacttatt atctattatt gatttacggg taagtcagag tgttttaaat     360
gatgggattg cagattttaa tggttctgta ctcttataca ggaactattt agaggctctg     420
gatagctgga ataagaatcc taattctgct tctgctgaag aactccgtac tcgttttaga     480
atcgccgact cagaatttga tagaatttta acccgagggt ctttaacgaa tggtggctcg     540
```

-continued

```
ttagctagac aaaatgccca aatattatta ttaccttctt ttgcgagcgc tgcattttc    600 catttattac tactaaggga tgctactaga tatggcacta attgggggct atacaatgct   660
acacctttta taaattatca atcaaaacta gtagagctta ttgaactata tactgattat   720
tgcgtacatt gggataatcg aggttcaacc gaactaagac aacgagggcc tagtgctaca   780
gcttggttag aatttcatag atatcggaga gagatgacat tgatgggatt agaaatagta   840
gcatcatttt caagtcttga tattactaat tacccaatag aaacagattt tcagttgagt   900
agggtcattt atacagatcc aattggtttt gtacatcgta gtagtcttag gggagaaagt   960
tggtttagct ttgttaatag agctaatttc tcagatttag aaaatgcaat acctaatcct  1020
agaccgtctt ggttttaaa taatatgatt atatctactg gttcacttac attgccggtt  1080
agcccaagta ctgatagagc gagggtatgg tatggaagtc gagatcgaat ttcccctgct  1140
aattcacaat ttattactga actaatctct ggacaacata cgactgctac acaaactatt  1200
ttagggcgaa atatatttag agtagattct caagcttgta atttaaatga taccacatat  1260
ggagtgaata gggcggtatt ttatcatgat gcgagtgaag gttctcaaag atccgtgtac  1320 gagggggtata ttcgaacaac tgggatagat aaccctagag ttcaaaatat taacacttat  1380
ttacctggag aaaattcaga tatcccaact ccagaagact atactcatat attaagcaca  1440
acaataaatt taacaggagg acttagacaa gtagcatcta atcgccgttc atctttagta  1500
atgtatggtt ggacacataa aagtctggcc gtaacaata ccattaatcc agatagaatt  1560
acacagatac cattgacgaa ggttgatacc cgaggcacag gtgtttctta tgtgaatgat  1620
ccaggattta taggaggagc tctacttcaa aggactgacc atggttcgct tggagtattg  1680
agggtccaat ttccacttca cttaagacaa caatatcgta ttagagtccg ttatgcttct  1740
acaacaaata ttcgattgag tgtgaatggc agtttcggta ctatttctca aaatctccct  1800
agtacaatga gattaggaga ggatttaaga tacggatctt ttgctataag agagtttaat  1860
acttctatta gacccactgc aagtccggac caaattcgat tgacaataga accatctttt  1920
attagacaag aggtctatgt agatagaatt gagttcattc cagttaatcc gacgcgagag  1980
gcgaaagagg atctagaagc agcaaaaaaa gcggtggcga gcttgtttac acgcacaagg  2040
gacggattac aagtaaatgt gaaagattat caagtcgatc aagcggcaaa tttagtgtca  2100
tgcttatcag atgaacaata tgggtatgac aaaaagatgt tattggaagc ggtacgtgcg  2160
gcaaaacgac ttagccgaga acgcaactta cttcaggatc cagattttaa tacaatcaat  2220
agtacagaag aaaatggatg gaaagcaagt aacggcgtta ctattagtga gggcgggcca  2280
ttctataaag gccgtgcaat tcagctagca agtgcacgag aaaattaccc aacatacatc  2340
tatcaaaaag tagatgcatc ggagttaaag ccgtatacac gttatagact ggatgggttc  2400
gtgaaga                                                           2407
```

<210> SEQ ID NO 30
<211> LENGTH: 802
<212> TYPE: PRT
<213> ORGANISM: Bacillus thuringiensis

<400> SEQUENCE: 30

```
Met Asn Gln Asn Lys His Gly Ile Ile Gly Ala Ser Asn Cys Gly Cys
 1               5                  10                  15

Ala Ser Asp Asp Val Ala Lys Tyr Pro Leu Ala Asn Asn Pro Tyr Ser
             20                  25                  30
```

-continued

```
Ser Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
        50                  55                  60

Thr Ile Val Ser Leu Ile Thr Ala Pro Ser Leu Thr Gly Leu Ile Ser
65                  70                  75                  80

Ile Val Tyr Asp Leu Ile Gly Lys Val Leu Gly Gly Ser Ser Gly Gln
                    85                  90                  95

Ser Ile Ser Asp Leu Ser Ile Cys Asp Leu Leu Ser Ile Ile Asp Leu
                100                 105                 110

Arg Val Ser Gln Ser Val Leu Asn Asp Gly Ile Ala Asp Phe Asn Gly
                115                 120                 125

Ser Val Leu Leu Tyr Arg Asn Tyr Leu Glu Ala Leu Asp Ser Trp Asn
        130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                    165                 170                 175

Asn Gly Gly Ser Leu Ala Arg Gln Asn Ala Gln Ile Leu Leu Leu Pro
                180                 185                 190

Ser Phe Ala Ser Ala Ala Phe His Leu Leu Leu Leu Arg Asp Ala
        195                 200                 205

Thr Arg Tyr Gly Thr Asn Trp Gly Leu Tyr Asn Ala Thr Pro Phe Ile
            210                 215                 220

Asn Tyr Gln Ser Lys Leu Val Glu Leu Ile Glu Leu Tyr Thr Asp Tyr
225                 230                 235                 240

Cys Val His Trp Asp Asn Arg Gly Ser Thr Glu Leu Arg Gln Arg Gly
                    245                 250                 255

Pro Ser Ala Thr Ala Trp Leu Glu Phe His Arg Tyr Arg Arg Glu Met
                260                 265                 270

Thr Leu Met Gly Leu Glu Ile Val Ala Ser Phe Ser Ser Leu Asp Ile
        275                 280                 285

Thr Asn Tyr Pro Ile Glu Thr Asp Phe Gln Leu Ser Arg Val Ile Tyr
        290                 295                 300

Thr Asp Pro Ile Gly Phe Val His Arg Ser Ser Leu Arg Gly Glu Ser
305                 310                 315                 320

Trp Phe Ser Phe Val Asn Arg Ala Asn Phe Ser Asp Leu Glu Asn Ala
                    325                 330                 335

Ile Pro Asn Pro Arg Pro Ser Trp Phe Leu Asn Asn Met Ile Ile Ser
                340                 345                 350

Thr Gly Ser Leu Thr Leu Pro Val Ser Pro Ser Thr Asp Arg Ala Arg
        355                 360                 365

Val Trp Tyr Gly Ser Arg Asp Arg Ile Ser Pro Ala Asn Ser Gln Phe
        370                 375                 380

Ile Thr Glu Leu Ile Ser Gly His Thr Thr Ala Thr Gln Thr Ile
385                 390                 395                 400

Leu Gly Arg Asn Ile Phe Arg Val Asp Ser Gln Ala Cys Asn Leu Asn
                    405                 410                 415

Asp Thr Thr Tyr Gly Val Asn Arg Ala Val Phe Tyr Asp His Ala Ser
                420                 425                 430

Glu Gly Ser Gln Arg Ser Val Tyr Glu Gly Tyr Ile Arg Thr Thr Gly
        435                 440                 445

Ile Asp Asn Pro Arg Val Gln Asn Ile Asn Thr Tyr Leu Pro Gly Glu
```

```
                    450             455             460
Asn Ser Asp Ile Pro Thr Pro Glu Asp Tyr Thr His Ile Leu Ser Thr
465                 470                 475                 480
Thr Ile Asn Leu Thr Gly Gly Leu Arg Gln Val Ala Ser Asn Arg Arg
                485                 490                 495
Ser Ser Leu Val Met Tyr Gly Trp Thr His Lys Ser Leu Ala Arg Asn
                500                 505                 510
Asn Thr Ile Asn Pro Asp Arg Ile Thr Gln Ile Pro Leu Thr Lys Val
                515                 520                 525
Asp Thr Arg Gly Thr Gly Val Ser Tyr Val Asn Asp Pro Gly Phe Ile
530                 535                 540
Gly Gly Ala Leu Leu Gln Arg Thr Asp His Gly Ser Leu Gly Val Leu
545                 550                 555                 560
Arg Val Gln Phe Pro Leu His Leu Arg Gln Gln Tyr Arg Ile Arg Val
                565                 570                 575
Arg Tyr Ala Ser Thr Thr Asn Ile Arg Leu Ser Val Asn Gly Ser Phe
                580                 585                 590
Gly Thr Ile Ser Gln Asn Leu Pro Ser Thr Met Arg Leu Gly Glu Asp
                595                 600                 605
Leu Arg Tyr Gly Ser Phe Ala Ile Arg Glu Phe Asn Thr Ser Ile Arg
610                 615                 620
Pro Thr Ala Ser Pro Asp Gln Ile Arg Leu Thr Ile Glu Pro Ser Phe
625                 630                 635                 640
Ile Arg Gln Glu Val Tyr Val Asp Arg Ile Glu Phe Ile Pro Val Asn
                645                 650                 655
Pro Thr Arg Glu Ala Lys Glu Asp Leu Glu Ala Ala Lys Lys Ala Val
                660                 665                 670
Ala Ser Leu Phe Thr Arg Thr Arg Asp Gly Leu Gln Val Asn Val Lys
                675                 680                 685
Asp Tyr Gln Val Asp Gln Ala Ala Asn Leu Val Ser Cys Leu Ser Asp
                690                 695                 700
Glu Gln Tyr Gly Tyr Asp Lys Lys Met Leu Leu Glu Ala Val Arg Ala
705                 710                 715                 720
Ala Lys Arg Leu Ser Arg Glu Arg Asn Leu Leu Gln Asp Pro Asp Phe
                725                 730                 735
Asn Thr Ile Asn Ser Thr Glu Glu Asn Gly Trp Lys Ala Ser Asn Gly
                740                 745                 750
Val Thr Ile Ser Glu Gly Gly Pro Phe Tyr Lys Gly Arg Ala Ile Gln
                755                 760                 765
Leu Ala Ser Ala Arg Glu Asn Tyr Pro Thr Tyr Ile Tyr Gln Lys Val
770                 775                 780
Asp Ala Ser Glu Leu Lys Pro Tyr Thr Arg Tyr Arg Leu Asp Gly Phe
785                 790                 795                 800
Val Lys

<210> SEQ ID NO 31
<211> LENGTH: 192
<212> TYPE: DNA
<213> ORGANISM: Bacillus thuringiensis

<400> SEQUENCE: 31
catttacgca acctcgtatg gatttcattt ccaagaacta tgggaacaga tgacccatta    60
acttctcgtt cgtttgctct tacaactctt ttcacaccaa taaccttaac acgagcacaa   120
```

```
gaagaattta atctaacaat accacggggt gtttatatag acagaattga attcgtccca      180
gttatgccac at                                                         192
```

<210> SEQ ID NO 32
<211> LENGTH: 64
<212> TYPE: PRT
<213> ORGANISM: Bacillus thuringiensis

<400> SEQUENCE: 32

```
His Leu Arg Asn Leu Val Trp Ile Ser Phe Pro Arg Thr Met Gly Thr
1               5                   10                  15

Asp Asp Pro Leu Thr Ser Arg Ser Phe Ala Leu Thr Thr Leu Phe Thr
            20                  25                  30

Pro Ile Thr Leu Thr Arg Ala Gln Glu Glu Phe Asn Leu Thr Ile Pro
        35                  40                  45

Arg Gly Val Tyr Ile Asp Arg Ile Glu Phe Val Pro Val Met Pro His
    50                  55                  60
```

<210> SEQ ID NO 33
<211> LENGTH: 246
<212> TYPE: DNA
<213> ORGANISM: Bacillus thuringiensis

<400> SEQUENCE: 33

```
gcttctacta caaatttaca attccataca tcaattgacg gaagacctat taatcagggg      60 aattttcag caactatgag tagtgggggt aatttacagt ccggaagctt taggactgca      120
ggctttacta ctccgtttaa cttttcaaat ggatcaagta tatttacgtt aagtgctcat     180
gtcttcaatt caggcaatga agtttatata gatcgaattg aatttgttcc ggcagaagta     240
acattt                                                                246
```

<210> SEQ ID NO 34
<211> LENGTH: 82
<212> TYPE: PRT
<213> ORGANISM: Bacillus thuringiensis

<400> SEQUENCE: 34

```
Ala Ser Thr Thr Asn Leu Gln Phe His Thr Ser Ile Asp Gly Arg Pro
1               5                   10                  15

Ile Asn Gln Gly Asn Phe Ser Ala Thr Met Ser Ser Gly Gly Asn Leu
            20                  25                  30

Gln Ser Gly Ser Phe Arg Thr Ala Gly Phe Thr Thr Pro Phe Asn Phe
        35                  40                  45

Ser Asn Gly Ser Ser Ile Phe Thr Leu Ser Ala His Val Phe Asn Ser
    50                  55                  60

Gly Asn Glu Val Tyr Ile Asp Arg Ile Glu Phe Val Pro Ala Glu Val
65                  70                  75                  80

Thr Phe
```

<210> SEQ ID NO 35
<211> LENGTH: 177
<212> TYPE: DNA
<213> ORGANISM: Bacillus thuringiensis

<400> SEQUENCE: 35

```
ctctttccag attatattca gcctcgagtg ttgcagtaac tggaataaat tcaaatctgt      60
ctattatcac tcctgcagtc ccactaaaat ttctaacacc tactatatta cctaatgaag     120
```

```
atgtaaaagc attggcactt caaaatcact tgattgtaga ttatctaatg acgtagc         177
```

<210> SEQ ID NO 36
<211> LENGTH: 57
<212> TYPE: PRT
<213> ORGANISM: Bacillus thuringiensis

<400> SEQUENCE: 36

```
Leu Ser Arg Leu Tyr Ser Ala Ser Ser Val Ala Val Thr Gly Ile Asn
1               5                   10                  15

Ser Asn Leu Ser Ile Ile Thr Pro Ala Val Pro Leu Lys Phe Leu Thr
                20                  25                  30

Pro Thr Ile Leu Pro Asn Glu Asp Val Lys Ala Leu Ala Leu Gln Asn
            35                  40                  45

His Leu Ile Val Asp Tyr Leu Met Thr
        50                  55
```

<210> SEQ ID NO 37
<211> LENGTH: 4173
<212> TYPE: DNA
<213> ORGANISM: Bacillus thuringiensis
<220> FEATURE:
<221> NAME/KEY: CDS
<222> LOCATION: (1)..(3687)

<400> SEQUENCE: 37

```
ttg act tca aat agg aaa aat gag aat gaa att ata aat gct tta tcg         48
Leu Thr Ser Asn Arg Lys Asn Glu Asn Glu Ile Ile Asn Ala Leu Ser
1               5                   10                  15 att cca gct gta tcg aat cat tcc aca caa atg gat cta tca cca gat         96
Ile Pro Ala Val Ser Asn His Ser Thr Gln Met Asp Leu Ser Pro Asp
                20                  25                  30 gct cgt att gag gat tct ttg tgt ata gcc gag ggg aat aat atc aat        144
Ala Arg Ile Glu Asp Ser Leu Cys Ile Ala Glu Gly Asn Asn Ile Asn
            35                  40                  45 cca ctt gtt agc gca tca aca gtc caa acg ggt att aac ata gct ggt        192
Pro Leu Val Ser Ala Ser Thr Val Gln Thr Gly Ile Asn Ile Ala Gly
        50                  55                  60 aga ata cta ggt gta tta ggc gta ccg ttt gct gga caa ata gct agt        240
Arg Ile Leu Gly Val Leu Gly Val Pro Phe Ala Gly Gln Ile Ala Ser
65                  70                  75                  80 ttt tat agt ttt ctt gtt ggt gaa tta tgg ccc cgc ggc aga gat cag        288
Phe Tyr Ser Phe Leu Val Gly Glu Leu Trp Pro Arg Gly Arg Asp Gln
                85                  90                  95 tgg gaa att ttc cta gaa cat gtc gaa caa ctt ata aat caa caa ata        336
Trp Glu Ile Phe Leu Glu His Val Glu Gln Leu Ile Asn Gln Gln Ile
                100                 105                 110 aca gaa aat gct agg aat acg gca ctt gct cga tta caa ggt tta gga        384
Thr Glu Asn Ala Arg Asn Thr Ala Leu Ala Arg Leu Gln Gly Leu Gly
            115                 120                 125 gat tcc ttt aga gcc tat caa cag tca ctt gaa gat tgg cta gaa aac        432
Asp Ser Phe Arg Ala Tyr Gln Gln Ser Leu Glu Asp Trp Leu Glu Asn
        130                 135                 140 cgt gat gat gca aga acg aga agt gtt ctt tat acc caa tat ata gcc        480
Arg Asp Asp Ala Arg Thr Arg Ser Val Leu Tyr Thr Gln Tyr Ile Ala
145                 150                 155                 160 tta gaa ctt gat ttt ctt aat gcg atg ccg ctt ttc gca att aga aac        528
Leu Glu Leu Asp Phe Leu Asn Ala Met Pro Leu Phe Ala Ile Arg Asn
                165                 170                 175 caa gaa gtt cca tta tta atg gta tat gct caa gct gca aat tta cac        576
Gln Glu Val Pro Leu Leu Met Val Tyr Ala Gln Ala Ala Asn Leu His
```

-continued

```
              180                 185                 190
cta tta tta ttg aga gat gcc tct ctt ttt ggt agt gaa ttt ggg ctt    624
Leu Leu Leu Leu Arg Asp Ala Ser Leu Phe Gly Ser Glu Phe Gly Leu
            195                 200                 205 aca tcg cag gaa att caa cgt tat tat gag cgc caa gtg gaa caa acg    672
Thr Ser Gln Glu Ile Gln Arg Tyr Tyr Glu Arg Gln Val Glu Gln Thr
        210                 215                 220 aga gat tat tcc gac tat tgc gta gaa tgg tat aat aca ggt cta aat    720
Arg Asp Tyr Ser Asp Tyr Cys Val Glu Trp Tyr Asn Thr Gly Leu Asn
225                 230                 235                 240 agc ttg aga ggg aca aat gcc gca agt tgg gtg cgt tat aat caa ttc    768
Ser Leu Arg Gly Thr Asn Ala Ala Ser Trp Val Arg Tyr Asn Gln Phe
                245                 250                 255 cgt aga gat cta acg tta ggg gta tta gat cta gtg gca cta ttc cca    816
Arg Arg Asp Leu Thr Leu Gly Val Leu Asp Leu Val Ala Leu Phe Pro
            260                 265                 270 agc tat gac act cgc act tat cca ata aat acg agt gct cag tta aca    864
Ser Tyr Asp Thr Arg Thr Tyr Pro Ile Asn Thr Ser Ala Gln Leu Thr
        275                 280                 285 agg gaa gtt tat aca gac gca att gga gca aca ggg gta aat atg gca    912
Arg Glu Val Tyr Thr Asp Ala Ile Gly Ala Thr Gly Val Asn Met Ala
    290                 295                 300 agt atg aat tgg tat aat aat aat gca cct tcg ttt tcc gct ata gag    960
Ser Met Asn Trp Tyr Asn Asn Asn Ala Pro Ser Phe Ser Ala Ile Glu
305                 310                 315                 320 act gcg gtt atc cga agc ccg cat cta ctt gat ttt cta gaa caa ctt   1008
Thr Ala Val Ile Arg Ser Pro His Leu Leu Asp Phe Leu Glu Gln Leu
                325                 330                 335 aca att ttt agc act tca tca cga tgg agt gct act agg cat atg act   1056
Thr Ile Phe Ser Thr Ser Ser Arg Trp Ser Ala Thr Arg His Met Thr
            340                 345                 350 tac tgg cgg ggg cac aca att caa tct cgg cca ata gga ggc gga tta   1104
Tyr Trp Arg Gly His Thr Ile Gln Ser Arg Pro Ile Gly Gly Gly Leu
        355                 360                 365 aat acc tca acg cat ggg tct acc aat act tct att aat cct gta aga   1152
Asn Thr Ser Thr His Gly Ser Thr Asn Thr Ser Ile Asn Pro Val Arg
    370                 375                 380 tta tca ttc ttc tct cga gac gta tat tgg act gaa tca tat gca gga   1200
Leu Ser Phe Phe Ser Arg Asp Val Tyr Trp Thr Glu Ser Tyr Ala Gly
385                 390                 395                 400 gtg ctt cta tgg gga att tac ctt gaa cct att cat ggt gtc cct act   1248
Val Leu Leu Trp Gly Ile Tyr Leu Glu Pro Ile His Gly Val Pro Thr
                405                 410                 415 gtt aga ttt aat ttt agg aac cct cag aat act ttt gaa aga ggt act   1296
Val Arg Phe Asn Phe Arg Asn Pro Gln Asn Thr Phe Glu Arg Gly Thr
            420                 425                 430 gct aac tat agt caa ccc tat gag tca cct ggg ctt caa tta aaa gat   1344
Ala Asn Tyr Ser Gln Pro Tyr Glu Ser Pro Gly Leu Gln Leu Lys Asp
        435                 440                 445 tca gaa act gaa tta cca cca gaa aca aca gaa cga cca aat tat gaa   1392
Ser Glu Thr Glu Leu Pro Pro Glu Thr Thr Glu Arg Pro Asn Tyr Glu
    450                 455                 460 tca tat agt cat agg tta tct cac ata ggg ctc att tca caa tct agg   1440
Ser Tyr Ser His Arg Leu Ser His Ile Gly Leu Ile Ser Gln Ser Arg
465                 470                 475                 480 gtg cat gta cca gta tat tct tgg acg cac cgt agt gca gat cgt aca   1488
Val His Val Pro Val Tyr Ser Trp Thr His Arg Ser Ala Asp Arg Thr
                485                 490                 495 aat acc att agt tca gat agc ata aca caa ata cca ttg gta aaa tca   1536
```

```
                Asn Thr Ile Ser Ser Asp Ser Ile Thr Gln Ile Pro Leu Val Lys Ser
                                500                 505                 510 ttc aac ctt aat tca ggt acc tct gta gtc agt ggc cca gga ttt aca                    1584
Phe Asn Leu Asn Ser Gly Thr Ser Val Val Ser Gly Pro Gly Phe Thr
                515                 520                 525 gga ggg gat ata atc cga act aac gtt aat ggt agt gta cta agt atg                    1632
Gly Gly Asp Ile Ile Arg Thr Asn Val Asn Gly Ser Val Leu Ser Met
            530                 535                 540 ggt ctt aat ttt aat aat aca tca tta cag cgg tat cgc gtg aga gtt                    1680
Gly Leu Asn Phe Asn Asn Thr Ser Leu Gln Arg Tyr Arg Val Arg Val
545                 550                 555                 560 cgt tat gct gct tct caa aca atg gtc ctg agg gta act gtc gga ggg                    1728
Arg Tyr Ala Ala Ser Gln Thr Met Val Leu Arg Val Thr Val Gly Gly
                565                 570                 575 agt act act ttt gat caa gga ttc cct agt act atg agt gca aat gag                    1776
Ser Thr Thr Phe Asp Gln Gly Phe Pro Ser Thr Met Ser Ala Asn Glu
                580                 585                 590 tct ttg aca tct caa tca ttt aga ttt gca gaa ttt cct gta ggt att                    1824
Ser Leu Thr Ser Gln Ser Phe Arg Phe Ala Glu Phe Pro Val Gly Ile
                595                 600                 605 agt gca tct ggc agt caa act gct gga ata agt ata agt aat aat gca                    1872
Ser Ala Ser Gly Ser Gln Thr Ala Gly Ile Ser Ile Ser Asn Asn Ala
    610                 615                 620 ggt aga caa acg ttt cac ttt gat aaa att gaa ttc att cca att act                    1920
Gly Arg Gln Thr Phe His Phe Asp Lys Ile Glu Phe Ile Pro Ile Thr
625                 630                 635                 640 gca acc ttc gaa gca gaa tac gat tta gaa agg gcg caa gag gcg gtg                    1968
Ala Thr Phe Glu Ala Glu Tyr Asp Leu Glu Arg Ala Gln Glu Ala Val
                645                 650                 655 aat gct ctg ttt act aat acg aat cca aga aga ttg aaa aca gat gtg                    2016
Asn Ala Leu Phe Thr Asn Thr Asn Pro Arg Arg Leu Lys Thr Asp Val
                660                 665                 670 aca gat tat cat att gat caa gta tcc aat tta gtg gcg tgt tta tcg                    2064
Thr Asp Tyr His Ile Asp Gln Val Ser Asn Leu Val Ala Cys Leu Ser
                675                 680                 685 gat gaa ttc tgc tta gat gaa aag aga gaa tta ctt gag aaa gtg aaa                    2112
Asp Glu Phe Cys Leu Asp Glu Lys Arg Glu Leu Leu Glu Lys Val Lys
    690                 695                 700 tat gcg aaa cga ctc agt gat gaa aga aac tta ctc caa gat cca aac                    2160
Tyr Ala Lys Arg Leu Ser Asp Glu Arg Asn Leu Leu Gln Asp Pro Asn
705                 710                 715                 720 ttc aca tcc atc aat aag caa cca gac ttc ata tct act aat gag caa                    2208
Phe Thr Ser Ile Asn Lys Gln Pro Asp Phe Ile Ser Thr Asn Glu Gln
                725                 730                 735 tcg aat ttc aca tct atc cat gaa caa tct gaa cat gga tgg tgg gga                    2256
Ser Asn Phe Thr Ser Ile His Glu Gln Ser Glu His Gly Trp Trp Gly
                740                 745                 750 agt gag aac att aca atc cag gaa gga aat gac gta ttt aaa gag aat                    2304
Ser Glu Asn Ile Thr Ile Gln Glu Gly Asn Asp Val Phe Lys Glu Asn
                755                 760                 765 tac gtc aca cta ccg ggg act ttt aat gag tgt tat ccg acg tat tta                    2352
Tyr Val Thr Leu Pro Gly Thr Phe Asn Glu Cys Tyr Pro Thr Tyr Leu
    770                 775                 780 tat caa aaa ata gga gag tcg gaa tta aaa gct tat act cgc tac caa                    2400
Tyr Gln Lys Ile Gly Glu Ser Glu Leu Lys Ala Tyr Thr Arg Tyr Gln
785                 790                 795                 800 tta aga ggg tat att gaa gat agt caa gat tta gag ata tat ttg att                    2448
Leu Arg Gly Tyr Ile Glu Asp Ser Gln Asp Leu Glu Ile Tyr Leu Ile
                805                 810                 815
```

-continued

| | | |
|---|---|---|
| cgt tat aat gcg aaa cat gaa aca ttg gat gtt cca ggt acc gag tcc<br>Arg Tyr Asn Ala Lys His Glu Thr Leu Asp Val Pro Gly Thr Glu Ser<br>        820                    825                  830 | 2496 |
| gta tgg ccg ctt tca gtt gaa agc cca atc gga agg tgc gga gaa ccg<br>Val Trp Pro Leu Ser Val Glu Ser Pro Ile Gly Arg Cys Gly Glu Pro<br>        835                    840                  845 | 2544 |
| aat cga tgc gca cca cat ttt gaa tgg aat cct gat cta gat tgt tcc<br>Asn Arg Cys Ala Pro His Phe Glu Trp Asn Pro Asp Leu Asp Cys Ser<br>850                    855                  860 | 2592 |
| tgc aga gat gga gaa aaa tgt gcg cat cat tcc cat cat ttc tct ttg<br>Cys Arg Asp Gly Glu Lys Cys Ala His His Ser His His Phe Ser Leu<br>865                    870                  875                  880 | 2640 |
| gat att gat att gga tgc aca gac ttg cat gag aat cta ggc gtg tgg<br>Asp Ile Asp Ile Gly Cys Thr Asp Leu His Glu Asn Leu Gly Val Trp<br>                    885                  890                  895 | 2688 |
| gtg gta ttc aag att aag acg cag gaa ggt cat gca aga cta ggg aat<br>Val Val Phe Lys Ile Lys Thr Gln Glu Gly His Ala Arg Leu Gly Asn<br>        900                    905                  910 | 2736 |
| ctg gaa ttt att gaa gag aaa cca tta tta gga gaa gca ctg tct cgt<br>Leu Glu Phe Ile Glu Glu Lys Pro Leu Leu Gly Glu Ala Leu Ser Arg<br>        915                    920                  925 | 2784 |
| gtg aag aga gca gag aaa aaa tgg aga gac aaa cgt gaa aaa cta caa<br>Val Lys Arg Ala Glu Lys Lys Trp Arg Asp Lys Arg Glu Lys Leu Gln<br>930                    935                  940 | 2832 |
| ttg gaa aca aaa cga gta tat aca gag gca aaa gaa gct gtg gat gct<br>Leu Glu Thr Lys Arg Val Tyr Thr Glu Ala Lys Glu Ala Val Asp Ala<br>945                    950                  955                  960 | 2880 |
| tta ttt gta gat tct caa tat aat aga tta caa gcg gat aca aac att<br>Leu Phe Val Asp Ser Gln Tyr Asn Arg Leu Gln Ala Asp Thr Asn Ile<br>                    965                  970                  975 | 2928 |
| ggc atg att cat gcg gca gat aaa ctt gtt cat cga att cga gag gct<br>Gly Met Ile His Ala Ala Asp Lys Leu Val His Arg Ile Arg Glu Ala<br>        980                    985                  990 | 2976 |
| tat ctg tca gaa tta tct gtt atc ccg ggt gta aat gcg gaa att ttt<br>Tyr Leu Ser Glu Leu Ser Val Ile Pro Gly Val Asn Ala Glu Ile Phe<br>        995                    1000                1005 | 3024 |
| gaa gaa tta gaa ggt cgc att atc act gca atc tcc cta tac gat<br>Glu Glu Leu Glu Gly Arg Ile Ile Thr Ala Ile Ser Leu Tyr Asp<br>        1010                  1015                1020 | 3069 |
| gcg aga aat gtc gtt aaa aat ggt gat ttt aat aat gga tta gca<br>Ala Arg Asn Val Val Lys Asn Gly Asp Phe Asn Asn Gly Leu Ala<br>1025                    1030                1035 | 3114 |
| tgc tgg aat gta aaa ggg cat gta gat gta caa cag agc cat cac<br>Cys Trp Asn Val Lys Gly His Val Asp Val Gln Gln Ser His His<br>        1040                  1045                1050 | 3159 |
| cgt tct gtc ctt gtt atc cca gaa tgg gaa gca gaa gtg tca caa<br>Arg Ser Val Leu Val Ile Pro Glu Trp Glu Ala Glu Val Ser Gln<br>1055                    1060                1065 | 3204 |
| gca gtt cgc gtc tgt ccg ggg cgt ggc tat atc ctc cgt gtc aca<br>Ala Val Arg Val Cys Pro Gly Arg Gly Tyr Ile Leu Arg Val Thr<br>        1070                  1075                1080 | 3249 |
| gcg tac aaa gag gga tat gga gag ggt tgt gta acg atc cat gaa<br>Ala Tyr Lys Glu Gly Tyr Gly Glu Gly Cys Val Thr Ile His Glu<br>1085                    1090                1095 | 3294 |
| atc gag aac aat aca gac gaa cta aaa ttt aaa aac tgt gaa gaa<br>Ile Glu Asn Asn Thr Asp Glu Leu Lys Phe Lys Asn Cys Glu Glu<br>        1100                  1105                1110 | 3339 |
| gag gaa gtg tat cca acg gat aca gga acg tgt aat gat tat act<br>Glu Glu Val Tyr Pro Thr Asp Thr Gly Thr Cys Asn Asp Tyr Thr<br>1115                    1120                1125 | 3384 |

```
gca cac caa ggt aca gca tgt aat tcc cgt aat gct gga tat        3429
Ala His Gln Gly Thr Ala Ala Cys Asn Ser Arg Asn Ala Gly Tyr
    1130            1135                1140 gag gat gca tat gaa gtt gat act aca gca tct gtt aat tac aaa    3474
Glu Asp Ala Tyr Glu Val Asp Thr Thr Ala Ser Val Asn Tyr Lys
1145            1150                1155 ccg act tat gaa gaa gaa acg tat aca gat gta cga aga gat aat    3519
Pro Thr Tyr Glu Glu Glu Thr Tyr Thr Asp Val Arg Arg Asp Asn
    1160            1165                1170 cat tgt gaa tat gac aga ggg tat gtg aat tat cca cca cta cca    3564
His Cys Glu Tyr Asp Arg Gly Tyr Val Asn Tyr Pro Pro Leu Pro
    1175            1180                1185 gct ggt tat gtg aca aag gaa tta gaa tat ttc cca gaa acc gat    3609
Ala Gly Tyr Val Thr Lys Glu Leu Glu Tyr Phe Pro Glu Thr Asp
    1190            1195                1200 aag gta tgg att gag att gga gaa acg gaa gga aca ttc atc gtg    3654
Lys Val Trp Ile Glu Ile Gly Glu Thr Glu Gly Thr Phe Ile Val
    1205            1210                1215 gac agc ata gaa tta ctc ctt atg gaa gaa tag gaccgtccga         3697
Asp Ser Ile Glu Leu Leu Leu Met Glu Glu
    1220            1225 gtatagcagt ttaataaatc ttaatcaaaa tagtagtcta acttccgtta caatttaata    3757
agtaaattac agttgtaaaa agaaaacgga catcactcct aagagagcga tgtccgtttt    3817
ctatatggtg tgtgctaacg ataagtgtac acggaatttc attatccaaa ttaatatttta   3877 tttgagaaaa ggatcatgtt atatagagat atttccttat aatatttgtt ccacgttcat    3937 aattttgaa tgatacatta caacaaaaac tgtcacaaat ttatatgttc tacataaaat     3997
atatggttaa gaacctaaga agttatgaat caagtaatag gataaaactg aaaaaggaag    4057
tgtaggtaca atgaataaaa aaataagaaa tgaagatgag cattcatcga tagaattatc    4117
atatagtact tcaaaaaatc aaaagcataa ggtaccattt tgttgtacaa tttcag        4173
```

<210> SEQ ID NO 38
<211> LENGTH: 1228
<212> TYPE: PRT
<213> ORGANISM: Bacillus thuringiensis

<400> SEQUENCE: 38

```
Le

```
Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
            165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Val Glu Gln Thr
        210                 215                 220

Arg Asp Tyr Ser Asp Tyr Cys Val Glu Trp Tyr Asn Thr Gly Leu Asn
225                 230                 235                 240

Ser Leu Arg Gly Thr Asn Ala Ala Ser Trp Val Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Asn Thr Ser Ala Gln Leu Thr
        275                 280                 285

Arg Glu Val Tyr Thr Asp Ala Ile Gly Ala Thr Gly Val Asn Met Ala
            290                 295                 300

Ser Met Asn Trp Tyr Asn Asn Ala Pro Ser Phe Ser Ala Ile Glu
305                 310                 315                 320

Thr Ala Val Ile Arg Ser Pro His Leu Leu Asp Phe Leu Glu Gln Leu
                325                 330                 335

Thr Ile Phe Ser Thr Ser Arg Trp Ser Ala Thr Arg His Met Thr
            340                 345                 350

Tyr Trp Arg Gly His Thr Ile Gln Ser Arg Pro Ile Gly Gly Leu
        355                 360                 365

Asn Thr Ser Thr His Gly Ser Thr Asn Thr Ser Ile Asn Pro Val Arg
            370                 375                 380

Leu Ser Phe Phe Ser Arg Asp Val Tyr Trp Thr Glu Ser Tyr Ala Gly
385                 390                 395                 400

Val Leu Leu Trp Gly Ile Tyr Leu Glu Pro Ile His Gly Val Pro Thr
                405                 410                 415

Val Arg Phe Asn Phe Arg Asn Pro Gln Asn Thr Phe Glu Arg Gly Thr
            420                 425                 430

Ala Asn Tyr Ser Gln Pro Tyr Glu Ser Pro Gly Leu Gln Leu Lys Asp
            435                 440                 445

Ser Glu Thr Glu Leu Pro Pro Glu Thr Thr Glu Arg Pro Asn Tyr Glu
    450                 455                 460

Ser Tyr Ser His Arg Leu Ser His Ile Gly Leu Ile Ser Gln Ser Arg
465                 470                 475                 480

Val His Val Pro Val Tyr Ser Trp Thr His Arg Ser Ala Asp Arg Thr
            485                 490                 495

Asn Thr Ile Ser Ser Asp Ser Ile Thr Gln Ile Pro Leu Val Lys Ser
            500                 505                 510

Phe Asn Leu Asn Ser Gly Thr Ser Val Val Ser Gly Pro Gly Phe Thr
    515                 520                 525

Gly Gly Asp Ile Ile Arg Thr Asn Val Asn Gly Ser Val Leu Ser Met
        530                 535                 540

Gly Leu Asn Phe Asn Asn Thr Ser Leu Gln Arg Tyr Arg Val Arg Val
545                 550                 555                 560
```

```
-continued

Arg Tyr Ala Ala Ser Gln Thr Met Val Leu Arg Val Thr Val Gly Gly
                565                 570                 575

Ser Thr Thr Phe Asp Gln Gly Phe Pro Ser Thr Met Ser Ala Asn Glu
            580                 585                 590

Ser Leu Thr Ser Gln Ser Phe Arg Phe Ala Glu Phe Pro Val Gly Ile
        595                 600                 605

Ser Ala Ser Gly Ser Gln Thr Ala Gly Ile Ser Ile Ser Asn Asn Ala
    610                 615                 620

Gly Arg Gln Thr Phe His Phe Asp Lys Ile Glu Phe Ile Pro Ile Thr
625                 630                 635                 640

Ala Thr Phe Glu Ala Glu Tyr Asp Leu Glu Arg Ala Gln Glu Ala Val
                645                 650                 655

Asn Ala Leu Phe Thr Asn Thr Asn Pro Arg Arg Leu Lys Thr Asp Val
            660                 665                 670

Thr Asp Tyr His Ile Asp Gln Val Ser Asn Leu Val Ala Cys Leu Ser
        675                 680                 685

Asp Glu Phe Cys Leu Asp Glu Lys Arg Glu Leu Leu Glu Lys Val Lys
    690                 695                 700

Tyr Ala Lys Arg Leu Ser Asp Glu Arg Asn Leu Leu Gln Asp Pro Asn
705                 710                 715                 720

Phe Thr Ser Ile Asn Lys Gln Pro Asp Phe Ile Ser Thr Asn Glu Gln
                725                 730                 735

Ser Asn Phe Thr Ser Ile His Glu Gln Ser Glu His Gly Trp Trp Gly
            740                 745                 750

Ser Glu Asn Ile Thr Ile Gln Glu Gly Asn Asp Val Phe Lys Glu Asn
        755                 760                 765

Tyr Val Thr Leu Pro Gly Thr Phe Asn Glu Cys Tyr Pro Thr Tyr Leu
    770                 775                 780

Tyr Gln Lys Ile Gly Glu Ser Glu Leu Lys Ala Tyr Thr Arg Tyr Gln
785                 790                 795                 800

Leu Arg Gly Tyr Ile Glu Asp Ser Gln Asp Leu Glu Ile Tyr Leu Ile
                805                 810                 815

Arg Tyr Asn Ala Lys His Glu Thr Leu Asp Val Pro Gly Thr Glu Ser
            820                 825                 830

Val Trp Pro Leu Ser Val Glu Ser Pro Ile Gly Arg Cys Gly Glu Pro
        835                 840                 845

Asn Arg Cys Ala Pro His Phe Glu Trp Asn Pro Asp Leu Asp Cys Ser
    850                 855                 860

Cys Arg Asp Gly Glu Lys Cys Ala His His Ser His His Phe Ser Leu
865                 870                 875                 880

Asp Ile Asp Ile Gly Cys Thr Asp Leu His Glu Asn Leu Gly Val Trp
                885                 890                 895

Val Val Phe Lys Ile Lys Thr Gln Glu Gly His Ala Arg Leu Gly Asn
            900                 905                 910

Leu Glu Phe Ile Glu Glu Lys Pro Leu Leu Gly Glu Ala Leu Ser Arg
        915                 920                 925

Val Lys Arg Ala Glu Lys Lys Trp Arg Asp Lys Arg Glu Lys Leu Gln
    930                 935                 940

Leu Glu Thr Lys Arg Val Tyr Thr Glu Ala Lys Glu Ala Val Asp Ala
945                 950                 955                 960

Leu Phe Val Asp Ser Gln Tyr Asn Arg Leu Gln Ala Asp Thr Asn Ile
                965                 970                 975

Gly Met Ile His Ala Ala Asp Lys Leu Val His Arg Ile Arg Glu Ala
```

```
                980             985             990
Tyr Leu Ser Glu Leu Ser Val Ile Pro Gly Val Asn Ala Glu Ile Phe
            995             1000            1005
Glu Glu Leu Glu Gly Arg Ile Ile Thr Ala Ile Ser Leu Tyr Asp
    1010            1015            1020
Ala Arg Asn Val Val Lys Asn Gly Asp Phe Asn Asn Gly Leu Ala
    1025            1030            1035
Cys Trp Asn Val Lys Gly His Val Asp Val Gln Gln Ser His His
    1040            1045            1050
Arg Ser Val Leu Val Ile Pro Glu Trp Glu Ala Glu Val Ser Gln
    1055            1060            1065
Ala Val Arg Val Cys Pro Gly Arg Gly Tyr Ile Leu Arg Val Thr
    1070            1075            1080
Ala Tyr Lys Glu Gly Tyr Gly Glu Gly Cys Val Thr Ile His Glu
    1085            1090            1095
Ile Glu Asn Asn Thr Asp Glu Leu Lys Phe Lys Asn Cys Glu Glu
    1100            1105            1110
Glu Glu Val Tyr Pro Thr Asp Thr Gly Thr Cys Asn Asp Tyr Thr
    1115            1120            1125
Ala His Gln Gly Thr Ala Ala Cys Asn Ser Arg Asn Ala Gly Tyr
    1130            1135            1140
Glu Asp Ala Tyr Glu Val Asp Thr Thr Ala Ser Val Asn Tyr Lys
    1145            1150            1155
Pro Thr Tyr Glu Glu Glu Thr Tyr Thr Asp Val Arg Arg Asp Asn
    1160            1165            1170
His Cys Glu Tyr Asp Arg Gly Tyr Val Asn Tyr Pro Pro Leu Pro
    1175            1180            1185
Ala Gly Tyr Val Thr Lys Glu Leu Glu Tyr Phe Pro Glu Thr Asp
    1190            1195            1200
Lys Val Trp Ile Glu Ile Gly Glu Thr Glu Gly Thr Phe Ile Val
    1205            1210            1215
Asp Ser Ile Glu Leu Leu Leu Met Glu Glu
    1220            1225

<210> SEQ ID NO 39
<211> LENGTH: 3504
<212> TYPE: DNA
<213> ORGANISM: Bacillus thuringiensis
<220> FEATURE:
<221> NAME/KEY: CDS
<222> LOCATION: (1)..(3504)

<400> SEQUENCE: 39 atg gag aga aat aat cag gat caa tgc att cct tat aat tgt tta aat      48
Met Glu Arg Asn Asn Gln Asp Gln Cys Ile Pro Tyr Asn Cys Leu Asn
1               5                   10                  15 aat cct gag att gag ata tta gat gtt gaa aat ttc aat ctc gaa ctt      96
Asn Pro Glu Ile Glu Ile Leu Asp Val Glu Asn Phe Asn Leu Glu Leu
            20                  25                  30 gta tcg caa gtc agt gtg gga ctt aca cgt ttt ctt cta gag tca gct     144
Val Ser Gln Val Ser Val Gly Leu Thr Arg Phe Leu Leu Glu Ser Ala
        35                  40                  45 gtc cca gga gcg ggt ttt gca ctt ggc cta ttc gat atc att tgg gga     192
Val Pro Gly Ala Gly Phe Ala Leu Gly Leu Phe Asp Ile Ile Trp Gly
    50                  55                  60 gct cta ggc gtc gat caa tgg agc tta ttc ctt gcg caa att gag caa     240
Ala Leu Gly Val Asp Gln Trp Ser Leu Phe Leu Ala Gln Ile Glu Gln
```

```
                                                            -continued 65                  70                  75                  80 tta att aat gaa agg ata aca aca gtt gaa agg aat aga gca att caa    288
Leu Ile Asn Glu Arg Ile Thr Thr Val Glu Arg Asn Arg Ala Ile Gln
             85                  90                  95 aca tta agt gga cta tcg agt agt tat gaa gta tat att gag gca tta    336
Thr Leu Ser Gly Leu Ser Ser Ser Tyr Glu Val Tyr Ile Glu Ala Leu
            100                 105                 110 aga gaa tgg gag aat aat cca gat aat cca gct tca caa gag aga gtg    384
Arg Glu Trp Glu Asn Asn Pro Asp Asn Pro Ala Ser Gln Glu Arg Val
        115                 120                 125 cgt aca cga ttt cgt aca acg gac gac gct cta ata aca gct ata cct    432
Arg Thr Arg Phe Arg Thr Thr Asp Asp Ala Leu Ile Thr Ala Ile Pro
    130                 135                 140 aat tta gcg att cca gat ttt gag ata gct act tta tca gtg tat gtt    480
Asn Leu Ala Ile Pro Asp Phe Glu Ile Ala Thr Leu Ser Val Tyr Val
145                 150                 155                 160 caa gca gcc aat cta cat cta tct tta tta aga gat gct gtt tac ttt    528
Gln Ala Ala Asn Leu His Leu Ser Leu Leu Arg Asp Ala Val Tyr Phe
                165                 170                 175 gga gaa aga tgg gga ctc aca caa gta aat att gaa gat ctt tat acg    576
Gly Glu Arg Trp Gly Leu Thr Gln Val Asn Ile Glu Asp Leu Tyr Thr
            180                 185                 190 aga tta aca aga aat att cat att tat tca gat cat tgt gca agg tgg    624
Arg Leu Thr Arg Asn Ile His Ile Tyr Ser Asp His Cys Ala Arg Trp
        195                 200                 205 tat aat caa ggt tta aat aat att gga gca aca aat acg aga tat ttg    672
Tyr Asn Gln Gly Leu Asn Asn Ile Gly Ala Thr Asn Thr Arg Tyr Leu
    210                 215                 220 gaa ttc caa aga gaa tta aca ctc tct gtc tta gat att gtg gcc ctt    720
Glu Phe Gln Arg Glu Leu Thr Leu Ser Val Leu Asp Ile Val Ala Leu
225                 230                 235                 240 ttc ccg aat tac gac atc cga aca tat tca att ccg aca caa agt caa    768
Phe Pro Asn Tyr Asp Ile Arg Thr Tyr Ser Ile Pro Thr Gln Ser Gln
                245                 250                 255 tta aca agg gag att tat acc gat ata att gct gca ccc aat gca tca    816
Leu Thr Arg Glu Ile Tyr Thr Asp Ile Ile Ala Ala Pro Asn Ala Ser
            260                 265                 270 aat tta ata gtg gga acg caa ggc cta gtg aga gca cct cac tta atg    864
Asn Leu Ile Val Gly Thr Gln Gly Leu Val Arg Ala Pro His Leu Met
        275                 280                 285 gac ttt tta gtc cgt ttg aat att tat act ggc ttg gct aga aat att    912
Asp Phe Leu Val Arg Leu Asn Ile Tyr Thr Gly Leu Ala Arg Asn Ile
    290                 295                 300 cgt cat tgg gca gga cat gaa gta ata tct aga aga aca ggt gga gtg    960
Arg His Trp Ala Gly His Glu Val Ile Ser Arg Arg Thr Gly Gly Val
305                 310                 315                 320 gat tta aat act ata caa tct cct tta tat gga aca gct gca act aca   1008
Asp Leu Asn Thr Ile Gln Ser Pro Leu Tyr Gly Thr Ala Ala Thr Thr
                325                 330                 335 gaa agt cca cgt tta ata att cct ttt aat gag gat tct tat ctt ggt   1056
Glu Ser Pro Arg Leu Ile Ile Pro Phe Asn Glu Asp Ser Tyr Leu Gly
            340                 345                 350 ggt ttt att tat aga aca tta tca tcc cct att tat gta cca cct tct   1104
Gly Phe Ile Tyr Arg Thr Leu Ser Ser Pro Ile Tyr Val Pro Pro Ser
        355                 360                 365 gga att tcg agt caa aga aca tct tta gtg gag ggt gtg gga ttt cag   1152
Gly Ile Ser Ser Gln Arg Thr Ser Leu Val Glu Gly Val Gly Phe Gln
    370                 375                 380 aca ccg aat aac tca ata ctt caa tac aga caa cgt gga aca ttg gat   1200
```

```
Thr Pro Asn Asn Ser Ile Leu Gln Tyr Arg Gln Arg Gly Thr Leu Asp
385                 390                 395                 400 tcc ctt gag caa gta cca ctt caa gaa gag ggg aga cca ggc ggt ttt      1248
Ser Leu Glu Gln Val Pro Leu Gln Glu Glu Gly Arg Pro Gly Gly Phe
                405                 410                 415 ggt gct agt cat aga ttg tgt cat gct aca ttt gct caa tca cct ata      1296
Gly Ala Ser His Arg Leu Cys His Ala Thr Phe Ala Gln Ser Pro Ile
            420                 425                 430 ggt act aac tat tat ata agg gca ccg ttg ttt tct tgg acg cat ctg      1344
Gly Thr Asn Tyr Tyr Ile Arg Ala Pro Leu Phe Ser Trp Thr His Leu
        435                 440                 445 agt gca act ctt act aat gaa gtt cgt gta tct aga att aca caa tta      1392
Ser Ala Thr Leu Thr Asn Glu Val Arg Val Ser Arg Ile Thr Gln Leu
    450                 455                 460 ccg atg gtg aag gcg cat acg ctt cat gcg gga gct act gtt gtt aga      1440
Pro Met Val Lys Ala His Thr Leu His Ala Gly Ala Thr Val Val Arg
465                 470                 475                 480 gga cca gga ttt aca gga gga gat ata ctc cga aga act act tca ggc      1488
Gly Pro Gly Phe Thr Gly Gly Asp Ile Leu Arg Arg Thr Thr Ser Gly
                485                 490                 495 tca ttt ggg gat atg aga ata aca aat ttt tca agt tca tca tcg agg      1536
Ser Phe Gly Asp Met Arg Ile Thr Asn Phe Ser Ser Ser Ser Ser Arg
            500                 505                 510 tat cgt gta aga ata cgt tat gct tct act aca gat tta caa ttt ttc      1584
Tyr Arg Val Arg Ile Arg Tyr Ala Ser Thr Thr Asp Leu Gln Phe Phe
        515                 520                 525 ttg aat gtt gga gga acc cct gtc aat gta gcc gat ttc ccg aaa acc      1632
Leu Asn Val Gly Gly Thr Pro Val Asn Val Ala Asp Phe Pro Lys Thr
    530                 535                 540 ata gat aga ggg gaa aac tta gaa tat gga agc ttt aga acg gca ggt      1680
Ile Asp Arg Gly Glu Asn Leu Glu Tyr Gly Ser Phe Arg Thr Ala Gly
545                 550                 555                 560 ttt act acc cct ttt agt ttt gta agt tca aca aat aat ttc aca tta      1728
Phe Thr Thr Pro Phe Ser Phe Val Ser Ser Thr Asn Asn Phe Thr Leu
                565                 570                 575 ggt gtt cag agt gtt tct tca ggt aac gag att ttt gta gat cga att      1776
Gly Val Gln Ser Val Ser Ser Gly Asn Glu Ile Phe Val Asp Arg Ile
            580                 585                 590 gaa ttt gtt ccg gca gat gca acc ttt gag gca gaa tat gat tta gaa      1824
Glu Phe Val Pro Ala Asp Ala Thr Phe Glu Ala Glu Tyr Asp Leu Glu
        595                 600                 605 aga gcg caa gag gcg gtg aat gct ctg ttt act tct acg aat caa aga      1872
Arg Ala Gln Glu Ala Val Asn Ala Leu Phe Thr Ser Thr Asn Gln Arg
    610                 615                 620 gga ctg aaa aca gat gtg acg gat tat cat att gat caa gtg tcc aat      1920
Gly Leu Lys Thr Asp Val Thr Asp Tyr His Ile Asp Gln Val Ser Asn
625                 630                 635                 640 tta gtg gat tgt tta tcc gat gaa ttc tgt cta gat gaa aaa aga gaa      1968
Leu Val Asp Cys Leu Ser Asp Glu Phe Cys Leu Asp Glu Lys Arg Glu
                645                 650                 655 ttg tcc gaa aaa att aaa cat gca aag cga ctc agt gat gag cgg aat      2016
Leu Ser Glu Lys Ile Lys His Ala Lys Arg Leu Ser Asp Glu Arg Asn
            660                 665                 670 tta ctc caa gat tca aac ttt aga ggc atc aat aga caa cca gat cgt      2064
Leu Leu Gln Asp Ser Asn Phe Arg Gly Ile Asn Arg Gln Pro Asp Arg
        675                 680                 685 ggc tgg aga gga agt acg gat att act atc caa gga gga aat gac gta      2112
Gly Trp Arg Gly Ser Thr Asp Ile Thr Ile Gln Gly Gly Asn Asp Val
    690                 695                 700
```

-continued

| | |
|---|---|
| ttc aaa gaa aat tac gtc aca cta cca ggt acc ttt gat gag tgc tat<br>Phe Lys Glu Asn Tyr Val Thr Leu Pro Gly Thr Phe Asp Glu Cys Tyr<br>705                      710                    715                    720 | 2160 |
| cca aca tat ttg tat caa aaa atc gat gaa tca aaa tta aaa gcc ttt<br>Pro Thr Tyr Leu Tyr Gln Lys Ile Asp Glu Ser Lys Leu Lys Ala Phe<br>              725                    730                    735 | 2208 |
| acc cgt tat caa tta aga ggg tat atc gaa gat agt caa gac tta gaa<br>Thr Arg Tyr Gln Leu Arg Gly Tyr Ile Glu Asp Ser Gln Asp Leu Glu<br>              740                    745                    750 | 2256 |
| atc tat tta att cgc tac aat gca aaa cat gaa aca gta aat gtg cca<br>Ile Tyr Leu Ile Arg Tyr Asn Ala Lys His Glu Thr Val Asn Val Pro<br>755                      760                    765 | 2304 |
| ggt acg ggt tcc tta tgg ccg ctt tca gcc caa agt cca atc gga aag<br>Gly Thr Gly Ser Leu Trp Pro Leu Ser Ala Gln Ser Pro Ile Gly Lys<br>              770                    775                    780 | 2352 |
| tgt gga gag ccg aat cga tgc gcg cca cac ctt gaa tgg aat cct gac<br>Cys Gly Glu Pro Asn Arg Cys Ala Pro His Leu Glu Trp Asn Pro Asp<br>785                      790                    795                    800 | 2400 |
| tta gat tgt tcg tgt agg gat gga gaa aag tgt gcc cat cat tcg cat<br>Leu Asp Cys Ser Cys Arg Asp Gly Glu Lys Cys Ala His His Ser His<br>                          805                    810                    815 | 2448 |
| cat ttc tcc tta gac att gat gta gga tgt aca gac tta aat gag gac<br>His Phe Ser Leu Asp Ile Asp Val Gly Cys Thr Asp Leu Asn Glu Asp<br>              820                    825                    830 | 2496 |
| cta ggt gta tgg gtg atc ttt aag att aag acg caa gat ggg cac gca<br>Leu Gly Val Trp Val Ile Phe Lys Ile Lys Thr Gln Asp Gly His Ala<br>              835                    840                    845 | 2544 |
| aga cta ggg aat cta gag ttt ctc gaa gag aaa cca tta gta gga gaa<br>Arg Leu Gly Asn Leu Glu Phe Leu Glu Glu Lys Pro Leu Val Gly Glu<br>850                      855                    860 | 2592 |
| gcg cta gct cgt gtg aaa aga gcg gag aaa aaa tgg aga gac aaa cgt<br>Ala Leu Ala Arg Val Lys Arg Ala Glu Lys Lys Trp Arg Asp Lys Arg<br>865                      870                    875                    880 | 2640 |
| gaa aaa ttg gaa tgg gaa aca aat atc gtt tat aaa gag gca aaa gaa<br>Glu Lys Leu Glu Trp Glu Thr Asn Ile Val Tyr Lys Glu Ala Lys Glu<br>                          885                    890                    895 | 2688 |
| tct gta gat gct tta ttt gta aac tct caa tat gat caa tta caa gcg<br>Ser Val Asp Ala Leu Phe Val Asn Ser Gln Tyr Asp Gln Leu Gln Ala<br>              900                    905                    910 | 2736 |
| gat acg aat att gcc atg att cat gcg gca gat aaa cgt gtt cat agc<br>Asp Thr Asn Ile Ala Met Ile His Ala Ala Asp Lys Arg Val His Ser<br>                915                    920                    925 | 2784 |
| att cga gaa gct tat ctg cct gag ctg tct gtg att ccg ggt gtc aat<br>Ile Arg Glu Ala Tyr Leu Pro Glu Leu Ser Val Ile Pro Gly Val Asn<br>930                      935                    940 | 2832 |
| gcg gct att ttt gaa gaa tta gaa ggg cgt att ttc act gca ttc tcc<br>Ala Ala Ile Phe Glu Glu Leu Glu Gly Arg Ile Phe Thr Ala Phe Ser<br>945                      950                    955                    960 | 2880 |
| cta tat gat gcg aga aat gtc att aaa aat ggt gat ttt aat aat ggc<br>Leu Tyr Asp Ala Arg Asn Val Ile Lys Asn Gly Asp Phe Asn Asn Gly<br>                965                    970                    975 | 2928 |
| tta tcc tgc tgg aac gtg aaa ggg cat gta gat gta gaa gaa caa aac<br>Leu Ser Cys Trp Asn Val Lys Gly His Val Asp Val Glu Glu Gln Asn<br>              980                    985                    990 | 2976 |
| aac caa cgt tcg gtc ctt gtt gtt   ccg gaa tgg gaa gca   gaa gtg tca<br>Asn Gln Arg Ser Val Leu Val Val   Pro Glu Trp Glu Ala   Glu Val Ser<br>              995                    1000                  1005 | 3024 |
| caa gaa   gtt cgt gtc tgt ccg   ggt cgt ggc tat atc   ctt cgt gtc<br>Gln Glu   Val Arg Val Cys Pro   Gly Arg Gly Tyr Ile   Leu Arg Val<br>          1010                    1015                    1020 | 3069 |

| | | | | | | | | | | | | | | | |
|---|---|---|---|---|---|---|---|---|---|---|---|---|---|---|---|
| aca | gcg | tac | aag | gag | gga | tat | gga | gaa | ggt | tgc | gta | acc | att | cat | 3114 |
| Thr | Ala | Tyr | Lys | Glu | Gly | Tyr | Gly | Glu | Gly | Cys | Val | Thr | Ile | His | |
| | 1025 | | | | | 1030 | | | | | 1035 | | | | |
| gag | atc | gag | aac | aat | aca | gac | gaa | ctg | aag | ttt | agc | aac | tgc | gta | 3159 |
| Glu | Ile | Glu | Asn | Asn | Thr | Asp | Glu | Leu | Lys | Phe | Ser | Asn | Cys | Val | |
| 1040 | | | | | 1045 | | | | | 1050 | | | | | |
| gaa | gag | gaa | atc | tat | cca | aat | aac | acg | gta | acg | tgt | aat | gat | tat | 3204 |
| Glu | Glu | Glu | Ile | Tyr | Pro | Asn | Asn | Thr | Val | Thr | Cys | Asn | Asp | Tyr | |
| 1055 | | | | | 1060 | | | | | 1065 | | | | | |
| act | gta | aat | caa | gaa | gaa | tac | gga | ggt | gcg | tac | act | tct | cgt | aat | 3249 |
| Thr | Val | Asn | Gln | Glu | Glu | Tyr | Gly | Gly | Ala | Tyr | Thr | Ser | Arg | Asn | |
| | 1070 | | | | | 1075 | | | | | 1080 | | | | |
| cga | gga | tat | aac | gaa | gct | cct | tcc | gta | cca | gct | gat | tat | gcg | tca | 3294 |
| Arg | Gly | Tyr | Asn | Glu | Ala | Pro | Ser | Val | Pro | Ala | Asp | Tyr | Ala | Ser | |
| | | 1085 | | | | | 1090 | | | | | 1095 | | | |
| gtc | tat | gaa | gaa | aaa | tcg | tat | aca | gat | gga | cga | aga | gag | aat | cct | 3339 |
| Val | Tyr | Glu | Glu | Lys | Ser | Tyr | Thr | Asp | Gly | Arg | Arg | Glu | Asn | Pro | |
| | | 1100 | | | | | 1105 | | | | | 1110 | | | |
| tgt | gaa | ttt | aac | aga | ggg | tat | agg | gat | tac | acg | cca | cta | cca | gtt | 3384 |
| Cys | Glu | Phe | Asn | Arg | Gly | Tyr | Arg | Asp | Tyr | Thr | Pro | Leu | Pro | Val | |
| | 1115 | | | | | 1120 | | | | | 1125 | | | | |
| ggt | tat | gtg | aca | aaa | gaa | tta | gaa | tac | ttc | cca | gaa | acc | gat | aag | 3429 |
| Gly | Tyr | Val | Thr | Lys | Glu | Leu | Glu | Tyr | Phe | Pro | Glu | Thr | Asp | Lys | |
| 1130 | | | | | 1135 | | | | | 1140 | | | | | |
| gta | tgg | att | gag | att | gga | gaa | acg | gaa | gga | aca | ttt | atc | gtg | gac | 3474 |
| Val | Trp | Ile | Glu | Ile | Gly | Glu | Thr | Glu | Gly | Thr | Phe | Ile | Val | Asp | |
| 1145 | | | | | 1150 | | | | | 1155 | | | | | |
| agc | gtg | gaa | tta | ctc | ctt | atg | gag | gaa | tag | | | | | | 3504 |
| Ser | Val | Glu | Leu | Leu | Leu | Met | Glu | Glu | | | | | | | |
| | 1160 | | | | | 1165 | | | | | | | | | |

<210> SEQ ID NO 40
<211> LENGTH: 1167
<212> TYPE: PRT
<213> ORGANISM: Bacillus thuringiensis

<400> SEQUENCE: 40

Met Glu Arg Asn Asn Gln Asp Gln Cys Ile Pro Tyr Asn Cys Leu Asn
1               5                   10                  15

Asn Pro Glu Ile Glu Ile Leu Asp Val Glu Asn Phe Asn Leu Glu Leu
            20                  25                  30

Val Ser Gln Val Ser Val Gly Leu Thr Arg Phe Leu Leu Glu Ser Ala
        35                  40                  45

Val Pro Gly Ala Gly Phe Ala Leu Gly Leu Phe Asp Ile Ile Trp Gly
    50                  55                  60

Ala Leu Gly Val Asp Gln Trp Ser Leu Phe Leu Ala Gln Ile Glu Gln
65                  70                  75                  80

Leu Ile Asn Glu Arg Ile Thr Thr Val Glu Arg Asn Arg Ala Ile Gln
                85                  90                  95

Thr Leu Ser Gly Leu Ser Ser Ser Tyr Glu Val Tyr Ile Glu Ala Leu
            100                 105                 110

Arg Glu Trp Glu Asn Asn Pro Asp Asn Pro Ala Ser Gln Glu Arg Val
        115                 120                 125

Arg Thr Arg Phe Arg Thr Thr Asp Asp Ala Leu Ile Thr Ala Ile Pro
    130                 135                 140

Asn Leu Ala Ile Pro Asp Phe Glu Ile Ala Thr Leu Ser Val Tyr Val
145                 150                 155                 160

```
Gln Ala Ala Asn Leu His Leu Ser Leu Leu Arg Asp Ala Val Tyr Phe
                165                 170                 175

Gly Glu Arg Trp Gly Leu Thr Gln Val Asn Ile Glu Asp Leu Tyr Thr
            180                 185                 190

Arg Leu Thr Arg Asn Ile His Ile Tyr Ser Asp His Cys Ala Arg Trp
        195                 200                 205

Tyr Asn Gln Gly Leu Asn Asn Ile Gly Ala Thr Asn Thr Arg Tyr Leu
    210                 215                 220

Glu Phe Gln Arg Glu Leu Thr Leu Ser Val Leu Asp Ile Val Ala Leu
225                 230                 235                 240

Phe Pro Asn Tyr Asp Ile Arg Thr Tyr Ser Ile Pro Thr Gln Ser Gln
                245                 250                 255

Leu Thr Arg Glu Ile Tyr Thr Asp Ile Ile Ala Ala Pro Asn Ala Ser
            260                 265                 270

Asn Leu Ile Val Gly Thr Gln Gly Leu Val Arg Ala Pro His Leu Met
        275                 280                 285

Asp Phe Leu Val Arg Leu Asn Ile Tyr Thr Gly Leu Ala Arg Asn Ile
    290                 295                 300

Arg His Trp Ala Gly His Glu Val Ile Ser Arg Thr Gly Gly Val
305                 310                 315                 320

Asp Leu Asn Thr Ile Gln Ser Pro Leu Tyr Gly Thr Ala Ala Thr Thr
                325                 330                 335

Glu Ser Pro Arg Leu Ile Ile Pro Phe Asn Glu Asp Ser Tyr Leu Gly
            340                 345                 350

Gly Phe Ile Tyr Arg Thr Leu Ser Ser Pro Ile Tyr Val Pro Pro Ser
        355                 360                 365

Gly Ile Ser Ser Gln Arg Thr Ser Leu Val Glu Gly Val Gly Phe Gln
    370                 375                 380

Thr Pro Asn Asn Ser Ile Leu Gln Tyr Arg Gln Arg Gly Thr Leu Asp
385                 390                 395                 400

Ser Leu Glu Gln Val Pro Leu Gln Glu Glu Gly Arg Pro Gly Gly Phe
                405                 410                 415

Gly Ala Ser His Arg Leu Cys His Ala Thr Phe Ala Gln Ser Pro Ile
            420                 425                 430

Gly Thr Asn Tyr Tyr Ile Arg Ala Pro Leu Phe Ser Trp Thr His Leu
        435                 440                 445

Ser Ala Thr Leu Thr Asn Glu Val Arg Val Ser Arg Ile Thr Gln Leu
    450                 455                 460

Pro Met Val Lys Ala His Thr Leu His Ala Gly Ala Thr Val Val Arg
465                 470                 475                 480

Gly Pro Gly Phe Thr Gly Gly Asp Ile Leu Arg Arg Thr Ser Gly
                485                 490                 495

Ser Phe Gly Asp Met Arg Ile Thr Asn Phe Ser Ser Ser Ser Arg
            500                 505                 510

Tyr Arg Val Arg Ile Arg Tyr Ala Ser Thr Thr Asp Leu Gln Phe Phe
        515                 520                 525

Leu Asn Val Gly Gly Thr Pro Val Asn Val Ala Asp Phe Pro Lys Thr
    530                 535                 540

Ile Asp Arg Gly Glu Asn Leu Glu Tyr Gly Ser Phe Arg Thr Ala Gly
545                 550                 555                 560

Phe Thr Thr Pro Phe Ser Phe Val Ser Ser Thr Asn Asn Phe Thr Leu
                565                 570                 575

Gly Val Gln Ser Val Ser Ser Gly Asn Glu Ile Phe Val Asp Arg Ile
```

-continued

```
            580                 585                 590
Glu Phe Val Pro Ala Asp Ala Thr Phe Glu Ala Glu Tyr Asp Leu Glu
            595                 600                 605

Arg Ala Gln Glu Ala Val Asn Ala Leu Phe Thr Ser Thr Asn Gln Arg
            610                 615                 620

Gly Leu Lys Thr Asp Val Thr Asp Tyr His Ile Asp Gln Val Ser Asn
625                 630                 635                 640

Leu Val Asp Cys Leu Ser Asp Glu Phe Cys Leu Asp Glu Lys Arg Glu
                    645                 650                 655

Leu Ser Glu Lys Ile Lys His Ala Lys Arg Leu Ser Asp Glu Arg Asn
                660                 665                 670

Leu Leu Gln Asp Ser Asn Phe Arg Gly Ile Asn Arg Gln Pro Asp Arg
                675                 680                 685

Gly Trp Arg Gly Ser Thr Asp Ile Thr Ile Gln Gly Gly Asn Asp Val
            690                 695                 700

Phe Lys Glu Asn Tyr Val Thr Leu Pro Gly Thr Phe Asp Glu Cys Tyr
705                 710                 715                 720

Pro Thr Tyr Leu Tyr Gln Lys Ile Asp Glu Ser Lys Leu Lys Ala Phe
                    725                 730                 735

Thr Arg Tyr Gln Leu Arg Gly Tyr Ile Glu Asp Ser Gln Asp Leu Glu
                740                 745                 750

Ile Tyr Leu Ile Arg Tyr Asn Ala Lys His Glu Thr Val Asn Val Pro
            755                 760                 765

Gly Thr Gly Ser Leu Trp Pro Leu Ser Ala Gln Ser Pro Ile Gly Lys
            770                 775                 780

Cys Gly Glu Pro Asn Arg Cys Ala Pro His Leu Glu Trp Asn Pro Asp
785                 790                 795                 800

Leu Asp Cys Ser Cys Arg Asp Gly Glu Lys Cys Ala His His Ser His
                    805                 810                 815

His Phe Ser Leu Asp Ile Asp Val Gly Cys Thr Asp Leu Asn Glu Asp
                820                 825                 830

Leu Gly Val Trp Val Ile Phe Lys Ile Lys Thr Gln Asp Gly His Ala
            835                 840                 845

Arg Leu Gly Asn Leu Glu Phe Leu Glu Glu Lys Pro Leu Val Gly Glu
850                 855                 860

Ala Leu Ala Arg Val Lys Arg Ala Glu Lys Lys Trp Arg Asp Lys Arg
865                 870                 875                 880

Glu Lys Leu Glu Trp Glu Thr Asn Ile Val Tyr Lys Glu Ala Lys Glu
                    885                 890                 895

Ser Val Asp Ala Leu Phe Val Asn Ser Gln Tyr Asp Gln Leu Gln Ala
                900                 905                 910

Asp Thr Asn Ile Ala Met Ile His Ala Ala Asp Lys Arg Val His Ser
            915                 920                 925

Ile Arg Glu Ala Tyr Leu Pro Glu Leu Ser Val Ile Pro Gly Val Asn
            930                 935                 940

Ala Ala Ile Phe Glu Glu Leu Glu Gly Arg Ile Phe Thr Ala Phe Ser
945                 950                 955                 960

Leu Tyr Asp Ala Arg Asn Val Ile Lys Asn Gly Asp Phe Asn Asn Gly
                    965                 970                 975

Leu Ser Cys Trp Asn Val Lys Gly His Val Asp Val Glu Glu Gln Asn
                980                 985                 990

Asn Gln Arg Ser Val Leu Val Val  Pro Glu Trp Glu Ala  Glu Val Ser
            995                     1000                1005
```

-continued

```
Gln Glu Val Arg Val Cys Pro Gly Arg Gly Tyr Ile Leu Arg Val
    1010                1015                1020

Thr Ala Tyr Lys Glu Gly Tyr Gly Glu Gly Cys Val Thr Ile His
    1025                1030                1035

Glu Ile Glu Asn Asn Thr Asp Glu Leu Lys Phe Ser Asn Cys Val
    1040                1045                1050

Glu Glu Glu Ile Tyr Pro Asn Asn Thr Val Thr Cys Asn Asp Tyr
    1055                1060                1065

Thr Val Asn Gln Glu Glu Tyr Gly Gly Ala Tyr Thr Ser Arg Asn
    1070                1075                1080

Arg Gly Tyr Asn Glu Ala Pro Ser Val Pro Ala Asp Tyr Ala Ser
    1085                1090                1095

Val Tyr Glu Glu Lys Ser Tyr Thr Asp Gly Arg Arg Glu Asn Pro
    1100                1105                1110

Cys Glu Phe Asn Arg Gly Tyr Arg Asp Tyr Thr Pro Leu Pro Val
    1115                1120                1125

Gly Tyr Val Thr Lys Glu Leu Glu Tyr Phe Pro Glu Thr Asp Lys
    1130                1135                1140

Val Trp Ile Glu Ile Gly Glu Thr Glu Gly Thr Phe Ile Val Asp
    1145                1150                1155

Ser Val Glu Leu Leu Leu Met Glu Glu
    1160                1165
```

<210> SEQ ID NO 41
<211> LENGTH: 2133
<212> TYPE: DNA
<213> ORGANISM: Bacillus thuringiensis
<220> FEATURE:
<221> NAME/KEY: CDS
<222> LOCATION: (1)..(2133)
<220> FEATURE:
<221> NAME/KEY: misc_feature
<222> LOCATION: (598)..(600)
<223> OTHER INFORMATION: n = a or g or c or t, unknown, or other

<400> SEQUENCE: 41

```
atg aaa tct aag aat caa aat atg cat caa agc ttg tct aac aat gcg      48
Met Lys Ser Lys Asn Gln Asn Met His Gln Ser Leu Ser Asn Asn Ala
1               5                   10                  15 aca gtt gat aaa aac ttt aca ggt tca cta gaa aat aac aca aat acg      96
Thr Val Asp Lys Asn Phe Thr Gly Ser Leu Glu Asn Asn Thr Asn Thr
            20                  25                  30 gaa tta caa aac ttt aat cat gaa ggt ata gag ccg ttt gtt agt gta     144
Glu Leu Gln Asn Phe Asn His Glu Gly Ile Glu Pro Phe Val Ser Val
        35                  40                  45 tca aca att caa acg ggt att ggt att gct ggt aaa atc ctt ggt aac     192
Ser Thr Ile Gln Thr Gly Ile Gly Ile Ala Gly Lys Ile Leu Gly Asn
    50                  55                  60 cta ggc gtt cct ttt gct ggg caa gta gct agc ctc tat agt ttt atc     240
Leu Gly Val Pro Phe Ala Gly Gln Val Ala Ser Leu Tyr Ser Phe Ile
65                  70                  75                  80 cta ggt gag ctt tgg ccc aaa ggg aaa agc caa tgg gaa atc ttt atg     288
Leu Gly Glu Leu Trp Pro Lys Gly Lys Ser Gln Trp Glu Ile Phe Met
                85                  90                  95 gaa cat gta gaa gag ctt att aat caa aag ata tcg act tat gca aga     336
Glu His Val Glu Glu Leu Ile Asn Gln Lys Ile Ser Thr Tyr Ala Arg
            100                 105                 110 aac aaa gca ctt gca gat tta aaa gga tta gga gat gct ttg gct gtc     384
Asn Lys Ala Leu Ala Asp Leu Lys Gly Leu Gly Asp Ala Leu Ala Val
```

|  |  |  |  |  |  |  |  |  |  |  |  |  |  |  |  |
|---|---|---|---|---|---|---|---|---|---|---|---|---|---|---|---|

```
                 115                 120                 125
tac cat gaa tcg ctg gaa agt tgg att gaa aat cgc aat aac aca aga           432
Tyr His Glu Ser Leu Glu Ser Trp Ile Glu Asn Arg Asn Asn Thr Arg
    130                 135                 140 acc aga agt gtt gtc aag agc caa tac atc acc ttg gaa ctt atg ttc           480
Thr Arg Ser Val Val Lys Ser Gln Tyr Ile Thr Leu Glu Leu Met Phe
145                 150                 155                 160 gta caa tca tta cct tct ttt gca gtg tct gga gag gaa gta cca cta           528
Val Gln Ser Leu Pro Ser Phe Ala Val Ser Gly Glu Glu Val Pro Leu
                165                 170                 175 tta cca ata tat gct caa gct gca aat tta cac tta ttg cta tta cga           576
Leu Pro Ile Tyr Ala Gln Ala Ala Asn Leu His Leu Leu Leu Leu Arg
            180                 185                 190 gat gct tct att ttt gga aaa nnn tgg ggg tta tca gac tca gaa att           624
Asp Ala Ser Ile Phe Gly Lys Xaa Trp Gly Leu Ser Asp Ser Glu Ile
        195                 200                 205 tcc aca ttt tat aat cgc caa tcc gga aaa tcg aaa gaa tat tct gac           672
Ser Thr Phe Tyr Asn Arg Gln Ser Gly Lys Ser Lys Glu Tyr Ser Asp
    210                 215                 220 cac tgc gta aaa tgg tat aat aca ggc cta aat cgc ttg atg ggg aac           720
His Cys Val Lys Trp Tyr Asn Thr Gly Leu Asn Arg Leu Met Gly Asn
225                 230                 235                 240 aat gcc gaa agt tgg gta cga tat aat caa ttc cgt aga gac atg act           768
Asn Ala Glu Ser Trp Val Arg Tyr Asn Gln Phe Arg Arg Asp Met Thr
                245                 250                 255 tta atg gta cta gat tta gtg gca cta ttt cca agc tat gat aca caa           816
Leu Met Val Leu Asp Leu Val Ala Leu Phe Pro Ser Tyr Asp Thr Gln
            260                 265                 270 atg tat cca att aaa act aca gcc caa ctt aca aga gaa gta tat aca           864
Met Tyr Pro Ile Lys Thr Thr Ala Gln Leu Thr Arg Glu Val Tyr Thr
        275                 280                 285 gac gca att ggg aca gta cat ccg cat cca agt ttt aca agt acg act           912
Asp Ala Ile Gly Thr Val His Pro His Pro Ser Phe Thr Ser Thr Thr
    290                 295                 300 tgg tat aat aat aat gca cct tcg ttc tct acc ata gag gct gct gtt           960
Trp Tyr Asn Asn Asn Ala Pro Ser Phe Ser Thr Ile Glu Ala Ala Val
305                 310                 315                 320 gtt cga aac ccg cat cta ctc gat ttt cta gaa caa gtt aca att tac          1008
Val Arg Asn Pro His Leu Leu Asp Phe Leu Glu Gln Val Thr Ile Tyr
                325                 330                 335 agc tta tta agt cga tgg agt aac act cag tat atg aat atg tgg gga          1056
Ser Leu Leu Ser Arg Trp Ser Asn Thr Gln Tyr Met Asn Met Trp Gly
            340                 345                 350 gga cat aaa cta gaa ttc cga aca ata gga gga acg tta aat acc tca          1104
Gly His Lys Leu Glu Phe Arg Thr Ile Gly Gly Thr Leu Asn Thr Ser
        355                 360                 365 aca caa gga tct act aat act tct att aat cct gta aca tta ccg ttc          1152
Thr Gln Gly Ser Thr Asn Thr Ser Ile Asn Pro Val Thr Leu Pro Phe
    370                 375                 380 act tct cga gac gtc tat agg act gaa tca ttg gca ggg ctg aat cta          1200
Thr Ser Arg Asp Val Tyr Arg Thr Glu Ser Leu Ala Gly Leu Asn Leu
385                 390                 395                 400 ttt tta act caa cct gtt aat gga gta cct agg gtt gat ttt cat tgg          1248
Phe Leu Thr Gln Pro Val Asn Gly Val Pro Arg Val Asp Phe His Trp
                405                 410                 415 aaa ttc gtc aca cat ccg atc gca tct gat aat ttc tat tat cca ggg          1296
Lys Phe Val Thr His Pro Ile Ala Ser Asp Asn Phe Tyr Tyr Pro Gly
            420                 425                 430 tat gct gga att ggg acg caa tta cag gat tca gaa aat gaa tta cca          1344
```

```
            Tyr Ala Gly Ile Gly Thr Gln Leu Gln Asp Ser Glu Asn Glu Leu Pro
                    435                 440                 445 cct gaa gca aca gga cag cca aat tat gaa tct tat agt cat aga tta          1392
Pro Glu Ala Thr Gly Gln Pro Asn Tyr Glu Ser Tyr Ser His Arg Leu
    450                 455                 460 tct cat ata gga ctc att tca gca tca cat gtg aaa gca ttg gta tat          1440
Ser His Ile Gly Leu Ile Ser Ala Ser His Val Lys Ala Leu Val Tyr
465                 470                 475                 480 tct tgg acg cat cgt agt gca gat cgt aca aat aca att gag cca aat          1488
Ser Trp Thr His Arg Ser Ala Asp Arg Thr Asn Thr Ile Glu Pro Asn
                485                 490                 495 agc att aca caa ata cca tta gta aaa gcg ttc aat ctg tct tca ggt          1536
Ser Ile Thr Gln Ile Pro Leu Val Lys Ala Phe Asn Leu Ser Ser Gly
            500                 505                 510 gcc gct gta gtg aga gga cca gga ttt aca ggt ggg gat atc ctt cga          1584
Ala Ala Val Val Arg Gly Pro Gly Phe Thr Gly Gly Asp Ile Leu Arg
        515                 520                 525 aga aag aat act ggt aca ttt ggg gat ata cga gta aat att aat cca          1632
Arg Lys Asn Thr Gly Thr Phe Gly Asp Ile Arg Val Asn Ile Asn Pro
    530                 535                 540 cca ttt gca caa aga tat cgc gtg agg att cgc tat gct tct acc aca          1680
Pro Phe Ala Gln Arg Tyr Arg Val Arg Ile Arg Tyr Ala Ser Thr Thr
545                 550                 555                 560 gat tta caa ttc cat acg tca att aac ggt aaa gct att aat caa ggt          1728
Asp Leu Gln Phe His Thr Ser Ile Asn Gly Lys Ala Ile Asn Gln Gly
                565                 570                 575 aat ttt tca gca act atg aat aga gga gag gac tta gac tat aaa acc          1776
Asn Phe Ser Ala Thr Met Asn Arg Gly Glu Asp Leu Asp Tyr Lys Thr
            580                 585                 590 ttt aga act gta ggc ttt acc acc cca ttt agc ttt tca gat gta caa          1824
Phe Arg Thr Val Gly Phe Thr Thr Pro Phe Ser Phe Ser Asp Val Gln
        595                 600                 605 agt aca ttc aca ata ggt gct tgg aac ttc tct tca ggt aac gaa gtt          1872
Ser Thr Phe Thr Ile Gly Ala Trp Asn Phe Ser Ser Gly Asn Glu Val
    610                 615                 620 tat ata gat aga att gaa ttt gtt ccg gta gaa gta aca tat gag gca          1920
Tyr Ile Asp Arg Ile Glu Phe Val Pro Val Glu Val Thr Tyr Glu Ala
625                 630                 635                 640 gaa tat gat ttt gaa aaa gcg caa gag gag gtt act gca ctg ttt aca          1968
Glu Tyr Asp Phe Glu Lys Ala Gln Glu Glu Val Thr Ala Leu Phe Thr
                645                 650                 655 tct acg aat cca aga gga tta aaa aca gat gta aag gat tat cat att          2016
Ser Thr Asn Pro Arg Gly Leu Lys Thr Asp Val Lys Asp Tyr His Ile
            660                 665                 670 gac cag gta tca aat tta gta gag tct cta tca gat aaa ttc tat ctt          2064
Asp Gln Val Ser Asn Leu Val Glu Ser Leu Ser Asp Lys Phe Tyr Leu
        675                 680                 685 gat gaa aag aga gaa tta ttc gag ata gtt aaa tac gcg aag caa ctc          2112
Asp Glu Lys Arg Glu Leu Phe Glu Ile Val Lys Tyr Ala Lys Gln Leu
    690                 695                 700 cat att gag cgt aac atg tag                                              2133
His Ile Glu Arg Asn Met
705                 710

<210> SEQ ID NO 42
<211> LENGTH: 710
<212> TYPE: PRT
<213> ORGANISM: Bacillus thuringiensis
<220> FEATURE:
<221> NAME/KEY: misc_feature
<222> LOCATION: (200)..(200)
```

<223> OTHER INFORMATION: Xaa = unknown or other

<400> SEQUENCE: 42

```
Met Lys Ser Lys Asn Gln Asn Met His Gln Ser Leu Ser Asn Ala
1               5                   10                  15

Thr Val Asp Lys Asn Phe Thr Gly Ser Leu Glu Asn Asn Thr Asn Thr
            20                  25                  30

Glu Leu Gln Asn Phe Asn His Glu Gly Ile Glu Pro Phe Val Ser Val
        35                  40                  45

Ser Thr Ile Gln Thr Gly Ile Gly Ile Ala Gly Lys Ile Leu Gly Asn
    50                  55                  60

Leu Gly Val Pro Phe Ala Gly Gln Val Ala Ser Leu Tyr Ser Phe Ile
65                  70                  75                  80

Leu Gly Glu Leu Trp Pro Lys Gly Lys Ser Gln Trp Glu Ile Phe Met
                85                  90                  95

Glu His Val Glu Glu Leu Ile Asn Gln Lys Ile Ser Thr Tyr Ala Arg
            100                 105                 110

Asn Lys Ala Leu Ala Asp Leu Lys Gly Leu Gly Asp Ala Leu Ala Val
        115                 120                 125

Tyr His Glu Ser Leu Glu Ser Trp Ile Glu Asn Arg Asn Asn Thr Arg
    130                 135                 140

Thr Arg Ser Val Val Lys Ser Gln Tyr Ile Thr Leu Glu Leu Met Phe
145                 150                 155                 160

Val Gln Ser Leu Pro Ser Phe Ala Val Ser Gly Glu Glu Val Pro Leu
                165                 170                 175

Leu Pro Ile Tyr Ala Gln Ala Ala Asn Leu His Leu Leu Leu Leu Arg
            180                 185                 190

Asp Ala Ser Ile Phe Gly Lys Xaa Trp Gly Leu Ser Asp Ser Glu Ile
        195                 200                 205

Ser Thr Phe Tyr Asn Arg Gln Ser Gly Lys Ser Lys Glu Tyr Ser Asp
    210                 215                 220

His Cys Val Lys Trp Tyr Asn Thr Gly Leu Asn Arg Leu Met Gly Asn
225                 230                 235                 240

Asn Ala Glu Ser Trp Val Arg Tyr Asn Gln Phe Arg Arg Asp Met Thr
                245                 250                 255

Leu Met Val Leu Asp Leu Val Ala Leu Phe Pro Ser Tyr Asp Thr Gln
            260                 265                 270

Met Tyr Pro Ile Lys Thr Thr Ala Gln Leu Thr Arg Glu Val Tyr Thr
        275                 280                 285

Asp Ala Ile Gly Thr Val His Pro His Pro Ser Phe Thr Ser Thr Thr
    290                 295                 300

Trp Tyr Asn Asn Asn Ala Pro Ser Phe Ser Thr Ile Glu Ala Ala Val
305                 310                 315                 320

Val Arg Asn Pro His Leu Leu Asp Phe Leu Glu Gln Val Thr Ile Tyr
                325                 330                 335

Ser Leu Leu Ser Arg Trp Ser Asn Thr Gln Tyr Met Asn Met Trp Gly
            340                 345                 350

Gly His Lys Leu Glu Phe Arg Thr Ile Gly Gly Thr Leu Asn Thr Ser
        355                 360                 365

Thr Gln Gly Ser Thr Asn Ser Ile Asn Pro Val Thr Leu Pro Phe
    370                 375                 380

Thr Ser Arg Asp Val Tyr Arg Thr Glu Ser Leu Ala Gly Leu Asn Leu
385                 390                 395                 400
```

```
Phe Leu Thr Gln Pro Val Asn Gly Val Pro Arg Val Asp Phe His Trp
                405                 410                 415
Lys Phe Val Thr His Pro Ile Ala Ser Asp Asn Phe Tyr Tyr Pro Gly
            420                 425                 430
Tyr Ala Gly Ile Gly Thr Gln Leu Gln Asp Ser Glu Asn Glu Leu Pro
        435                 440                 445
Pro Glu Ala Thr Gly Gln Pro Asn Tyr Glu Ser Tyr Ser His Arg Leu
    450                 455                 460
Ser His Ile Gly Leu Ile Ser Ala Ser His Val Lys Ala Leu Val Tyr
465                 470                 475                 480
Ser Trp Thr His Arg Ser Ala Asp Arg Thr Asn Thr Ile Glu Pro Asn
                485                 490                 495
Ser Ile Thr Gln Ile Pro Leu Val Lys Ala Phe Asn Leu Ser Ser Gly
            500                 505                 510
Ala Ala Val Val Arg Gly Pro Gly Phe Thr Gly Gly Asp Ile Leu Arg
        515                 520                 525
Arg Lys Asn Thr Gly Thr Phe Gly Asp Ile Arg Val Asn Ile Asn Pro
    530                 535                 540
Pro Phe Ala Gln Arg Tyr Arg Val Arg Ile Arg Tyr Ala Ser Thr Thr
545                 550                 555                 560
Asp Leu Gln Phe His Thr Ser Ile Asn Gly Lys Ala Ile Asn Gln Gly
                565                 570                 575
Asn Phe Ser Ala Thr Met Asn Arg Gly Glu Asp Leu Asp Tyr Lys Thr
            580                 585                 590
Phe Arg Thr Val Gly Phe Thr Thr Pro Phe Ser Phe Ser Asp Val Gln
        595                 600                 605
Ser Thr Phe Thr Ile Gly Ala Trp Asn Phe Ser Ser Gly Asn Glu Val
    610                 615                 620
Tyr Ile Asp Arg Ile Glu Phe Val Pro Val Glu Val Thr Tyr Glu Ala
625                 630                 635                 640
Glu Tyr Asp Phe Glu Lys Ala Gln Glu Val Thr Ala Leu Phe Thr
                645                 650                 655
Ser Thr Asn Pro Arg Gly Leu Lys Thr Asp Val Lys Asp Tyr His Ile
            660                 665                 670
Asp Gln Val Ser Asn Leu Val Glu Ser Leu Ser Asp Lys Phe Tyr Leu
        675                 680                 685
Asp Glu Lys Arg Glu Leu Phe Glu Ile Val Lys Tyr Ala Lys Gln Leu
    690                 695                 700
His Ile Glu Arg Asn Met
705                 710

<210> SEQ ID NO 43
<211> LENGTH: 218
<212> TYPE: DNA
<213> ORGANISM: Bacillus thuringiensis

<400> SEQUENCE: 43
gtagccgatt tcccgaaaac catagataga ggggaaaact tagaatatgg aagctttaga      60
acggcaggtt ttactacccc ttttagtttt gtaagttcaa caaataattt cacattaggt     120
gttcagagtg tttcttcagg taacgagatt tttgtagatc gaattgaatt tgttccggca     180
gatgcaacct tgaggcaga atatgattta gaaagagc                              218

<210> SEQ ID NO 44
<211> LENGTH: 72
```

-continued

```
<212> TYPE: PRT
<213> ORGANISM: Bacillus thuringiensis

<400> SEQUENCE: 44

Val Ala Asp Phe Pro Lys Thr Ile Asp Arg Gly Glu Asn Leu Glu Tyr
1               5                   10                  15

Gly Ser Phe Arg Thr Ala Gly Phe Thr Thr Pro Phe Ser Phe Val Ser
            20                  25                  30

Ser Thr Asn Asn Phe Thr Leu Gly Val Gln Ser Val Ser Ser Gly Asn
        35                  40                  45

Glu Ile Phe Val Asp Arg Ile Glu Phe Val Pro Ala Asp Ala Thr Phe
    50                  55                  60

Glu Ala Glu Tyr Asp Leu Glu Arg
65                  70

<210> SEQ ID NO 45
<211> LENGTH: 1908
<212> TYPE: DNA
<213> ORGANISM: Bacillus thuringiensis
<220> FEATURE:
<221> NAME/KEY: CDS
<222> LOCATION: (1)..(1908)

<400> SEQUENCE: 45
```

| | |
|---|---|
| atg aat aat gta ttg aat agc gga aaa aca act att tgt aat gcg tat<br>Met Asn Asn Val Leu Asn Ser Gly Lys Thr Thr Ile Cys Asn Ala Tyr<br>1               5                   10                  15 | 48 |
| aat gta gtg gct cac gat cca ttt agt ttt gaa cat aaa tca tta gat<br>Asn Val Val Ala His Asp Pro Phe Ser Phe Glu His Lys Ser Leu Asp<br>            20                  25                  30 | 96 |
| acc atc caa gaa gaa tgg atg gag tgg aaa aga aca gat cat agt tta<br>Thr Ile Gln Glu Glu Trp Met Glu Trp Lys Arg Thr Asp His Ser Leu<br>        35                  40                  45 | 144 |
| tat gta gct cct gta gtc gga act gtg tct agt ttt ctg cta aag aaa<br>Tyr Val Ala Pro Val Val Gly Thr Val Ser Ser Phe Leu Leu Lys Lys<br>    50                  55                  60 | 192 |
| gtg ggg agt cta att gga aaa agg ata ttg agt gaa tta tgg ggg tta<br>Val Gly Ser Leu Ile Gly Lys Arg Ile Leu Ser Glu Leu Trp Gly Leu<br>65                  70                  75                  80 | 240 |
| ata ttt cct agt ggt agt aca aat cta atg caa gat att tta aga gag<br>Ile Phe Pro Ser Gly Ser Thr Asn Leu Met Gln Asp Ile Leu Arg Glu<br>                85                  90                  95 | 288 |
| aca gaa caa ttc cta aat caa aga ctt aat aca gac acc ctt gat cgt<br>Thr Glu Gln Phe Leu Asn Gln Arg Leu Asn Thr Asp Thr Leu Asp Arg<br>            100                 105                 110 | 336 |
| gta aat gca gaa ttg gaa ggg ctc caa gcg aat ata agg gag ttt aat<br>Val Asn Ala Glu Leu Glu Gly Leu Gln Ala Asn Ile Arg Glu Phe Asn<br>        115                 120                 125 | 384 |
| caa caa gta gat aat ttt tta aac cct act caa aac cct gtt cct tta<br>Gln Gln Val Asp Asn Phe Leu Asn Pro Thr Gln Asn Pro Val Pro Leu<br>    130                 135                 140 | 432 |
| tca ata act tct tca gtt aat aca atg cag caa tta ttt cta aat aga<br>Ser Ile Thr Ser Ser Val Asn Thr Met Gln Gln Leu Phe Leu Asn Arg<br>145                 150                 155                 160 | 480 |
| tta ccc cag ttc cag ata caa gga tac cag ttg tta tta cct tta<br>Leu Pro Gln Phe Gln Ile Gln Gly Tyr Gln Leu Leu Leu Pro Leu<br>                165                 170                 175 | 528 |
| ttt gca cag gca gcc aat atg cat ctt tct ttt att aga gat gtt att<br>Phe Ala Gln Ala Ala Asn Met His Leu Ser Phe Ile Arg Asp Val Ile<br>            180                 185                 190 | 576 |

```
ctt aat gca gat gaa tgg ggc att tca gca gca aca cta cgt acg tat       624
Leu Asn Ala Asp Glu Trp Gly Ile Ser Ala Ala Thr Leu Arg Thr Tyr
        195                 200                 205 cga gac tac ctg aga aat tat aca aga gat tat tct aat tat tgt ata       672
Arg Asp Tyr Leu Arg Asn Tyr Thr Arg Asp Tyr Ser Asn Tyr Cys Ile
        210                 215                 220 aat acg tat caa act gcg ttt aga ggg tta aac acc cgt tta cac gat       720
Asn Thr Tyr Gln Thr Ala Phe Arg Gly Leu Asn Thr Arg Leu His Asp
225                 230                 235                 240 atg tta gaa ttt aga aca tat atg ttt tta aat gta ttt gaa tat gta       768
Met Leu Glu Phe Arg Thr Tyr Met Phe Leu Asn Val Phe Glu Tyr Val
                245                 250                 255 tcc att tgg tca ttg ttt aaa tat cag agt ctt atg gta tct tct ggc       816
Ser Ile Trp Ser Leu Phe Lys Tyr Gln Ser Leu Met Val Ser Ser Gly
            260                 265                 270 gct aat tta tat gct agt ggt agt gga cca cag cag aca caa tca ttt       864
Ala Asn Leu Tyr Ala Ser Gly Ser Gly Pro Gln Gln Thr Gln Ser Phe
        275                 280                 285 act gca caa aac tgg cca ttt tta tat tct ctt ttc caa gtt aat tcg       912
Thr Ala Gln Asn Trp Pro Phe Leu Tyr Ser Leu Phe Gln Val Asn Ser
        290                 295                 300 aat tat ata tta tct ggt att agt ggt aat agg ctt tct act acc ttc       960
Asn Tyr Ile Leu Ser Gly Ile Ser Gly Asn Arg Leu Ser Thr Thr Phe
305                 310                 315                 320 cct aat att ggt ggt tta ccg ggt agt act aca att cat tca ttg aac      1008
Pro Asn Ile Gly Gly Leu Pro Gly Ser Thr Thr Ile His Ser Leu Asn
                325                 330                 335 agt gcc agg gtt aat tat agc gga gga gtt tca tct ggt ctc ata ggg      1056
Ser Ala Arg Val Asn Tyr Ser Gly Gly Val Ser Ser Gly Leu Ile Gly
            340                 345                 350 gcg act aat ctc aat cac aac ttt aat tgc agc acg gtc ctc cct cct      1104
Ala Thr Asn Leu Asn His Asn Phe Asn Cys Ser Thr Val Leu Pro Pro
        355                 360                 365 tta tca aca cca ttt gtt aga agt tgg ctg gat tca ggt aca gat cga      1152
Leu Ser Thr Pro Phe Val Arg Ser Trp Leu Asp Ser Gly Thr Asp Arg
        370                 375                 380 gag ggc gtt gct acc tct acg act tgg cag aca gaa tcc ttc caa ata      1200
Glu Gly Val Ala Thr Ser Thr Thr Trp Gln Thr Glu Ser Phe Gln Ile
385                 390                 395                 400 act tca ggt tta agg tgt ggt gct ttt cct ttt tca gct cgt gga aat      1248
Thr Ser Gly Leu Arg Cys Gly Ala Phe Pro Phe Ser Ala Arg Gly Asn
                405                 410                 415 tca aac tat ttc cca gat tat ttt atc cgt aat att tct ggg gtt cct      1296
Ser Asn Tyr Phe Pro Asp Tyr Phe Ile Arg Asn Ile Ser Gly Val Pro
            420                 425                 430 tta gtt att aga aac gaa gat cta aca aga ccg tta cac tat aac caa      1344
Leu Val Ile Arg Asn Glu Asp Leu Thr Arg Pro Leu His Tyr Asn Gln
        435                 440                 445 ata aga aat ata gaa agt cct tcg gga aca cct ggt gga tta cga gct      1392
Ile Arg Asn Ile Glu Ser Pro Ser Gly Thr Pro Gly Gly Leu Arg Ala
450                 455                 460 tat atg gta tct gtg cat aac aga aaa aat aat atc tat gcc gct cat      1440
Tyr Met Val Ser Val His Asn Arg Lys Asn Asn Ile Tyr Ala Ala His
465                 470                 475                 480 gaa aat ggt act atg att cat ttg gca ccg gaa gat tat aca gga ttt      1488
Glu Asn Gly Thr Met Ile His Leu Ala Pro Glu Asp Tyr Thr Gly Phe
                485                 490                 495 act ata tca cca ata cat gcc act caa gtg aat aat caa act cga aca      1536
Thr Ile Ser Pro Ile His Ala Thr Gln Val Asn Asn Gln Thr Arg Thr
        500                 505                 510
```

-continued

```
ttt att tct gaa aaa ttt gga aat caa ggt gat tcc tta aga ttt gaa      1584
Phe Ile Ser Glu Lys Phe Gly Asn Gln Gly Asp Ser Leu Arg Phe Glu
    515                 520                 525 caa agt aac acg aca gct cgt tat acg ctt aga ggg aat gga aat agt      1632
Gln Ser Asn Thr Thr Ala Arg Tyr Thr Leu Arg Gly Asn Gly Asn Ser
530                 535                 540 tac aat ctt tat tta aga gta tct tca ata gga aat tca act atc cga      1680
Tyr Asn Leu Tyr Leu Arg Val Ser Ser Ile Gly Asn Ser Thr Ile Arg
545                 550                 555                 560 gtt act ata aac ggt agg gtt tat act gct tca aat gtt aat act aat      1728
Val Thr Ile Asn Gly Arg Val Tyr Thr Ala Ser Asn Val Asn Thr Asn
                565                 570                 575 aca aat aac gat ggg gtt aat gat aat gga gct cgt ttt tca gat att      1776
Thr Asn Asn Asp Gly Val Asn Asp Asn Gly Ala Arg Phe Ser Asp Ile
            580                 585                 590 aat atc ggt aat gta gta gca agt gat aat act aat gta ccg tta gat      1824
Asn Ile Gly Asn Val Val Ala Ser Asp Asn Thr Asn Val Pro Leu Asp
        595                 600                 605 ata aat gtg aca tta aac tcc ggt act caa ttt gag ctt atg aat att      1872
Ile Asn Val Thr Leu Asn Ser Gly Thr Gln Phe Glu Leu Met Asn Ile
    610                 615                 620 atg ttt gtg cca act aat ctt cca cca ctt tat taa                      1908
Met Phe Val Pro Thr Asn Leu Pro Pro Leu Tyr
625                 630                 635

<210> SEQ ID NO 46
<211> LENGTH: 635
<212> TYPE: PRT
<213> ORGANISM: Bacillus thuringiensis

<400> SEQUENCE: 46

Met Asn Asn Val Leu Asn Ser Gly Lys Thr Thr Ile Cys Asn Ala Tyr
1               5                   10                  15

Asn Val Val Ala His Asp Pro Phe Ser Phe Glu His Lys Ser Leu Asp
                20                  25                  30

Thr Ile Gln Glu Glu Trp Met Glu Trp Lys Arg Thr Asp His Ser Leu
            35                  40                  45

Tyr Val Ala Pro Val Val Gly Thr Val Ser Ser Phe Leu Leu Lys Lys
        50                  55                  60

Val Gly Ser Leu Ile Gly Lys Arg Ile Leu Ser Glu Leu Trp Gly Leu
65                  70                  75                  80

Ile Phe Pro Ser Gly Ser Thr Asn Leu Met Gln Asp Ile Leu Arg Glu
                85                  90                  95

Thr Glu Gln Phe Leu Asn Gln Arg Leu Asn Thr Asp Thr Leu Asp Arg
            100                 105                 110

Val Asn Ala Glu Leu Glu Gly Leu Gln Ala Asn Ile Arg Glu Phe Asn
        115                 120                 125

Gln Gln Val Asp Asn Phe Leu Asn Pro Thr Gln Asn Pro Val Pro Leu
    130                 135                 140

Ser Ile Thr Ser Ser Val Asn Thr Met Gln Gln Leu Phe Leu Asn Arg
145                 150                 155                 160

Leu Pro Gln Phe Gln Ile Gln Gly Tyr Gln Leu Leu Leu Leu Pro Leu
                165                 170                 175

Phe Ala Gln Ala Ala Asn Met His Leu Ser Phe Ile Arg Asp Val Ile
            180                 185                 190

Leu Asn Ala Asp Glu Trp Gly Ile Ser Ala Ala Thr Leu Arg Thr Tyr
        195                 200                 205
```

```
Arg Asp Tyr Leu Arg Asn Tyr Thr Arg Asp Tyr Ser Asn Tyr Cys Ile
    210                 215                 220

Asn Thr Tyr Gln Thr Ala Phe Arg Gly Leu Asn Thr Arg Leu His Asp
225                 230                 235                 240

Met Leu Glu Phe Arg Thr Tyr Met Phe Leu Asn Val Phe Glu Tyr Val
                245                 250                 255

Ser Ile Trp Ser Leu Phe Lys Tyr Gln Ser Leu Met Val Ser Ser Gly
            260                 265                 270

Ala Asn Leu Tyr Ala Ser Gly Ser Gly Pro Gln Gln Thr Gln Ser Phe
        275                 280                 285

Thr Ala Gln Asn Trp Pro Phe Leu Tyr Ser Leu Phe Gln Val Asn Ser
290                 295                 300

Asn Tyr Ile Leu Ser Gly Ile Ser Gly Asn Arg Leu Ser Thr Thr Phe
305                 310                 315                 320

Pro Asn Ile Gly Gly Leu Pro Gly Ser Thr Thr Ile His Ser Leu Asn
                325                 330                 335

Ser Ala Arg Val Asn Tyr Ser Gly Gly Val Ser Ser Gly Leu Ile Gly
            340                 345                 350

Ala Thr Asn Leu Asn His Asn Phe Asn Cys Ser Thr Val Leu Pro Pro
        355                 360                 365

Leu Ser Thr Pro Phe Val Arg Ser Trp Leu Asp Ser Gly Thr Asp Arg
370                 375                 380

Glu Gly Val Ala Thr Ser Thr Thr Trp Gln Thr Glu Ser Phe Gln Ile
385                 390                 395                 400

Thr Ser Gly Leu Arg Cys Gly Ala Phe Pro Phe Ser Ala Arg Gly Asn
                405                 410                 415

Ser Asn Tyr Phe Pro Asp Tyr Phe Ile Arg Asn Ile Ser Gly Val Pro
            420                 425                 430

Leu Val Ile Arg Asn Glu Asp Leu Thr Arg Pro Leu His Tyr Asn Gln
        435                 440                 445

Ile Arg Asn Ile Glu Ser Pro Ser Gly Thr Pro Gly Gly Leu Arg Ala
450                 455                 460

Tyr Met Val Ser Val His Asn Arg Lys Asn Asn Ile Tyr Ala Ala His
465                 470                 475                 480

Glu Asn Gly Thr Met Ile His Leu Ala Pro Glu Asp Tyr Thr Gly Phe
                485                 490                 495

Thr Ile Ser Pro Ile His Ala Thr Gln Val Asn Asn Gln Thr Arg Thr
            500                 505                 510

Phe Ile Ser Glu Lys Phe Gly Asn Gln Gly Asp Ser Leu Arg Phe Glu
        515                 520                 525

Gln Ser Asn Thr Thr Ala Arg Tyr Thr Leu Arg Gly Asn Gly Asn Ser
530                 535                 540

Tyr Asn Leu Tyr Leu Arg Val Ser Ser Ile Gly Asn Ser Thr Ile Arg
545                 550                 555                 560

Val Thr Ile Asn Gly Arg Val Tyr Thr Ala Ser Asn Val Asn Thr Asn
                565                 570                 575

Thr Asn Asn Asp Gly Val Asn Asp Asn Gly Ala Arg Phe Ser Asp Ile
            580                 585                 590

Asn Ile Gly Asn Val Val Ala Ser Asp Asn Thr Asn Val Pro Leu Asp
        595                 600                 605

Ile Asn Val Thr Leu Asn Ser Gly Thr Gln Phe Glu Leu Met Asn Ile
610                 615                 620
```

```
Met Phe Val Pro Thr Asn Leu Pro Pro Leu Tyr
625                 630                 635

<210> SEQ ID NO 47
<211> LENGTH: 1878
<212> TYPE: DNA
<213> ORGANISM: Bacillus thuringiensis
<220> FEATURE:
<221> NAME/KEY: CDS
<222> LOCATION: (1)..(1878)

<400> SEQUENCE: 47 atg a

-continued

```
                Ser Ile Trp Ser Leu Phe Lys Tyr Gln Ser Leu Leu Val Ser Ser Gly
                            260                 265                 270 gct aat tta tat gcg agt ggt agt ggt cca aca caa tca ttt aca gca           864
Ala Asn Leu Tyr Ala Ser Gly Ser Gly Pro Thr Gln Ser Phe Thr Ala
            275                 280                 285 caa aac tgg cca ttt tta tat tct ctt ttc caa gtt aat tct aat tat           912
Gln Asn Trp Pro Phe Leu Tyr Ser Leu Phe Gln Val Asn Ser Asn Tyr
            290                 295                 300 gta tta aat ggt ttg agt ggt gct agg acc acc att act ttc cct aat           960
Val Leu Asn Gly Leu Ser Gly Ala Arg Thr Thr Ile Thr Phe Pro Asn
305                 310                 315                 320 att ggt ggt ctt ccc ggt tct acc aca act caa aca ttg cat ttt gcg          1008
Ile Gly Gly Leu Pro Gly Ser Thr Thr Thr Gln Thr Leu His Phe Ala
                325                 330                 335 agg att aat tat aga ggt gga gtg tca tct agc cgc ata ggt caa gct          1056
Arg Ile Asn Tyr Arg Gly Gly Val Ser Ser Ser Arg Ile Gly Gln Ala
                340                 345                 350 aat ctt aat caa aac ttt aac att tcc aca ctt ttc aat cct tta caa          1104
Asn Leu Asn Gln Asn Phe Asn Ile Ser Thr Leu Phe Asn Pro Leu Gln
            355                 360                 365 aca ccg ttt att aga agt tgg cta gat tct ggt aca gat cgg gag ggc          1152
Thr Pro Phe Ile Arg Ser Trp Leu Asp Ser Gly Thr Asp Arg Glu Gly
            370                 375                 380 gtt gcc acc tct aca aac tgg caa tca gga gcc ttt gag aca act tta          1200
Val Ala Thr Ser Thr Asn Trp Gln Ser Gly Ala Phe Glu Thr Thr Leu
385                 390                 395                 400 tta cga ttt agc att ttt tca gct cgt ggt aat tcg aac ttt ttc cca          1248
Leu Arg Phe Ser Ile Phe Ser Ala Arg Gly Asn Ser Asn Phe Phe Pro
                405                 410                 415 gat tat ttt atc cgt aat att tct ggt gtt gtt ggg act att agc aac          1296
Asp Tyr Phe Ile Arg Asn Ile Ser Gly Val Val Gly Thr Ile Ser Asn
                420                 425                 430 gca gat tta gca aga cct cta cac ttt aat gaa ata aga gat ata gga          1344
Ala Asp Leu Ala Arg Pro Leu His Phe Asn Glu Ile Arg Asp Ile Gly
            435                 440                 445 acg aca gca gtc gct agc ctt gta aca gtg cat aac aga aaa aat aat          1392
Thr Thr Ala Val Ala Ser Leu Val Thr Val His Asn Arg Lys Asn Asn
            450                 455                 460 atc tat gac act cat gaa aat ggt act atg att cat tta gcg cca aat          1440
Ile Tyr Asp Thr His Glu Asn Gly Thr Met Ile His Leu Ala Pro Asn
465                 470                 475                 480 gac tat aca gga ttt acc gta tct cca ata cat gcc act caa gta aat          1488
Asp Tyr Thr Gly Phe Thr Val Ser Pro Ile His Ala Thr Gln Val Asn
                485                 490                 495 aat caa att cga acg ttt att tcc gaa aaa tat ggt aat cag ggt gat          1536
Asn Gln Ile Arg Thr Phe Ile Ser Glu Lys Tyr Gly Asn Gln Gly Asp
            500                 505                 510 tcc ttg aga ttt gag cta agc aac aca acg gct cga tac aca ctt aga          1584
Ser Leu Arg Phe Glu Leu Ser Asn Thr Thr Ala Arg Tyr Thr Leu Arg
            515                 520                 525 ggg aat gga aat agt tac aat ctt tat tta aga gta tct tca ata gga          1632
Gly Asn Gly Asn Ser Tyr Asn Leu Tyr Leu Arg Val Ser Ser Ile Gly
530                 535                 540 agt tcc aca att cga gtt act ata aac ggt aga gtt tat act gca aat          1680
Ser Ser Thr Ile Arg Val Thr Ile Asn Gly Arg Val Tyr Thr Ala Asn
545                 550                 555                 560 gtt aat act acc aca aat aat gat gga gta ctt gat aat gga gct cgt          1728
Val Asn Thr Thr Thr Asn Asn Asp Gly Val Leu Asp Asn Gly Ala Arg
                565                 570                 575
```

```
ttt tca gat att aat atc ggt aat gta gtg gca agt gct aat act aat    1776
Phe Ser Asp Ile Asn Ile Gly Asn Val Val Ala Ser Ala Asn Thr Asn
        580                 585                 590 gta cca tta gat ata caa gtg aca ttt aac gac aat cca caa ttt gag    1824
Val Pro Leu Asp Ile Gln Val Thr Phe Asn Asp Asn Pro Gln Phe Glu
            595                 600                 605 ctt atg aat att atg ttg ttc caa cta atc ttc cac cac ttt att aag    1872
Leu Met Asn Ile Met Leu Phe Gln Leu Ile Phe His His Phe Ile Lys
    610                 615                 620 gtt tga                                                             1878
Val
625

<210> SEQ ID NO 48
<211> LENGTH: 625
<212> TYPE: PRT
<213> ORGANISM: Bacillus thuringiensis

<400> SEQUENCE: 48

Met Asn Thr Val Leu Asn Asn Gly Arg Asn Thr Thr Cys His Ala His
1               5                   10                  15

Asn Val Val Ala His Asp Pro Phe Ser Phe Glu His Lys Ser Leu Asn
            20                  25                  30

Thr Ile Glu Lys Glu Trp Lys Glu Trp Lys Arg Thr Asp His Ser Leu
        35                  40                  45

Tyr Val Ala Pro Ile Val Gly Thr Val Gly Ser Phe Leu Leu Lys Lys
    50                  55                  60

Val Gly Ser Leu Val Gly Lys Arg Ile Leu Ser Glu Leu Gln Asn Leu
65                  70                  75                  80

Ile Phe Pro Ser Gly Ser Ile Asp Leu Met Gln Glu Ile Leu Arg Ala
                85                  90                  95

Thr Glu Gln Phe Ile Asn Gln Arg Leu Asn Ala Asp Thr Leu Gly Arg
            100                 105                 110

Val Asn Ala Glu Leu Ala Gly Leu Gln Ala Asn Val Ala Glu Phe Asn
        115                 120                 125

Arg Gln Val Asp Asn Phe Leu Asn Pro Asn Gln Asn Pro Val Pro Leu
    130                 135                 140

Ala Ile Ile Asp Ser Val Asn Thr Leu Gln Gln Leu Phe Leu Ser Arg
145                 150                 155                 160

Leu Pro Gln Phe Gln Ile Gln Gly Tyr Gln Leu Leu Leu Pro Leu
                165                 170                 175

Phe Ala Gln Ala Ala Asn Leu His Leu Ser Phe Ile Arg Asp Val Ile
            180                 185                 190

Leu Asn Ala Asp Glu Trp Gly Ile Ser Ala Ala Thr Val Arg Thr Tyr
        195                 200                 205

Arg Asp His Leu Arg Asn Phe Thr Arg Asp Tyr Ser Asn Tyr Cys Ile
    210                 215                 220

Asn Thr Tyr Gln Thr Ala Phe Arg Gly Leu Asn Thr Arg Leu His Asp
225                 230                 235                 240

Met Leu Glu Phe Arg Thr Tyr Met Phe Leu Asn Val Phe Glu Tyr Val
                245                 250                 255

Ser Ile Trp Ser Leu Phe Lys Tyr Gln Ser Leu Leu Val Ser Ser Gly
            260                 265                 270

Ala Asn Leu Tyr Ala Ser Gly Ser Gly Pro Thr Gln Ser Phe Thr Ala
        275                 280                 285

Gln Asn Trp Pro Phe Leu Tyr Ser Leu Phe Gln Val Asn Ser Asn Tyr
```

```
                290                 295                 300
Val Leu Asn Gly Leu Ser Gly Ala Arg Thr Thr Ile Thr Phe Pro Asn
305                 310                 315                 320

Ile Gly Gly Leu Pro Gly Ser Thr Thr Thr Gln Thr Leu His Phe Ala
            325                 330                 335

Arg Ile Asn Tyr Arg Gly Gly Val Ser Ser Arg Ile Gly Gln Ala
            340                 345                 350

Asn Leu Asn Gln Asn Phe Asn Ile Ser Thr Leu Phe Asn Pro Leu Gln
            355                 360                 365

Thr Pro Phe Ile Arg Ser Trp Leu Asp Ser Gly Thr Asp Arg Glu Gly
370                 375                 380

Val Ala Thr Ser Thr Asn Trp Gln Ser Gly Ala Phe Glu Thr Thr Leu
385                 390                 395                 400

Leu Arg Phe Ser Ile Phe Ser Ala Arg Gly Asn Ser Asn Phe Phe Pro
            405                 410                 415

Asp Tyr Phe Ile Arg Asn Ile Ser Gly Val Val Gly Thr Ile Ser Asn
            420                 425                 430

Ala Asp Leu Ala Arg Pro Leu His Phe Asn Glu Ile Arg Asp Ile Gly
            435                 440                 445

Thr Thr Ala Val Ala Ser Leu Val Thr Val His Asn Arg Lys Asn Asn
450                 455                 460

Ile Tyr Asp Thr His Glu Asn Gly Thr Met Ile His Leu Ala Pro Asn
465                 470                 475                 480

Asp Tyr Thr Gly Phe Thr Val Ser Pro Ile His Ala Thr Gln Val Asn
            485                 490                 495

Asn Gln Ile Arg Thr Phe Ile Ser Glu Lys Tyr Gly Asn Gln Gly Asp
            500                 505                 510

Ser Leu Arg Phe Glu Leu Ser Asn Thr Thr Ala Arg Tyr Thr Leu Arg
            515                 520                 525

Gly Asn Gly Asn Ser Tyr Asn Leu Tyr Leu Arg Val Ser Ser Ile Gly
            530                 535                 540

Ser Ser Thr Ile Arg Val Thr Ile Asn Gly Arg Val Tyr Thr Ala Asn
545                 550                 555                 560

Val Asn Thr Thr Thr Asn Asn Asp Gly Val Leu Asp Asn Gly Ala Arg
            565                 570                 575

Phe Ser Asp Ile Asn Ile Gly Asn Val Val Ala Ser Ala Asn Thr Asn
            580                 585                 590

Val Pro Leu Asp Ile Gln Val Thr Phe Asn Asp Asn Pro Gln Phe Glu
            595                 600                 605

Leu Met Asn Ile Met Leu Phe Gln Leu Ile Phe His His Phe Ile Lys
610                 615                 620

Val
625

<210> SEQ ID NO 49
<211> LENGTH: 143
<212> TYPE: DNA
<213> ORGANISM: Bacillus thuringiensis
<220> FEATURE:
<221> NAME/KEY: modified_base
<222> LOCATION: (8)..(140)
<223> OTHER INFORMATION: N = A, T, C or G
<220> FEATURE:
<221> NAME/KEY: misc_feature
<222> LOCATION: (8)..(8)
<223> OTHER INFORMATION: n is a, c, g, or t
<220> FEATURE:
```

<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t

<400> SEQUENCE: 49
gtcgtganag gnccaggatt tacaggaggg gatatactnc gaagaacggn cggtggtgca      60
tttggaacna ttagngctan ggctantgcc ccnttaacac aacaatatcg nataagatta    120
cgctntgctt ctacnacaan ttt                                            143

<210> SEQ ID NO 50
<211> LENGTH: 47
<212> TYPE: PRT
<213> ORGANISM: Bacillus thuringiensis
<220> FEATURE:
<221> NAME/KEY: SITE
<222> LOCATION: (3)..(3)
<223> OTHER INFORMATION: X = R, I, K, or T
<220> FEATURE:
<221> NAME/KEY: SITE
<222> LOCATION: (17)..(17)
<223> OTHER INFORMATION: X =A, D, G or V
<220> FEATURE:
<221> NAME/KEY: SITE
<222> LOCATION: (25)..(25)
<223> OTHER INFORMATION: X = S or R
<220> FEATURE:
<221> NAME/KEY: SITE
<222> LOCATION: (27)..(27)
<223> OTHER INFORMATION: X = R, K, M, or T
<220> FEATURE:
<221> NAME/KEY: SITE

```
<222> LOCATION: (29)..(29)
<223> OTHER INFORMATION: X = N, I, S, or T
<220> FEATURE:
<221> NAME/KEY: SITE
<222> LOCATION: (42)..(42)
<223> OTHER INFORMATION: X = C, F, S, or Y
<220> FEATURE:
<221> NAME/KEY: SITE
<222> LOCATION: (47)..(47)
<223> OTHER INFORMATION: X = N, I, S, or T

<400> SEQUENCE: 50

Val Val Xaa Gly Pro Gly Phe Thr Gly Asp Ile Leu Arg Arg Thr
1               5                   10                  15

Xaa Gly Gly Ala Phe Gly Thr Ile Xaa Ala Xaa Ala Xaa Ala Pro Leu
            20                  25              30

Thr Gln Gln Tyr Arg Ile Arg Leu Arg Xaa Ala Ser Thr Thr Xaa
            35                  40                  45

<210> SEQ ID NO 51
<211> LENGTH: 42
<212> TYPE: DNA
<213> ORGANISM: Artificial
<220> FEATURE:
<223> OTHER INFORMATION: Primer

<400> SEQUENCE: 51
tggatacttg atcaatatga taatccgtca catctgtttt ta                    42

<210> SEQ ID NO 52
<211> LENGTH: 61
<212> TYPE: DNA
<213> ORGANISM: Artificial
<220> FEATURE:
<223> OTHER INFORMATION: Primer

<400> SEQUENCE: 52
agtaacggtg ttactattag cgagggcggt ccattcttta aggtcgtgca cttcagttag    60
c                                                                    61

<210> SEQ ID NO 53
<211> LENGTH: 22
<212> TYPE: DNA
<213> ORGANISM: Artificial
<220> FEATURE:
<223> OTHER INFORMATION: Primer

<400> SEQUENCE: 53
cgacttctcc tgctaatgga gg                                          22

<210> SEQ ID NO 54
<211> LENGTH: 28
<212> TYPE: DNA
<213> ORGANISM: Artificial
<220> FEATURE:
<223> OTHER INFORMATION: Primer

<400> SEQUENCE: 54
ctcgctaata gtaacaccgt tacttgcc                                    28

<210> SEQ ID NO 55
<211> LENGTH: 61
<212> TYPE: DNA
<213> ORGANISM: Artificial
<220> FEATURE:
<223> OTHER INFORMATION: Primer
```

```
<400> SEQUENCE: 55
atttagtagc atgcgttgca ctttgtgcat tttttcataa gatgagtcat atgttttaaa    60
t                                                                   61

<210> SEQ ID NO 56
<211> LENGTH: 23
<212> TYPE: DNA
<213> ORGANISM: Artificial
<220> FEATURE:
<223> OTHER INFORMATION: Primer

<400> SEQUENCE: 56
ggatagcact catcaaaggt acc                                           23

<210> SEQ ID NO 57
<211> LENGTH: 22
<212> TYPE: DNA
<213> ORGANISM: Artificial
<220> FEATURE:
<223> OTHER INFORMATION: Primer

<400> SEQUENCE: 57
gtwtggacsc rtcghgatgt gg                                            22

<210> SEQ ID NO 58
<211> LENGTH: 40
<212> TYPE: DNA
<213> ORGANISM: Artificial
<220> FEATURE:
<223> OTHER INFORMATION: Primer

<400> SEQUENCE: 58
taatttctgc tagcccwatt tctggattta attgttgatc                         40

<210> SEQ ID NO 59
<211> LENGTH: 19
<212> TYPE: DNA
<213> ORGANISM: Artificial
<220> FEATURE:
<223> OTHER INFORMATION: Primer
<220> FEATURE:
<221> NAME/KEY: modified_base
<222> LOCATION: (3)..(12)
<223> OTHER INFORMATION: W = A, T
<220> FEATURE:
<221> NAME/KEY: modified_base
<222> LOCATION: (6)..(6)
<223> OTHER INFORMATION: N = A, C, T
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (10)..(10)
<223> OTHER INFORMATION: M = A, C
<220> FEATURE:
<221> NAME/KEY: modified_base
<222> LOCATION: (15)..(15)
<223> OTHER INFORMATION: D = A, G
<220> FEATURE:
<221> NAME/KEY: modified_base
<222> LOCATION: (18)..(18)
<223> OTHER INFORMATION: R = A, G

<400> SEQUENCE: 59
atwacncaam twccdttrg                                                19
```

<210> SEQ ID NO 60
<211> LENGTH: 17
<212> TYPE: DNA
<213> ORGANISM: Artificial
<220> FEATURE:
<223> OTHER INFORMATION: Primer

<400> SEQUENCE: 60
aatgcagatg aatgggg 17

<210> SEQ ID NO 61
<211> LENGTH: 17
<212> TYPE: DNA
<213> ORGANISM: Artificial
<220> FEATURE:
<223> OTHER INFORMATION: Primer

<400> SEQUENCE: 61
tgataatgga gctcgtt 17

<210> SEQ ID NO 62
<211> LENGTH: 3684
<212> TYPE: DNA
<213> ORGANISM: Bacillus thuringiensis

<400> SEQUENCE: 62
ttgacttcaa ataggaaaaa tgagaatgaa attataaatg ctttatcgat tccagctgta 60
tcgaatcatt ccgcacaaat gaatctatca accgatgctc gtattgagga tagcttgtgt 120
atagccgagg ggaacaatat cgatccattt gttagcgcat caacagtcca aacgggtatt 180
aacatagctg gtagaatact aggtgtatta ggcgtaccgt ttgctggaca aatagctagt 240
ttttatagtt ttcttgttgg tgaattatgg ccccgcggca gagatccttg ggaaattttc 300
ctagaacatg tcgaacatct tataagacaa caagtaacag aaaatactag ggatacggct 360
cttgctcgat tacaaggttt aggaaattcc tttagagcct atcaacagtc acttgaagat 420
tggctagaaa accgtgatga tgcaagaacg agaagtgttc tttataccca atatatagcc 480
ttagaacttg attttcttaa tgcgatgccg cttttcgcaa ttagaaacca agaagttcca 540
ttattaatgg tatatgctca agctgcaaat ttacacctat tattattgag agatgcctct 600
ctttttggta gtgaatttgg gcttacatcc caagaaattc aacgttatta tgagcgccaa 660
gtggaaaaaa cgagagaata ttctgattat tgcgcaagat ggtataatac gggtttaaat 720
aatttgagag ggacaaatgc tgaaagttgg ttgcgatata atcaattccg tagagactta 780
acgctaggag tattagatct agtggcacta ttcccaagct atgacacgcg tgtttatcca 840
atgaatacca gtgctcaatt aacaagagaa atttatacag atccaattgg gagaacaaat 900
gcaccttcag gatttgcaag tacgaattgg tttaataata atgcaccatc gttttctgcc 960
atagaggctg ccgttattag gcctccgcat ctacttgatt ttccagaaca gcttacaatt 1020
ttcagcgtat taagtcgatg gagtaatact caatatatga attactgggt gggacataga 1080
cttgaatcgc gaacaataag gggtcatta agtacctgga cacacggaaa taccaatact 1140
tctattaatc ctgtaacatt acagttcaca tctcgagacg tttatagaac agaatcattt 1200
gcagggataa atatacttct aactactcct gtgaatggag taccttgggc tagatttaat 1260
tggagaaatc ccctgaattc tcttagaggt agccttctct atactatagg gtatactgga 1320
gtggggacac aactatttga ttcagaaact gaattaccac cagaaacaac agaacgacca 1380
aattatgaat cttacagtca tagattatct aatataagac taatatcagg aaacactttg 1440

```
agagcaccag tatattcttg gacgcaccgt agtgcagatc gtacaaatac cattagttca   1500
gatagcataa cacaaatacc attggtaaaa tcattcaacc ttaattcagg tacctctgta   1560
gtcagtggcc caggatttac aggagggat  ataatccgaa ctaacgttaa tggtagtgta   1620
ctaagtatgg gtcttaattt taataataca tcattacagc ggtatcgcgt gagagttcgt   1680
tatgctgctt ctcaaacaat ggtcctgagg gtaactgtcg gagggagtac tactttgat    1740 caaggattcc ctagtactat gagtgcaaat gagtctttga catctcaatc atttagattt   1800
gcagaatttc ctgtaggtat tagtgcatct ggcagtcaaa ctgctggaat aagtataagt   1860
aataatgcag gtagacaaac gtttcacttt gataaaattg aattcattcc aattactgca   1920
accttcgaag cagaatatga tttagaaaga gcgcaagagg cggtgaatgc tctgtttact   1980
aatacgaatc caagaaggtt gaaaacaggt gtgacagatt atcatattga tgaagtatcc   2040
aatttagtgg cgtgtttatc ggatgaattc tgcttggatg aaaagagaga attacttgag   2100
aaagtgaaat atgcgaaacg actcagtgat gaaagaaact tactccaaga tccaaacttc   2160
acatccatca ataagcaacc agacttcaat tctaataatg agcaatcgaa tttcacatct   2220
atccatgaac aatctgaaca tggatggtgg ggaagtgaga acattacaat ccaggaagga   2280
aatgacgtat ttaaagagaa ttacgtcaca ctaccgggta cttttaatga gtgttatccg   2340
acgtatttat atcaaaaaat aggggaggcg gaattaaaag cttatactcg ctaccaatta   2400
agtggctata ttgaagatag tcaagattta gagatatatt tgattcgtta caatgcgaaa   2460
catgaaacat tggatgttcc aggtaccgag tccgtatggc cgctttcagt tgaaagccca   2520
atcggaaggt gcggagaacc gaatcgatgc gcaccacatt ttgaatggaa tcctgatcta   2580
gattgttcct gcagagatgg agaaaaatgt gcgcatcatt cccatcattt ctctttggat   2640
attgatgttg gatgcataga cttgcatgag aacctaggcg tgtgggtggt attcaagatt   2700
aagacgcagg aaggtcatgc aagactaggg aacctggaat ttattgaaga gaaaccatta   2760
ttaggagaag cactgtctcg tgtgaagaga gcagagaaaa aatggagaga caaacgtgaa   2820
aaactacaat tggaaacaaa acgagtatat acagaggcaa aagaagctgt ggatgcttta   2880
tttgtagatt ctcaatatga tagattacaa gcggatacaa acattggcat gattcatgcg   2940
gcagataaac ttgttcatcg aattcgagag gcgtatcttt cagaattatc tgttatccca   3000
ggtgtaaatg cggaaatttt tgaagaatta gaaggtcgca ttatcactgc aatctcccta   3060
tacgatgcga gaaatgtcgt taaaaatggt gattttaata tggattagc  atgctggaat   3120 gtaaagggc  atgtagatgt acaacagagc catcaccgtt ctgtccttgt tatcccagaa   3180
tgggaagcag aagtgtcaca agcagttcgc gtctgtccgg ggcgtggcta tatcctccgt   3240
gtcacagcgt acaaagaggg atatggagag ggttgtgtaa ctatccatga aatcgagaac   3300
aatacagacg aactaaaatt taaaaactgt gaagaagagg aagtgtatcc aacgatacaa   3360
ggaacgtgta atgattatac tgcacaccaa ggtacagcag tatgtaattc ccgtaatgct   3420
ggatatgagg atgcatatga agttgatact acagcatctg ttaattacaa accgacttat   3480
gaagaagaaa cgtatacaga tgtacgaaga gataatcatt gtgaatatga cagagggtat   3540
gtgaattatc caccagtacc agctggttat atgacaaaag aattagaata cttcccagaa   3600
accgataagg tatggattga gattggagaa acggaaggga gtttattgt  agacagcgtg   3660 gaattactcc ttatggagga atag                                          3684
```

<210> SEQ ID NO 63
<211> LENGTH: 1227
<212> TYPE: PRT
<213> ORGANISM: Bacillus thuringiensis

<400> SEQUENCE: 63

```
Leu Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu His Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365
```

-continued

```
Ser Leu Ser Thr Trp Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ser Phe
            500                 505                 510

Asn Leu Asn Ser Gly Thr Ser Val Val Ser Gly Pro Gly Phe Thr Gly
        515                 520                 525

Gly Asp Ile Ile Arg Thr Asn Val Asn Gly Ser Val Leu Ser Met Gly
    530                 535                 540

Leu Asn Phe Asn Asn Thr Ser Leu Gln Arg Tyr Arg Val Arg Val Arg
545                 550                 555                 560

Tyr Ala Ala Ser Gln Thr Met Val Leu Arg Val Thr Val Gly Gly Ser
                565                 570                 575

Thr Thr Phe Asp Gln Gly Phe Pro Ser Thr Met Ser Ala Asn Glu Ser
            580                 585                 590

Leu Thr Ser Gln Ser Phe Arg Phe Ala Glu Phe Pro Val Gly Ile Ser
        595                 600                 605

Ala Ser Gly Ser Gln Thr Ala Gly Ile Ser Ile Ser Asn Asn Ala Gly
    610                 615                 620

Arg Gln Thr Phe His Phe Asp Lys Ile Glu Phe Ile Pro Ile Thr Ala
625                 630                 635                 640

Thr Phe Glu Ala Glu Tyr Asp Leu Glu Arg Ala Gln Glu Ala Val Asn
                645                 650                 655

Ala Leu Phe Thr Asn Thr Asn Pro Arg Arg Leu Lys Thr Gly Val Thr
            660                 665                 670

Asp Tyr His Ile Asp Glu Val Ser Asn Leu Val Ala Cys Leu Ser Asp
        675                 680                 685

Glu Phe Cys Leu Asp Glu Lys Arg Glu Leu Leu Glu Lys Val Lys Tyr
    690                 695                 700

Ala Lys Arg Leu Ser Asp Glu Arg Asn Leu Leu Gln Asp Pro Asn Phe
705                 710                 715                 720

Thr Ser Ile Asn Lys Gln Pro Asp Phe Asn Ser Asn Asn Glu Gln Ser
                725                 730                 735

Asn Phe Thr Ser Ile His Glu Gln Ser Glu His Gly Trp Trp Gly Ser
            740                 745                 750

Glu Asn Ile Thr Ile Gln Glu Gly Asn Asp Val Phe Lys Glu Asn Tyr
        755                 760                 765

Val Thr Leu Pro Gly Thr Phe Asn Glu Cys Tyr Pro Thr Tyr Leu Tyr
    770                 775                 780
```

-continued

```
Gln Lys Ile Gly Glu Ala Glu Leu Lys Ala Tyr Thr Arg Tyr Gln Leu
785                 790                 795                 800

Ser Gly Tyr Ile Glu Asp Ser Gln Asp Leu Glu Ile Tyr Leu Ile Arg
            805                 810                 815

Tyr Asn Ala Lys His Glu Thr Leu Asp Val Pro Gly Thr Glu Ser Val
        820                 825                 830

Trp Pro Leu Ser Val Glu Ser Pro Ile Gly Arg Cys Gly Glu Pro Asn
    835                 840                 845

Arg Cys Ala Pro His Phe Glu Trp Asn Pro Asp Leu Asp Cys Ser Cys
850                 855                 860

Arg Asp Gly Glu Lys Cys Ala His His Ser His His Phe Ser Leu Asp
865                 870                 875                 880

Ile Asp Val Gly Cys Ile Asp Leu His Glu Asn Leu Gly Val Trp Val
                885                 890                 895

Val Phe Lys Ile Lys Thr Gln Glu Gly His Ala Arg Leu Gly Asn Leu
            900                 905                 910

Glu Phe Ile Glu Glu Lys Pro Leu Leu Gly Glu Ala Leu Ser Arg Val
        915                 920                 925

Lys Arg Ala Glu Lys Lys Trp Arg Asp Lys Arg Glu Lys Leu Gln Leu
    930                 935                 940

Glu Thr Lys Arg Val Tyr Thr Glu Ala Lys Glu Ala Val Asp Ala Leu
945                 950                 955                 960

Phe Val Asp Ser Gln Tyr Asp Arg Leu Gln Ala Asp Thr Asn Ile Gly
                965                 970                 975

Met Ile His Ala Ala Asp Lys Leu Val His Arg Ile Arg Glu Ala Tyr
            980                 985                 990

Leu Ser Glu Leu Ser Val Ile Pro  Gly Val Asn Ala Glu  Ile Phe Glu
        995                1000               1005

Glu Leu  Glu Gly Arg Ile Ile  Thr Ala Ile Ser Leu  Tyr Asp Ala
    1010               1015                    1020

Arg Asn  Val Val Lys Asn Gly  Asp Phe Asn Asn Gly  Leu Ala Cys
    1025               1030                    1035

Trp Asn  Val Lys Gly His Val  Asp Val Gln Gln Ser  His His Arg
    1040               1045                    1050

Ser Val Leu Val Ile Pro Glu  Trp Glu Ala Glu Val  Ser Gln Ala
    1055               1060                    1065

Val Arg Val Cys Pro Gly Arg  Gly Tyr Ile Leu Arg  Val Thr Ala
    1070               1075                    1080

Tyr Lys Glu Gly Tyr Gly Glu  Gly Cys Val Thr Ile  His Glu Ile
    1085               1090                    1095

Glu Asn  Asn Thr Asp Glu Leu  Lys Phe Lys Asn Cys  Glu Glu Glu
    1100               1105                    1110

Glu Val Tyr Pro Thr Asp Thr  Gly Thr Cys Asn Asp  Tyr Thr Ala
    1115               1120                    1125

His Gln Gly Thr Ala Val Cys  Asn Ser Arg Asn Ala  Gly Tyr Glu
    1130               1135                    1140

Asp Ala Tyr Glu Val Asp Thr  Thr Ala Ser Val Asn  Tyr Lys Pro
    1145               1150                    1155

Thr Tyr Glu Glu Glu Thr  Thr Asp Val Arg Arg  Asp Asn His
    1160               1165                    1170

Cys Glu Tyr Asp Arg Gly Tyr  Val Asn Tyr Pro Pro  Val Pro Ala
    1175               1180                    1185
```

```
-continued

Gly Tyr Met Thr Lys Glu Leu Glu Tyr Phe Pro Glu Thr Asp Lys
    1190            1195            1200

Val Trp Ile Glu Ile Gly Glu Thr Glu Gly Lys Phe Ile Val Asp
    1205            1210            1215

Ser Val Glu Leu Leu Leu Met Glu Glu
    1220            1225
```